(12) United States Patent
Wu et al.

(10) Patent No.: US 11,929,143 B2
(45) Date of Patent: Mar. 12, 2024

(54) METHODS FOR NON-INVASIVE ASSESSMENT OF COPY NUMBER ALTERATIONS

(71) Applicant: Sequenom, Inc., San Diego, CA (US)

(72) Inventors: Yijin Wu, San Diego, CA (US); Amin Mazloom, Del Mar, CA (US); Yang Zhong, San Diego, CA (US); Mostafa Azab, San Diego, CA (US)

(73) Assignee: SEQUENOM, INC, San Diego, CA (US)

( * ) Notice: Subject to any disclaimer, the term of this patent is extended or adjusted under 35 U.S.C. 154(b) by 1142 days.

(21) Appl. No.: 16/477,923

(22) PCT Filed: Jan. 22, 2018

(86) PCT No.: PCT/US2018/014714
§ 371 (c)(1),
(2) Date: Jul. 15, 2019

(87) PCT Pub. No.: WO2018/136882
PCT Pub. Date: Jul. 26, 2018

(65) Prior Publication Data
US 2019/0371428 A1    Dec. 5, 2019

Related U.S. Application Data

(60) Provisional application No. 62/448,594, filed on Jan. 20, 2017.

(51) Int. Cl.
| | |
|---|---|
| *G16B 20/10* | (2019.01) |
| *C12Q 1/68* | (2018.01) |
| *G16B 20/20* | (2019.01) |
| *G16B 30/10* | (2019.01) |
| *G16B 40/00* | (2019.01) |

(52) U.S. Cl.
CPC .............. *G16B 20/10* (2019.02); *C12Q 1/68* (2013.01); *G16B 20/20* (2019.02); *G16B 30/10* (2019.02); *G16B 40/00* (2019.02)

(58) Field of Classification Search
CPC combination set(s) only.
See application file for complete search history.

(56) References Cited

U.S. PATENT DOCUMENTS

2016/0239604 A1   8/2016   Chudova et al.

OTHER PUBLICATIONS

Paweletz, C.P. et al. Bias-Corrected Targeted Next-Generation Sequencing for Rapid, Multiplexed Detection of Actionable Alterations in Cell-Free DNA from Advanced Lung Cancer Patients Targeted NGS of Cell-Free DNA from Advanced NSCLC. Clinical Cancer Research, 22(4), pp. 915-922. (Year: 2016).*
Paweletz, C.P. et al. Supplemental Methods: Bias-Corrected Targeted Next-Generation Sequencing for Rapid, Multiplexed Detection of Actionable Alterations in Cell-Free DNA from Advanced Lung Cancer Patients Targeted NGS of Cell-Free DNA from Advanced NSCLC. Clinical Cancer Research, 22(4), pp. 1-4. (Year: 2016).*
Boeva, V. et al. Multi-factor data normalization enables the detection of copy number aberrations in amplicon sequencing data. Bioinformatics, 30(24), pp. 3443-3450. (Year: 2014).*
Budczies, J. et al. Ioncopy: a novel method for calling copy number alterations in amplicon sequencing data including significance assessment. Oncotarget, 7(11), p. 13236-13247. (Year: 2016).*
Paweletz et al., Nature Medicine, 20, p. 1-9, Supplemental Table 3 (Year: 2016).*
CA 3,049,457, Office Action, dated Apr. 7, 2021, 5 pages.
CA 3,049,457, Office Action, dated Jul. 23, 2020, 6 pages.
Benjamini, Y. et al., "Summarizing and Correcting the GC Content Bias in High-Throughput Sequencing", Nucleic Acids Research, vol. 40, No. 10, Feb. 9, 2012, pp. 1-14.
Heitzer, E., et al., "Non-Invasive Detection of Genome-Wide Somatic Copy Number Alterations by Liquid Biopsies", Molecular Oncology, vol. 10, No. 3, Dec. 17, 2015, pp. 494-502.
PCT/US2018/014714, "International Search Report and Written Opinion", dated May 22, 2018, 12 pages.
Xia, Y., et al., "Copy Number Variations in Urine Cell Free DNA as Biomarkers in Advanced Prostate Cancer", Oncotarget, vol. 7, No. 24, Jun. 14, 2016, pp. 35818-35831.
PCT/US2018/014714, "International Preliminary Report on Patentability," dated Aug. 1, 2019, 8 pages.

* cited by examiner

*Primary Examiner* — Lori A. Clow
*Assistant Examiner* — Janna Nicole Schultzhaus
(74) *Attorney, Agent, or Firm* — Kilpatrick Townsend & Stockton LLP

(57) ABSTRACT

Technology provided herein relates in part to methods, processes, machines and apparatuses for non-invasive assessment of copy number alterations. In particular, a method is provided for determining presence or absence of a copy number alteration for a test subject. The method includes providing a set of sequence reads. The sequence reads may be obtained from circulating cell free sample nucleic acid from a test sample obtained from the test subject, and the circulating cell free sample nucleic acid may be captured by probe oligonucleotides under hybridization conditions. The method further includes determining a probe coverage quantification of the sequence reads for the probe oligonucleotides and determining the presence or absence of a copy number alteration in the circulating cell free sample nucleic acid based on the probe coverage quantification of the sequence reads for the probe oligonucleotides for the test sample.

17 Claims, 20 Drawing Sheets

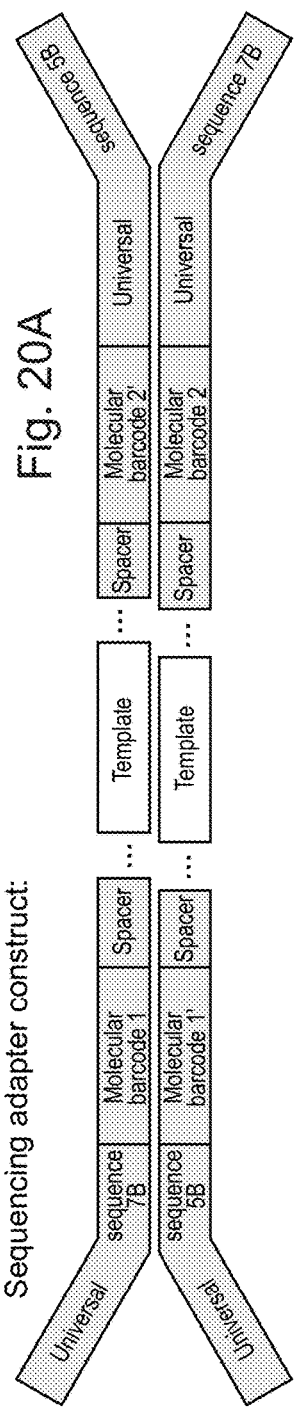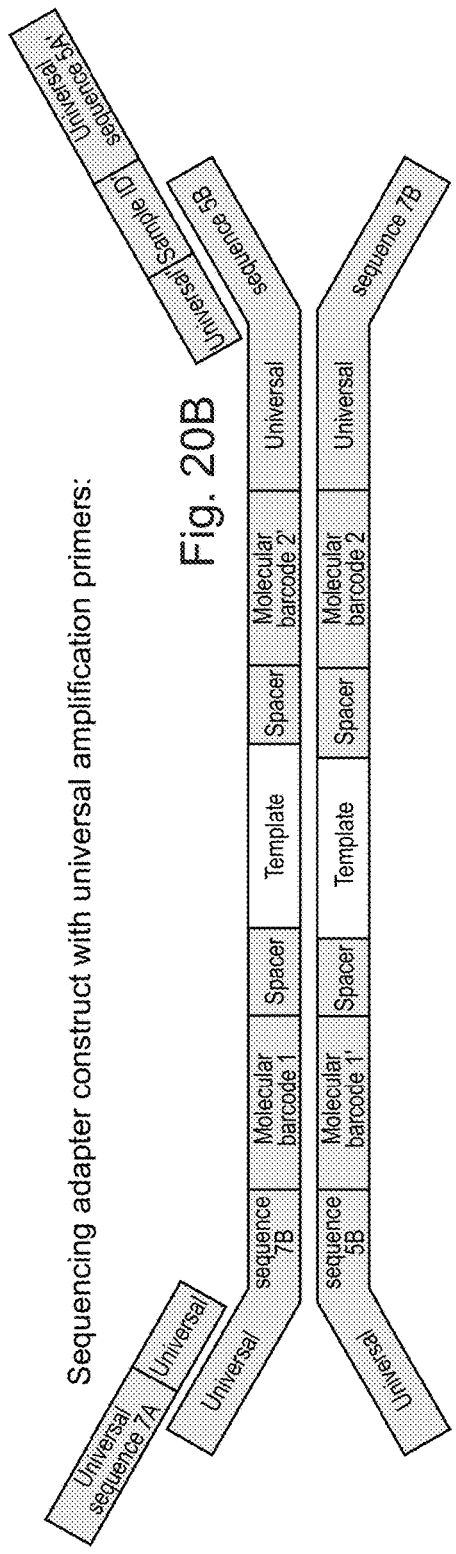

METHODS FOR NON-INVASIVE ASSESSMENT OF COPY NUMBER ALTERATIONS

RELATED APPLICATIONS

This application is a U.S. national phase of International Application PCT/US2018/014714 filed on Jan. 22, 2018, which claims priority to U.S. Provisional Patent Application 62/448,594 filed Jan. 20, 2017. The entire contents of each of which is incorporated herein in its' entirety for all purposes.

FIELD

Technology provided herein relates in part to methods, processes, machines and apparatuses for non-invasive assessment of copy number alterations. Technology provided herein is useful for classifying a copy number alteration for a sample as part of non-invasive pre-natal (NIPT) testing and oncology testing, for example.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on 24 chromosomes (i.e., 22 autosomes, an X chromosome and a Y chromosome; see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations and/or genetic alterations. Certain genetic variations and/or genetic alterations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and a cell proliferative disorder such as a cancer, tumor, neoplasm, metastatic disease, the like or combination thereof. A cancer, tumor, neoplasm, or metastatic disease sometimes is a disorder or condition of the liver, lung, spleen, pancreas, colon, skin, bladder, eye, brain, esophagus, head, neck, ovary, testes, prostate, the like or combination thereof.

Identifying one or more genetic variations and/or genetic alterations (e.g., copy number alterations, copy number variations, single nucleotide alterations, single nucleotide variations, chromosome alterations, translocations, deletions, insertions, and the like) or variances can lead to diagnosis of, or determining predisposition to, a particular medical condition. Identifying a genetic variance can result in facilitating a medical decision and/or employing a helpful medical procedure. In certain embodiments, identification of one or more genetic variations and/or genetic alterations involves the analysis of circulating cell-free nucleic acid. Circulating cell-free nucleic acid (CCF-NA), such as cell-free DNA (CCF-DNA) for example, is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

In various embodiments, a method is provided for determining presence or absence of a copy number alteration for a test subject. The method includes: providing a set of sequence reads, where the sequence reads are obtained from circulating cell free sample nucleic acid from a test sample obtained from the test subject, and the circulating cell free sample nucleic acid is captured by probe oligonucleotides under hybridization conditions; determining, by a computing device, a probe coverage quantification of the sequence reads for the probe oligonucleotides, where the determining the probe coverage quantification of the sequence reads comprises determining, by the computing system, a number of the sequence reads that map at each nucleotide position in the probe oligonucleotides; and determining, by the computing device, the presence or absence of a copy number alteration in the circulating cell free sample nucleic acid based on the probe coverage quantification of the sequence reads for the probe oligonucleotides for the test sample.

In some embodiments, the set of sequence reads are mapped to genomic portions of a reference genome, and the probe coverage quantification of the sequence reads for the probe oligonucleotides is determined according to the sequence reads mapped to the genomic portions.

In other embodiments, the set of sequence reads are aligned to probe oligonucleotide sequences, and the probe coverage quantification of the sequence reads for the probe oligonucleotides is determined according to the sequence reads aligned to the probe oligonucleotide sequences.

In some embodiments, the method further includes generating, by the computing system, consensus sequences from the set of sequence reads, wherein each of the consensus sequences is generated by collapsing sequence reads from the set of sequence reads to generate a single nucleotide sequence that corresponds to at least a portion of the circulating cell free sample nucleic acid, wherein the determining the probe coverage quantification comprises determining the probe coverage quantification of the consensus sequences for the probe oligonucleotides, and wherein the presence or absence of a copy number alteration in the circulating cell free sample nucleic acid is determined based on the probe coverage quantification of the consensus sequence reads for the probe oligonucleotides for the test sample.

In some embodiments, the method further include normalizing, by the computing system, the probe coverage quantification of the sequence reads for the probe oligonucleotides to obtain a normalized probe coverage quantification of the sequence reads for the probe oligonucleotides for the test sample, wherein the presence or absence of the copy number alteration in the circulating cell free sample nucleic acid is determined based on the normalized probe coverage quantification of the sequence reads for the probe oligonucleotides for the test sample. In some embodiments, the normalizing comprises scaling, by the computing system, probe coverage quantification of the sequence reads for the probe oligonucleotides to generate a scaled probe coverage quantification for the probe oligonucleotides. In some embodiments, the probe coverage quantification of the sequence reads for the probe oligonucleotides is scaled according to a probe coverage quantification median for all probe oligonucleotides for the test sample. In some embodiments, the probe coverage quantification of the sequence reads for the probe oligonucleotides is divided by the probe coverage median for the probe oligonucleotides in the test sample. In some embodiments, the normalizing comprises normalizing, by the computing system, the probe coverage quantification of the sequence reads for the probe oligonucleotides, and/or normalizing, by the computing system, the scaled probe coverage quantification of the sequence reads for the probe oligonucleotides, according to guanine-cytosine (GC) content to provide a GC normalized probe coverage quantification of the sequence reads for the probe oligonucleotides for the test sample. In some embodiments, the normalizing in comprises normalizing according to GC content for the probe oligonucleotides. In some embodiments, the normalizing according to GC content comprises LOESS normalization.

In some embodiments, the normalizing comprises normalizing, by the computing system, the probe coverage quantification of the sequence reads for the probe oligonucleotides, and/or normalizing, by the computing system, the scaled probe coverage quantification of the sequence reads for the probe oligonucleotides, and/or normalizing, by the computing system, the GC normalized probe coverage quantification of the sequence reads for the probe oligonucleotides, according to a probe coverage median for the probe oligonucleotides obtained from reference samples to generate a reference sample normalized probe coverage quantification of the sequence reads for the probe oligonucleotides for the test sample. In some embodiments, the normalizing according to the probe coverage median comprises dividing each of the probe coverage quantifications of the sequence reads for the probe oligonucleotides, and/or each of the scaled probe coverage quantifications of the sequence reads for the probe oligonucleotides, and/or the GC normalized probe coverage quantifications of the sequence reads for the probe oligonucleotides by the probe coverage median for the probe oligonucleotides obtained from the reference samples to obtain a ratio for the probe oligonucleotides. In some embodiments, the method further includes logarithmically transforming, by the computer system, the reference sample normalized probe coverage quantification of the sequence reads for the probe oligonucleotides or the ratio for the probe oligonucleotides to generate a logarithmically transformed reference sample normalized probe coverage quantification for the probe oligonucleotides or the ratio for the probe oligonucleotides. In some embodiments, the logarithmically transformed reference sample normalized probe coverage quantification for the probe oligonucleotides or the ratio for the probe oligonucleotides is a log 2 transformed reference sample normalized probe coverage quantification for the probe oligonucleotides or a log 2 ratio for the probe oligonucleotides.

In some embodiments, the method further includes applying, by the computing system, a segmentation process that identifies segments according to the probe coverage quantification of the sequence reads for the probe oligonucleotides and/or the normalized probe coverage quantification of the sequence reads for the probe oligonucleotides. In some embodiments, the segmentation process comprises circular binary segmentation. In other embodiments, the segmentation process comprises a modified bayesian piecewise constant regression. In some embodiments, positions for each end of each of the segments, and a probe coverage quantification or the normalized probe coverage quantification, is provided for each of the segments. In some embodiments, the method further includes determining or estimating the number of copies of each of the segments according to the probe coverage quantification or the normalized probe coverage quantification associated with each of the segments to obtain a copy number gain or copy number loss for each of the segments. In some embodiments, the copy number gain or copy number loss for each of the segments is determined or estimated according to a transformation of segment median coverage for each of the segments. In some embodiments, the copy number gain or copy number loss for each of the segments is determined or estimated according to a transformation of segment median coverage log 2 ratio for each of the segments.

In some embodiments, the copy number gain or copy number loss for each of the segments is determined or estimated according to Equation B:

$$CN = 2 * (2^{(segment.median.log\ 2ratio)} - 1) \qquad \text{Equation B}$$

wherein the segment.median.log 2ratio=log 2(segment.tumor.median/segment.reference.median) and CN is the copy number gain or copy number loss for each of the segments.

In some embodiments, the method further includes filtering, by the computing system, the segments according to the probe coverage quantification associated with each of the segments, the normalized probe coverage quantification associated with each of the segments, or the copy number gain or copy number loss for each of the segments in order to obtain filtered segments.

In some embodiments, the segments for which the copy number gain is equal to or greater than a first predetermined number and the segments for which the copy number loss is equal to or less than a second predetermined number are retained as filtered segments, and the segments for which the copy number gain or the copy number loss is between the first predetermined number and the second predetermined number are filtered away.

In various embodiments, a system is provided for classifying presence or absence of a copy number alteration for a test sample. The system includes one or more processors; and memory coupled to the one or more processors, the memory encoded with a set of instructions configured to perform a process comprising: obtaining sequence reads from circulating cell free sample nucleic acid captured from the test sample by probe oligonucleotides under hybridization conditions; determining a number of the sequence reads that map at each nucleotide position in the probe oligonucleotides to obtain a probe coverage quantification of the sequence reads for the probe oligonucleotides; normalizing the probe coverage quantification of the sequence reads for the probe oligonucleotides to obtain a normalized probe coverage quantification of the sequence reads for the probe oligonucleotides; applying a segmentation process that identifies segments according to the normalized probe coverage quantification of the sequence reads for the probe oligonucleotides; and determining the presence or absence of a copy number alteration in the circulating cell free sample nucleic acid based on the segments and the normalized probe coverage quantification of the sequence reads for the probe oligonucleotides.

In some embodiments, the set of sequence reads are mapped to genomic portions of a reference genome, and the probe coverage quantification of the sequence reads for the probe oligonucleotides is determined according to the sequence reads mapped to the genomic portions.

In other embodiments, the set of sequence reads are aligned to probe oligonucleotide sequences, and the probe coverage quantification of the sequence reads for the probe oligonucleotides is determined according to the sequence reads aligned to the probe oligonucleotide sequences.

In some embodiments, the process further comprises generating consensus sequences from the set of sequence reads, wherein each of the consensus sequences is generated by collapsing sequence reads from the set of sequence reads to generate a single nucleotide sequence that corresponds to at least a portion of the circulating cell free sample nucleic acid, wherein the determining the probe coverage quantification comprises determining the probe coverage quantification of the consensus sequences for the probe oligonucleotides, and wherein the presence or absence of a copy number alteration in the circulating cell free sample nucleic acid is determined based on the normalized probe coverage quantification of the consensus sequence reads for the probe oligonucleotides.

In some embodiments, the normalizing comprises scaling the probe coverage quantification of the sequence reads for the probe oligonucleotides to generate a scaled probe coverage quantification for the probe oligonucleotides.

In some embodiments, the probe coverage quantification of the sequence reads for the probe oligonucleotides is scaled according to a probe coverage quantification median for all probe oligonucleotides for the test sample.

In some embodiments, the probe coverage quantification of the sequence reads for the probe oligonucleotides is divided by the probe coverage median for the probe oligonucleotides in the test sample.

In some embodiments, the normalizing comprises normalizing the probe coverage quantification of the sequence reads for the probe oligonucleotides, and/or normalizing the scaled probe coverage quantification of the sequence reads for the probe oligonucleotides, according to guanine-cytosine (GC) content to provide a GC normalized probe coverage quantification of the sequence reads for the probe oligonucleotides. In some embodiments, the normalizing comprises normalizing according to GC content for the probe oligonucleotides. In some embodiments, the normalizing according to GC content comprises LOESS normalization.

In some embodiments, the normalizing comprises normalizing the probe coverage quantification of the sequence reads for the probe oligonucleotides, and/or normalizing the scaled probe coverage quantification of the sequence reads for the probe oligonucleotides, and/or normalizing the GC normalized probe coverage quantification of the sequence reads for the probe oligonucleotides, according to a probe coverage median for the probe oligonucleotides obtained from reference samples to generate a reference sample normalized probe coverage quantification of the sequence reads for the probe oligonucleotides for the test sample.

In some embodiments, the normalizing according to the probe coverage median comprises dividing each of the probe coverage quantifications of the sequence reads for the probe oligonucleotides, and/or each of the scaled probe coverage quantifications of the sequence reads for the probe oligonucleotides, and/or the GC normalized probe coverage quantifications of the sequence reads for the probe oligonucleotides by the probe coverage median for the probe oligonucleotides obtained from the reference samples to obtain a ratio for the probe oligonucleotides.

In some embodiments, the process further comprises logarithmically transforming the reference sample normalized probe coverage quantification of the sequence reads for the probe oligonucleotides or the ratio for the probe oligonucleotides to generate a logarithmically transformed reference sample normalized probe coverage quantification for the probe oligonucleotides or the ratio for the probe oligonucleotides. In some embodiments, the logarithmically transformed reference sample normalized probe coverage quantification for the probe oligonucleotides or the ratio for the probe oligonucleotides is a log 2 transformed reference sample normalized probe coverage quantification for the probe oligonucleotides or a log 2 ratio for the probe oligonucleotides.

In some embodiments, the segmentation process comprises circular binary segmentation. In other embodiments, the segmentation process comprises a modified bayesian piecewise constant regression.

In some embodiments, the process further comprises determining or estimating the number of copies of each of the segments according to the normalized probe coverage quantification associated with each of the segments to obtain a copy number gain or copy number loss for each of the segments, wherein the copy number gain or copy number loss for each of the segments is determined or estimated according to Equation B:

$$CN = 2*(2^{(segment.median.log\ 2ratio)} - 1) \quad \text{Equation B}$$

wherein the segment.median.log 2ratio=log 2(segment.tumor.median/segment.reference.median) and CN is the copy number gain or copy number loss for each of the segments.

In some embodiments, the process further comprises filtering the segments according to the probe coverage quantification associated with each of the segments, the normalized probe coverage quantification associated with each of the segments, or the copy number gain or copy number loss for each of the segments in order to obtain filtered segments.

In some embodiments, the segments for which the copy number gain is equal to or greater than a first predetermined number and the segments for which the copy number loss is equal to or less than a second predetermined number are retained as filtered segments, and the segments for which the copy number gain or the copy number loss is between the first predetermined number and the second predetermined number are filtered away. In some embodiments, the genomic portions are of equal length. In some embodiments, at least two of the genomic portions are of unequal length. In some embodiments, the 3' ends of the genomic portions abut the 5' end of each adjacent and downstream genomic portion. In some embodiments, at least two of the genomic portions overlap.

In various embodiments, a non-transitory computer readable storage medium is provide for storing instructions that, when executed by one or more processors of a computing system, cause the computing system to perform operations comprising: obtaining sequence reads from circulating cell free sample nucleic acid captured from the test sample by probe oligonucleotides under hybridization conditions; determining a number of the sequence reads that map at each nucleotide position in the probe oligonucleotides to obtain a probe coverage quantification of the sequence reads for the probe oligonucleotides; normalizing the probe coverage quantification of the sequence reads for the probe oligonucleotides to obtain a normalized probe coverage quantification of the sequence reads for the probe oligonucleotides; applying a segmentation process that identifies segments according to the normalized probe coverage quantification of the sequence reads for the probe oligonucleotides; and determining the presence or absence of a copy number alteration in the circulating cell free sample nucleic acid based on the segments and the normalized probe coverage quantification of the sequence reads for the probe oligonucleotides.

In some embodiments, the number of the sequence reads that map at each nucleotide position are determined for each of the probe oligonucleotides to obtain a probe coverage quantification of the sequence reads for each of the probe oligonucleotides.

In some embodiments, the number of the sequence reads that map at each nucleotide position are determined for groups or regions of probe oligonucleotides to obtain a probe coverage quantification of the sequence reads for the groups or regions of probe oligonucleotides.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 20A provides a schematic of annealed oligonucleotide adapters positioned adjacent to nucleic acid template DNA, where oligonucleotide adapters are ligated to both ends of the nucleic acid template.

FIG. 20B is a schematic of the adapters of FIG. 20A, ligated to nucleic acid template DNA, and also depicts universal amplification primers annealed at each end of one of the strands of the construct.

FIG. 20C provides a schematic of the template strand 1 library construct, obtained using the oligonucleotide adapters/nucleic acid template construct and primers of the bottom strand of FIG. 20B.

FIG. 20D provides a schematic of the template strand 2 library construct obtained using the oligonucleotide adapters/nucleic acid template construct and primers of the top strand of FIG. 20B.

DETAILED DESCRIPTION

Figure 1:
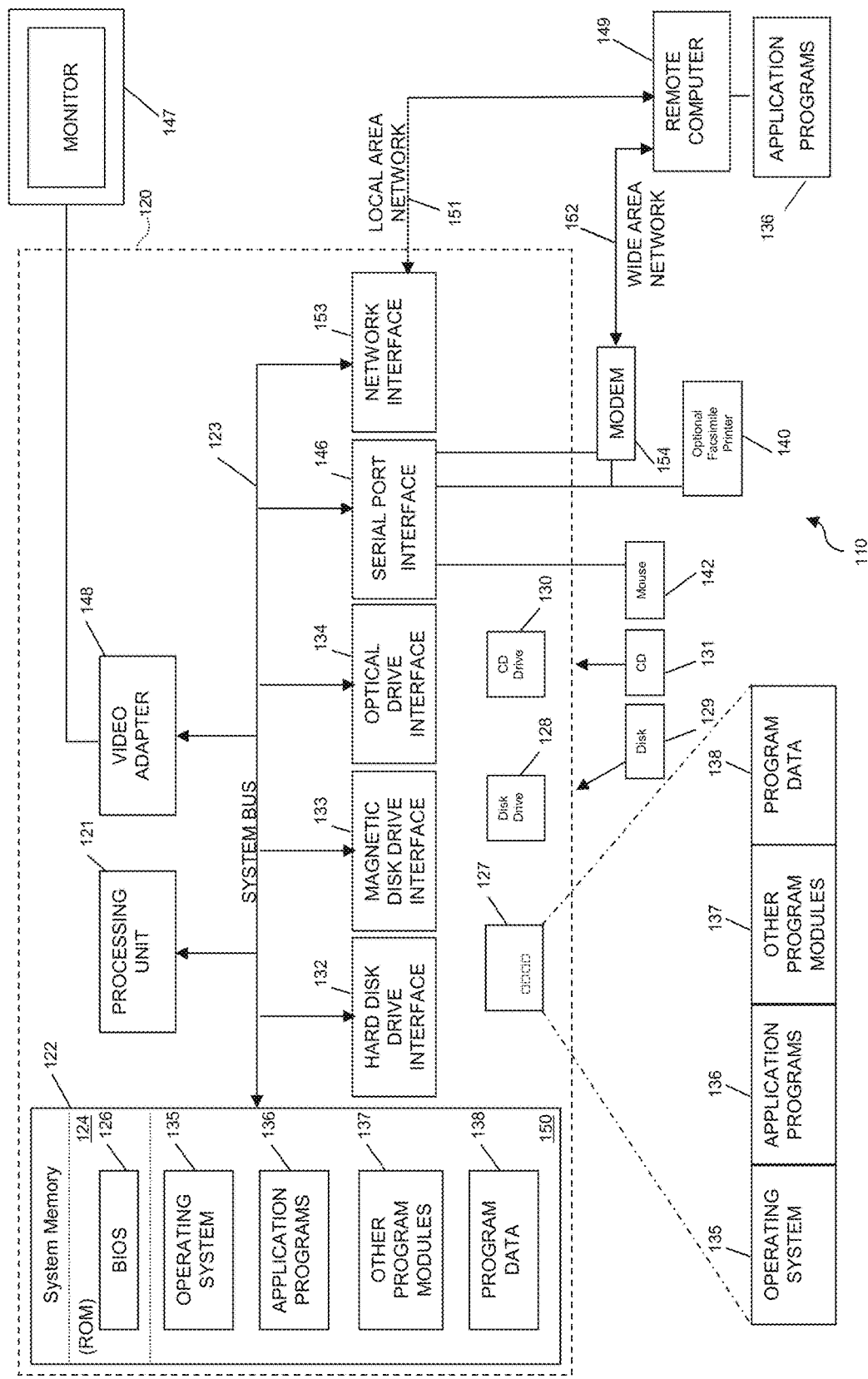
FIG. 1 shows an illustrative embodiment of a system in which certain embodiments of the technology may be implemented.

Provided herein are systems and methods for determining the presence or absence of a genetic alteration such as a copy number alteration for a test subject. In various embodiments, bioinformatic tools and processes are used to detect a genetic alteration in sample polynucleotides. The methods herein may be utilized for a variety of polynucleotides including, for example, fragmented or cleaved nucleic acid, nucleic acid templates, cellular nucleic acid, and/or cell-free nucleic acid. In some embodiments, sample nucleic acid samples or templates are extracted and isolated from a readily accessible bodily fluid such as blood. Following the isolation/extraction step, the samples or templates may be processed before sequencing with one or more reagents (e.g., enzymes, unique identifiers (e.g., barcodes), probes, etc.). In certain embodiments, sample nucleic acid is captured by probe oligonucleotides. For example, the sample nucleic acid may be contacted with probe oligonucleotides under hybridization conditions. A sample nucleic acid may comprise (or consist of) sample polynucleotides and probe oligonucleotides may comprise probe polynucleotides complementary to the sample polynucleotides in the sample nucleic acid. After sequencing data of the sample polynucleotides captured by the probe oligonucleotides is collected, one or more bioinformatic processes may be applied to the sequence data to detect genetic features or aberrations such as the presence or absence of a genetic alteration. In some embodiments, in which genetic alteration analysis is desired, the sequence reads from the sequence data may be: 1) aligned with a reference genome; 2) filtered and mapped; 3) quantified to obtain a quantification of sequence reads or consensus sequences mapped to each nucleotide position in the probe oligonucleotides; 4) collapsed into a consensus sequence; 5) normalized using a stochastic or statistical modeling algorithm; and/or 6) and an output file can be generated reflecting genetic alteration states at various positions in the genome or a portion of the genome such as a specific genomic region targeted by a target capture probe.

Also provided are systems, machines and computer program products that, in some embodiments, carry out methods or parts of methods described herein.

INTRODUCTION

Detection of cell-free nucleic acid in fluid samples offers great potential for use in non-invasive prenatal testing and as a cancer biomarker. In particular, detection of copy number alterations (CNAs) across all chromosomes via low coverage, shotgun sequencing of cfDNA has been validated for noninvasive prenatal screening (NIPS). The validated assay detects CNA events ≥7 Mb across the twenty three autosomes, offering similar resolution to standard G banding techniques when those are combined with invasive sampling. See for example, Lefkowitz R B, Tynan J A, Liu T, Wu Y, Mazloom A R, Almasri E, Hogg G, Angkachatchai V, Zhao C, Grosu D S, McLennan G, Ehrich M; Clinical validation of a noninvasive prenatal test for genomewide detection of fetal copy number variants, *Am J Obstet Gynecol.* 2016 August; 215(2):227.e1-227.e16. doi: 10.1016/j.ajog.2016.02.030. Epub 2016 Feb. 17. In the context of CNA detection from cfDNA for use in cancer screening and treatment monitoring, detection of CNAs with event sizes below the threshold of 7 Mb will likely identify additional clinically relevant CNAs. Since the detection of CNAs in cfDNA is, at least in part, driven by sequencing depth, one could apply additional sequencing reads to the entire genome to increase the number of reads derived from a region of interest. Alternatively, methods have been developed to enrich for particular regions of the genome use hybridization capture and other targeted sequencing approaches. However, analytical methods typically applied to sequencing data obtained from the entire genome or a large portion of the genome are inefficient in their application to targeted sequencing data to enable CNA detection. These inefficiencies are caused at least in part by coverage biases introduced from target capture and sequencing, as well as the non-continuous nature of target regions.

In order to address these problem, various embodiments described herein introduce analytical methods that could be applied to targeted sequencing data to enable CNA detection. For the target enrichment process, biotinylated probes (often called baits) may be designed for regions of interest, manufactured, and pooled together in a single reaction well. The target enrichment process works by first denaturing the library/libraries produced from a cfDNA sample and then hybridizing biotinylated probes to the target libraries. Upon completion of the hybridization process, the hybridized probe/library complex may then be precipitated using streptavidin coated beads. The beads may be washed and the enriched libraries may then be amplified using an additional PCR reaction. In some embodiments, methods are provided to detect CNAs from cfDNAs by determining read coverage for each probe within the single reaction well and further processing of such probe coverage (application of normalization, segmentation, and filtering process) to determine the genomic coordinate of the CNA and whether the CNA is a duplication or deletion event. The determination of the read coverage for each probe and further processing using the quantified read coverage allows for bioinformatic tools to more efficiently process the targeted sequencing data to enable CNA detection.

Detection of Copy Number Alterations in Probe Oligonucleotide Captured Nucleic Acid Provided herein are methods and processes for determining the presence or absence of a copy number alteration (e.g., microduplication, microdeletion, aneuploidy). In some embodiments, the presence or absence of a copy number alteration is determined according to a set of sequence reads. As used herein, when an action such as a determination of something is "triggered by", "according to", or "based on" something, this means the action is triggered, according to, or based at least in part on at least a part of the something. In some embodiments, sequence reads are obtained from circulating cell free sample nucleic acid from a test subject captured by probe oligonucleotides under hybridization conditions. In some embodiments, determining the presence or absence of a copy number alteration is determined according to a set of consensus sequences generated from sequence reads. In some embodiments, the presence or absence of a copy number alteration is determined according to a probe coverage quantification. A probe coverage quantification may be a quantification of sequence reads for each probe oligonucleotide. A probe coverage quantification may be a quantification of consensus sequences for each probe oligonucleotide. In some embodiments, the presence or absence of a copy number alteration is determined according to a normalized probe coverage quantification (e.g., a normalized probe coverage quantification of sequence reads for each probe oligonucleotide; a normalized probe coverage quantification of consensus sequences for each probe oligonucleotide). In some embodiments, determining the presence or absence of a copy number alteration comprises a segmentation process. In some embodiments, determining the presence or absence of a copy number alteration comprises a filtering process.

In some embodiments, determining the presence or absence of a copy number alteration is based on a probe coverage quantification or a normalized probe coverage quantification. In some embodiments, "based on" can include other factors such as segments, filtered segments, copy number determination or estimation, copy number gain or loss determination or estimation, filtered copy number determination or estimation, filtered copy number gain or loss determination or estimation, for example. The presence or absence of a copy number alteration may be determined according to a probe coverage quantification, or a normalized probe coverage quantification, for a single probe oligonucleotide, in some embodiments. The presence or absence of a copy number alteration may be determined according to a probe coverage quantification, or a normalized probe coverage quantification, for a plurality of probe oligonucleotides, in some embodiments.

In some embodiments, sample nucleic acid is captured by probe oligonucleotides. A description of a target capture method is described in further detail herein. Typically, in such embodiments, sample nucleic acid is contacted with probe oligonucleotides under hybridization conditions. A sample nucleic acid may comprise (or consist of) sample polynucleotides and probe oligonucleotides may comprise probe polynucleotides complementary to sample polynucleotides in a sample nucleic acid. In some embodiments, hybridization condition stringency permits only probe polynucleotides with 100% complementarity (i.e., no mismatches) to hybridize to sample nucleic acid. In some embodiments, hybridization condition stringency permits probe polynucleotides with one or two mismatches to hybridize to sample nucleic acid. In some embodiments, modified sample nucleic acid is contacted with probe oligonucleotides under hybridization conditions. Sample nucleic acid may be modified, for example, by addition of one or more adapter oligonucleotides (e.g., adapter oligonucleotides described herein). In some embodiments, adapter oligonucleotides are added to sample nucleic acid by a ligation process. In some embodiments, amplified sample nucleic acid is contacted with probe oligonucleotides under hybridization conditions. Sample nucleic acid may be amplified by a suitable amplification process (e.g., an amplification process described herein).

In some embodiments, sample nucleic acid hybridized to probe oligonucleotides is sequenced. In some embodiments, sample nucleic acid is dissociated from probe oligonucleotides prior to sequencing. In some embodiments, sample nucleic acid is dissociated from probe oligonucleotides and amplified prior to sequencing. Any suitable sequencing process may be used such as, for example, a sequencing by synthesis process described herein.

In some embodiments, sequence reads are mapped to portions of a reference genome. Certain methods for mapping sequence reads to portions of a reference genome are described herein. In some embodiments, genomic portions are of fixed length. In some embodiments, genomic portions are of equal length. In some embodiments, genomic portions are about 5 to 150 kilobases, for example 50 kilobases, in length. In some embodiments, at least two genomic portions are of unequal length. In some embodiments, genomic portions do not overlap. In some embodiments, the 3' ends of genomic portions abut the 5' end of each adjacent and downstream genomic portion. In some embodiments, at least two genomic portions overlap.

In some embodiments, sequence reads mapped to a reference genome are matched to probe sequences and identified as on-target reads. In some embodiments, a method herein comprises identifying on-target reads. In some embodiments, a read is identified as on-target when the read aligns with a genomic region corresponding to a probe oligonucleotide sequence. As described in further detail herein, probe oligonucleotide sequences generally align to (i.e., correspond to) specific regions of a genome (e.g., a reference genome) and often comprise nucleotide sequences corresponding to certain genomic sequences of interest. A read that aligns to a genomic region to which a probe oligonucleotide also aligns is considered an on-target read. A sequence read may be considered on target when the entire read length aligns to a genomic region to which a probe oligonucleotide also aligns, in some embodiments. In some embodiments, a read is identified as on-target when part of the read aligns with a genomic region corresponding to a probe oligonucleotide sequence, and part of the read aligns within a genomic region adjacent to a genomic region corresponding to a probe oligonucleotide sequence. Generally, in such instances, the read aligns to a contiguous genomic sequence comprising 1) part of a genomic region corresponding to a probe oligonucleotide sequence and 2) a genomic region adjacent to the genomic region corresponding to a probe oligonucleotide sequence. The latter genomic region may be located upstream or downstream of the genomic region corresponding to a probe oligonucleotide sequence. For example, a sequence read may be considered on target when part of the read (e.g., at least about 5% of the read, 10% of the read, 20% of the read, 30% of the read, 40% of the read, 50% of the read, 60% of the read, 70% of the read, 80% of the read, 90% of the read) aligns with a genomic region corresponding to a probe oligonucleotide sequence and the remainder of the read aligns to a genomic sequence directly upstream or downstream of a genomic region corresponding to a probe oligonucleotide sequence. A sequence read may be considered on target when no part of the read aligns to a probe sequence and the entire read length aligns to a genomic sequence directly upstream or downstream of a genomic region corresponding to a probe oligonucleotide sequence, in some embodiments.

A sequence comprising a probe sequence (i.e., genomic sequence corresponding to a probe sequence) and additional genomic sequence upstream and/or downstream to the probe sequence may be referred to as a padded probe sequence. A collection of padded probe sequences may be referred to as a padded panel. In some embodiments, a padded probe sequence comprises at least 1 nucleotide of genomic sequence directly upstream and/or downstream to the genomic sequence corresponding to the probe sequence. For example, a padded probe sequence may comprise at least about 5, 10, 20, 30, 40, 50, 100, 150, 200, 250, 300, 400, 500 or 1000 nucleotides of genomic sequence directly upstream and/or downstream to the genomic sequence corresponding to the probe sequence. In some embodiments, a padded probe sequence comprises 250 nucleotides of genomic sequence directly upstream and 250 nucleotides of genomic sequence directly downstream to the genomic sequence corresponding to the probe sequence.

Probe oligonucleotide sequences may be stored as a panel of sequences in a database. In some embodiments, reads are aligned directly with probe oligonucleotide sequences (e.g., probe oligonucleotide sequences stored in a table or database, with or without adjacent genomic region sequences as described above), and such reads are identified as on target reads. For example, sequence reads may be aligned to a panel of sequences in a database without first being mapped to a reference genome. A sequence read may be considered on target when the entire read length aligns to a probe sequence, in some embodiments. In some embodiments, sequence reads are aligned directly to padded probe sequences, as described above. For example, a sequence read may be considered on target when part of the read (e.g., at least about 5% of the read, 10% of the read, 20% of the read, 30% of the read, 40% of the read, 50% of the read, 60% of the read, 70% of the read, 80% of the read, 90% of the read) aligns to a probe sequence and the remainder of the read aligns to a genomic sequence directly upstream or downstream of the probe sequence, in some embodiments. A sequence read may be considered on target when no part of the read aligns to a probe sequence and the entire read length aligns to a genomic sequence directly upstream or downstream of the probe sequence, in some embodiments.

In some embodiments, a consensus sequence is generated from sequence reads. In some embodiments, a consensus sequence is generated from sequence reads identified as "on target" reads. Generally, a consensus sequence is generated by collapsing a set of sequence reads (e.g., reads in a read group) to generate a single nucleotide sequence that corresponds to a unique nucleic acid molecule in the sample from which the sequence reads were generated. The consensus sequence is the calculated order of most frequent residues (e.g., nucleotide), found at each position in a sequence or sequence alignment. It represents the results of multiple sequences or sequence alignments in which related sequences or sequence alignments are compared to each other and similar sequence motifs are calculated. Consensus sequences may be generated from read groups by any suitable method including, for example, linear or non-linear methods for consensus making derived from digital communication theory, information theory, or bioinformatics (e.g., averaging, voting, statistical, dynamic programming, maximum a posteriori or maximum likelihood detection, Bayesian, hidden Markov or support vector machine methods, and the like).

In some embodiments, determining the presence or absence of a copy number alteration is determined according to a probe coverage quantification. Probe coverage generally refers to a quantification of sequence reads or consensus sequences mapped to each nucleotide position in a probe oligonucleotide. In some embodiments, the quantification of sequence reads or consensus sequences mapped to each nucleotide position is maintained for each probe. In other embodiments, the quantification of sequence reads or consensus sequences mapped to each nucleotide position is maintained for groups or regions of probes. For example, the quantification of sequence reads or consensus sequences mapped to each nucleotide position may be maintained for a pre-defined bin size of a probe-covered region. In some embodiments, determining a probe coverage quantification comprises determining the number of sequence reads that map at each of the nucleotide positions in a probe oligonucleotide. Sequence reads may be shorter in length than probe oligonucleotides and/or may partially overlap with probe oligonucleotide sequences. Thus, the quantification of sequence reads mapped to each nucleotide in a probe can vary along the length of a probe oligonucleotide. Accordingly, in some embodiments, determining a probe coverage quantification comprises determining a quantile estimate of the population of sequence reads mapped at each of the nucleotide positions in a probe. A quantile estimate may include, for example, median, mean, mode, range, and the like. In some embodiments, determining a probe coverage quantification comprises determining the median number of sequence reads mapped at each of the nucleotide positions in a probe. In some embodiments, the median number of sequence reads mapped at each of the nucleotide positions for each probe oligonucleotide is the probe coverage quantification for each probe oligonucleotide. For example, a probe coverage calculation may include: (i) for a given probe, determine coverage of each position ($C_i$) in the probe, (ii) the probe coverage $C_p$=median($C_i$), and (iii) scale $C_p$ by median of coverage of all probes in the sample. In instances where the sequence read overlaps more than one probe, the counting is based on positions covered by the probe, and thus this issue of overlap would be solved automatically by the quantification process. In some embodiments, determining a probe coverage quantification comprises determining the number of consensus sequences that map at each of the nucleotide positions in a probe oligonucleotide. Consensus sequences may be shorter in length than probe oligonucleotides and/or may partially overlap with probe oligonucleotide sequences. Thus, the quantification of consensus sequences mapped to each nucleotide in a probe can vary along the length of a probe oligonucleotide. Accordingly, in some embodiments, determining a probe coverage quantification comprises determining the median number of consensus sequences mapped at each of the nucleotide positions in a probe.

In some embodiments, determining the presence or absence of a copy number alteration is determined according to a normalized probe coverage quantification. Probe coverage quantifications can be normalized using a suitable normalization process, such as a normalization process described herein. In some embodiments, normalization comprises scaling probe coverage quantifications for each probe oligonucleotide for a test sample. Scaling probe coverage quantifications for each probe oligonucleotide generates a scaled probe coverage quantification for each probe oligonucleotide. In some embodiments, probe coverage quantifications for each probe are scaled according to a probe coverage quantification median for all probe oligonucleotides for a test sample. For example, probe coverage quantifications for each probe oligonucleotide may be divided by a probe coverage quantification median.

In some embodiments, normalization comprises normalizing probe coverage quantifications according to guanine-cytosine (CG) content for each probe oligonucleotide for a test sample. In some embodiments, normalization comprises normalizing scaled probe coverage quantifications according to guanine-cytosine (CG) content for each probe oligonucleotide for a test sample. Normalizing probe coverage quantifications according to GC content for each probe oligonucleotide generates a GC normalized probe coverage quantification for each probe oligonucleotide. In some embodiments, probe coverage quantifications are normalized by a LOESS normalization. LOESS normalization (e.g., GC LOESS) is described in further detail herein.

In some embodiments, normalization comprises normalizing probe coverage quantifications for a test sample according to probe coverage quantifications obtained from reference samples. Reference samples may comprise samples classified as not having a copy number alteration. In some embodiments, reference samples consist of samples classified as not having a copy number alteration. Accordingly, in some embodiments, reference samples comprise or consist of samples that are euploid for each chromosome and chromosome region tested. Reference samples may be from human subjects. In some embodiments, reference samples are from female subjects. In some embodiments, reference samples are from male subjects. In some embodiments, reference samples are from male and female subjects. Reference samples may include samples from one subject or may include samples from multiple subjects. Reference samples may include one reference sample and often include a plurality of samples. For example, reference samples may include 2, 3, 4, 5, 6, 7, 8, 9, 10, 11, 12, 13, 14, 15, 16, 17, 18, 19, 20, 30, 40, 50, 60, 70, 80, 90, 100 or more samples.

In some embodiments, probe coverage quantifications for a test sample are normalized according to probe coverage quantifications obtained from reference samples. In some embodiments, scaled probe coverage quantifications for a test sample are normalized according to probe coverage quantifications obtained from reference samples. In some embodiments, GC normalized probe coverage quantifications for a test sample are normalized according to probe coverage quantifications obtained from reference samples. In some embodiments, probe coverage quantifications for a test sample are normalized according to a probe coverage median for each probe oligonucleotide obtained from reference samples. In some embodiments, scaled probe coverage quantifications for a test sample are normalized according to a probe coverage median for each probe oligonucleotide obtained from reference samples. In some embodiments, GC normalized probe coverage quantifications for a test sample are normalized according to a probe coverage median for each probe oligonucleotide obtained from reference samples. A probe coverage median often is determined according to probe coverage quantifications for the same probe across multiple reference samples. In some embodiments, a probe coverage median is determined according to normalized (e.g., GC normalized) probe coverage quantifications for the same probe across multiple reference samples. Normalizing probe coverage quantifications (or scaled probe coverage quantifications or GC normalized probe coverage quantifications) for each probe oligonucleotide according to probe coverage quantifications (e.g., probe coverage median) obtained from reference samples generates a reference sample normalized probe coverage quantification for each probe oligonucleotide for a test sample.

In some embodiments, normalizing according to a probe coverage median (e.g., a probe coverage median for each probe oligonucleotide obtained from reference samples) comprises dividing each probe coverage quantification for each probe oligonucleotide (i.e., for a test sample) by a probe coverage median for each probe oligonucleotide obtained from reference samples. In some embodiments, normalizing according to a probe coverage median (e.g., a probe coverage median for each probe oligonucleotide obtained from reference samples) comprises dividing each scaled probe coverage quantification for each probe oligonucleotide (i.e., for a test sample) by a probe coverage median for each probe oligonucleotide obtained from reference samples. In some embodiments, normalizing according to a probe coverage median (e.g., a probe coverage median for each probe oligonucleotide obtained from reference samples) comprises dividing each GC normalized probe coverage quantification for each probe oligonucleotide (i.e., for a test sample) by a probe coverage median for each probe oligonucleotide obtained from reference samples. In such embodiments, normalizing according to a probe coverage median generates a ratio for each probe oligonucleotide.

In some embodiments, probe coverage quantifications are logarithmically transformed. For example, a reference sample normalized probe coverage quantification for each probe oligonucleotide may be logarithmically transformed. Logarithmically transforming a reference sample normalized probe coverage quantification for each probe oligonucleotide generates a logarithmically transformed reference sample normalized probe coverage quantification for each probe oligonucleotide. In certain embodiments, a ratio for each of the probe oligonucleotides is logarithmically transformed. Logarithmically transforming a ratio for each probe oligonucleotide generates a logarithmically transformed ratio for each probe oligonucleotide. In some embodiments, a logarithmic transformation is a log 2 transformation. Accordingly, in some embodiments, a log 2 transformed reference sample normalized probe coverage quantification for each probe oligonucleotide is generated. In some embodiments, a log 2 ratio for each probe oligonucleotide is generated. In certain instances, a log 2 ratio of probe coverage quantifications is proportional to a log 2 ratio for copy number (CN) gain or loss as shown, for example, according to Equation A:

$$\log 2 \text{ ratio} = \log_2 \frac{\text{test coverage}}{\text{normal coverage}} \approx \log_2\left(\frac{CN+2}{2}\right) \quad \text{Equation A}$$

where "test coverage" refers to a probe coverage quantification (e.g., scaled probe coverage quantification, normalized probe coverage quantification) for a probe oligonucleotide for a test sample; "normal coverage" refers to a probe coverage quantification (e.g., probe coverage median) for a probe oligonucleotide obtained from reference samples; and CN is the copy number gain or copy number loss for a segment represented by a probe oligonucleotide (i.e., a segment containing a sequence identical or substantially identical to a probe oligonucleotide sequence).

A normalized probe coverage quantification for a probe oligonucleotide for a test sample may refer to any normalized probe coverage quantification described herein or any suitable variation thereof. For example, a normalized probe coverage quantification for a probe oligonucleotide for a test sample may refer to a scaled probe coverage quantification for a probe oligonucleotide for a test sample. In certain instances, a normalized probe coverage quantification for a probe oligonucleotide for a test sample may refer to a GC normalized probe coverage quantification for a probe oligonucleotide for a test sample. In certain instances, a normalized probe coverage quantification for a probe oligonucleotide for a test sample may refer to a reference sample normalized probe coverage quantification for a probe oligonucleotide for a test sample. In certain instances, a normalized probe coverage quantification for a probe oligonucleotide for a test sample may refer to a ratio for a probe oligonucleotide for a test sample. In certain instances, a normalized probe coverage quantification for a probe oligonucleotide for a test sample may refer to a logarithmically transformed reference sample normalized probe coverage quantification for a probe oligonucleotide for a test sample. In certain instances, a normalized probe coverage quantification for a probe oligonucleotide for a test sample may refer to a logarithmically transformed ratio for a probe oligonucleotide for a test sample. In certain instances, a normalized probe coverage quantification for a probe oligonucleotide for a test sample may refer to a log 2 transformed reference sample normalized probe coverage quantification for a probe oligonucleotide for a test sample. In certain instances, a normalized probe coverage quantification for a probe oligonucleotide for a test sample may refer to a log 2 ratio for a probe oligonucleotide for a test sample.

In some embodiments, a segmentation process is applied to identify a segment or segments (e.g., a segment spanning a copy number alteration). Any suitable segmentation process may be utilized, including without limitation a circular binary segmentation (CBS) process. CBS generally works by iteratively partitioning a chromosome into equal copy number regions using the likelihood ratio statistic. CBS is described, for example, in Olshen et al. (2004) Biostatistics Venkatraman et al. (2007) Bioinformatics 23:657-63; Lai et al. (2005) Bioinformatics 21:3763-70; Willenbrock et al. (2005) Bioinformatics 21:4084-91. In some embodiments, a CBS method is used for detecting CNA (e.g., microduplication, microdeletion) event sizes of about 40 bases or more, more particularly about 80 bases or more. For example, a CBS method may be used for detecting CNA events of about 80 bases, about 100 bases, about 150 bases, about 200 bases, about 250 bases, about 300 bases, about 400 bases, about 500 bases, about 1000 bases, about 2000 bases, about 3000 bases, about 4000 bases, or about 5000 bases or more. In some embodiments, a CBS method is used for detecting CNA event sizes of about 200 bases or more. Other processes could be utilized instead of, or in addition to, CBS, non-limiting examples of which include wavelet segmentation (e.g., Haar wavelet segmentation), Fourier transformation, sliding window z-scores, and Markov chain models.

In other embodiments, the segmentation process includes a modified Bayesian Piecewise Constant Regression (mBPCR) process. BPCR is a Bayesian regression method for data that are noisy observations of a piecewise constant function. The method generally works by estimating the unknown segment number, the endpoints of the segments, and the value of the segment levels of the underlying piecewise constant function. Since copy number data can be modeled as a piecewise function, the BCPR algorithm can be used for their profile estimation or to find segments of constant copy number alterations. Nevertheless, it was found that some estimators defined in the BCPR algorithm gave practical and theoretical problems. Therefore, improved Bayesian estimators have been proposed. The new version of BPCR is mBPCR and has been presented and described, for example, in Hutter, M. (2007a). Bayesian Regression of Piecewise Constant Functions. In Bayesian Statistics: Proceedings of the Eighth Valencia International Meeting. Universitat de Valencia and International Society for Bayesian Analysis, Spain; Hutter, M. (2007b). Exact Bayesian regression of piecewise constant functions. Bayesian Analysis 2(4), 635-664; Rancoita P. M. V., "An Improved Bayesian Method for DNA Copy Number Estimation", Mathematical and statistical aspects of molecular biology (MASAMB08), Glasgow, Mar. 27-28, 2008; and Rancoita, P. M. V., Hutter, M., Bertoni, F., Kwee, I. (2009). Bayesian DNA copy number analysis. BMC Bioinformatics 10:10. In some embodiments, a mBPCR method is used for detecting CNA (e.g., microduplication, microdeletion) event sizes of about 40 bases or more, more particularly 80 bases or more. For example, a mBPCR method may be used for detecting CNA events of about 80 bases, about 100 bases, about 150 bases, about 200 bases, about 250 bases, about 300 bases, about 400 bases, about 500 bases, about 1000 bases, about 2000 bases, about 3000 bases, about 4000 bases, or about 5000 bases or more. In some embodiments, a mBPCR method is used for detecting CNA event sizes of about 200 bases or more. Other processes could be utilized instead of, or in addition to, mBPCR, non-limiting examples of which include wavelet segmentation (e.g., Haar wavelet segmentation), Fourier transformation, sliding window z-scores, and Markov chain models.

In some embodiments, a segmentation process is applied to identify a segment according to a probe coverage quantification for each probe oligonucleotide. In some embodiments, a segmentation process is applied to identify a segment according to a normalized probe coverage quantification for each probe oligonucleotide. A segment sometimes includes multiple probe oligonucleotides (i.e., multiple probe oligonucleotides having probe coverage quantifications indicative of a copy number alteration gain or loss). A segmentation process sometimes provides a start and end position for each segment (e.g., a start and end position according to genomic coordinates; a start and end position according to a probe index), a copy number alteration quantification for the segment, and optionally a measure of confidence for the segment. In some embodiments, positions for each end of each segment (e.g., according to a probe index), and a probe coverage quantification, is provided for each segment. In some embodiments, positions for each end of each segment (e.g., according to a probe index), and a normalized probe coverage quantification, is provided for each segment. In some embodiments, one or more genes that overlap with each segment are identified.

In some embodiments, the number of copies of each segment is determined or estimated according to a probe coverage quantification associated with each segment. In some embodiments, the number of copies of each segment is determined or estimated according to a normalized probe coverage quantification associated with each segment. Determining or estimating the number of copies of each segment provides a copy number (CN) gain or copy number (CN) loss for each of segment. In some embodiments, a copy number (CN) gain or copy number (CN) loss for each segment is determined or estimated according to a transformation of segment median coverage for each segment. Thus, in certain instances, a segment median coverage is determined according to probe coverage quantifications for probe oligonucleotides in a segment. In some embodiments, a copy number (CN) gain or copy number (CN) loss for a segment is determined or estimated according to a transformation of segment median coverage log 2 ratio for each segment. Thus, in certain instances, a median log 2 ratio is determined according to probe coverage quantifications for probe oligonucleotides in a segment. In other words, the median log 2 ratio for probe oligonucleotides in a segment is used for determining or estimating copy number (CN) gain or copy number (CN) loss for a segment. For example, a copy number gain or copy number loss for a segment may be determined or estimated according to Equation B:

$$CN = 2 * (2^{(segment.median.log\ 2ratio)} - 1) \quad \text{Equation B}$$

where segment.median.log 2ratio=log 2(segment.tumor.median/segment.reference.median) and CN is the copy number gain or copy number loss for each segment. In certain embodiments, both tumor and reference profiles are normalized and GC-corrected.

In some embodiments, segments are filtered (e.g., removed from consideration). Segments may be filtered according to one or more of probe coverage quantification associated with a segment, normalized probe coverage quantification associated with a segment, and copy number gain or copy number loss for a segment. Filtering segments generally provides a set of retained filtered segments. Segments often are coupled to a corresponding copy number quantification, and in some embodiments segments for which the value of the corresponding copy number quantification is 0.0 (denoted as CN1) means there is no change in copy number level. In other embodiments, segments for which the value of the corresponding copy number quantification is 1.0 (denoted as CN2) means there is no change in copy number level. Consequently, threshold values may be placed around these values, such as around 0.0 in the first system or around 1.0 in the second system to create parameters for a filter. In some embodiments, segments for which the value of the corresponding copy number quantification is between a first predetermined number and a second predetermined number, for example, between −0.9 (threshold for deletion) and 1.0 (threshold for duplication) may be filtered away as part of a noise reduction filtering process. The transition from one system to the other system may be achieved by the formula: CN2=1+CN1/2, so the corresponding thresholds for deletion and duplication would be 0.55 and 1.5, respectively. In other embodiments, segments for which the absolute value of the corresponding copy number quantification is 0.0 (denoted as CN1) or 1.0 (denoted as CN2) means there is no change in copy number level. Consequently, threshold values may be placed around these values, such as around 0.0 in the first system or around 1.0 in the second system to create parameters for a filter. In some embodiments, segments for which the value of the corresponding copy number quantification is between a first predetermined number and a second predetermined number (for candidate duplications) and third predetermined number and a fourth predetermined number (for candidate deletions), for example between 0 and about 1 (for candidate duplications) or between −0.9 and about 0 (for candidate deletions) may be filtered away as part of a noise reduction filtering process.

In some embodiments, segments for which the copy number gain is equal to or greater than the first predetermined number are retained as filtered segments. For example, segments for which there is a 1 or greater copy number gain (for candidate duplications) may be retained as filtered segments. For example, segments for which there is a 1.1, 1.2, 1.3, 1.4, 1.5, 1.6, 1.7, 1.8, 1.9, 2, 3, 4, 5, 6, 7, 8, 9, 10 or greater copy number gain may be retained as filtered segments. In some embodiments, the segments for which the copy number loss is equal to or less than a second predetermined number are retained as filtered segments, For example, segments for which there is a 0.9 or greater copy number loss (for candidate deletions) may be retained as filtered segments. As copy number quantifications for candidate deletions generally fall below zero, "a 0.9 or greater copy number loss" corresponds to the absolute value of a copy number quantification for a candidate deletion. Thus, for example, segments for which there is a 0.9, 1.0, 1.2, 1.3, 1.4, 1.5, 1.6, 1.7, 1.8, 1.9, or 2 copy number loss may be retained as filtered segments. In other words, segments having a copy number quantification of −0.9, −1.0, −1.2, −1.3, −1.4, −1.5, −1.6, −1.7, −1.8, −1.9, or −2 may be retained as filtered segments. The segments for which the copy number gain or the copy number loss is between the first predetermined number and the second predetermined number are filtered away as part of the noise reduction filtering process.

In some embodiments, a copy number alteration (CNA) is determined according to a z-score method. A z-score may be determined for one or more probe oligonucleotides, and the presence or absence of a copy number alteration may be determined according to the z-score of the one or more probe oligonucleotides for a test sample. In some embodiments, a z-score for each of the probe oligonucleotides is determined according to a test sample coverage quantification, a reference mean coverage quantification, and a reference standard deviation. In some embodiments, a z-score method is used for detecting CNA (e.g., microduplication, microdeletion) event sizes of about 50 bases or more in length. For example, a z-score method may be used for detecting CNA events of about 50 bases, about 75 bases, about 80 bases, about 100 bases, about 125 bases, about 150 bases, about 200 bases, about 300 bases, about 400 bases, about 500 bases, about 1000 bases, about 2000 bases, about 3000 bases, about 4000 bases, or about 5000 bases or more. In some embodiments, a z-score method is used for detecting CNA event sizes of about 80 bases or more in length.

In some embodiments, a test sample coverage quantification is determined. A test sample coverage quantification refers to a probe coverage quantification for a given probe oligonucleotide for a test sample. A test sample coverage quantification may refer to a probe coverage quantification, a scaled probe coverage quantification, a GC normalized probe coverage quantification, and/or any suitable variation of a probe coverage quantification described herein for a given probe oligonucleotide for a test sample. Such coverage quantifications may be determined, for example, according to probe coverage quantification methods described herein.

In some embodiments, a reference mean coverage quantification is determined. A reference mean coverage quantification refers to an average probe coverage quantification for a given probe oligonucleotide determined from probe coverage quantifications for the probe oligonucleotide across a plurality of reference samples. A reference coverage quantification may refer to a probe coverage quantification, a scaled probe coverage quantification, a GC normalized probe coverage quantification, and/or any suitable variation of a probe coverage quantification described herein for a given probe oligonucleotide for a reference sample. Such reference coverage quantifications may be determined, for example, according to probe coverage quantification methods described herein. A reference mean coverage quantification may refer to a mean probe coverage quantification, and/or a mean scaled probe coverage quantification, a mean GC normalized probe coverage quantification, and/or a mean of any suitable variation of a probe coverage quantification described herein for a given probe oligonucleotide across a plurality of reference samples.

In some embodiments, a reference standard deviation is determined. A reference standard deviation refers to the standard deviation of reference coverage quantifications for a given probe oligonucleotide across a plurality of reference samples. A reference standard deviation may refer to a standard deviation of a probe coverage quantification, a standard deviation of a scaled probe coverage quantification, a standard deviation of a GC normalized probe coverage quantification, and/or a standard deviation of any suitable variation of a probe coverage quantification described herein for a given probe oligonucleotide across a plurality of reference samples.

In some embodiments, a z-score is determined or estimated according to Equation C:

$$z = (v - \text{normal\_}v)/sd\_v \qquad \text{Equation C}$$

where z is the z-score for a given probe oligonucleotide in a sample; v is the probe coverage quantification for the probe oligonucleotide, or the scaled probe coverage quantification for the probe oligonucleotide, the GC normalized probe coverage quantification for the probe oligonucleotide, or any suitable probe coverage quantification described herein for the probe oligonucleotide for the test sample; normal_v is the mean probe coverage quantification for the probe oligonucleotide, or the mean scaled probe coverage quantification for the probe oligonucleotide, the mean GC normalized probe coverage quantification for the probe oligonucleotide, or the mean of any suitable probe coverage quantification described herein for the probe oligonucleotide across a plurality of reference samples; and sd_v is the standard deviation for probe coverage quantification for the probe oligonucleotide, the standard deviation for scaled probe coverage quantification for the probe oligonucleotide, the standard deviation for GC normalized probe coverage quantification for the probe oligonucleotide, or the standard deviation of any suitable probe coverage quantification described herein for the probe oligonucleotide across a plurality of reference samples.

In some embodiments, the presence or absence of a copy number alteration is determined according to a z-score cutoff. A z-score cutoff may be determined according to a preferred level of sensitivity and/or specificity for determining the presence or absence of a copy number alteration for a test sample. In some embodiments, a z-score cutoff value may be set at an absolute value of about 2 to about 4. For example, a z-score cutoff value me be set at an absolute value of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0. The presence or absence of a copy number alteration may be determined for a test sample if the absolute value of one or more Z scores for one or more probe oligonucleotides is greater than the selected cutoff value.

In some embodiments, a copy number alteration (CNA) is determined according to a Genome Analysis Toolkit (GATK) variant caller method, which also may be referred to as a Haplotypecaller. The GATK variant caller method utilizes a local de-novo assembly approach and may be used for detecting SNPs, insertions and deletions. Generally, at a point in an alignment where a variation is suspected, original alignments are discarded and reads are reassembled. Steps in this method may be executed in the following order after alignment: duplicate marking of reads, base quality recalibration, and variant discovery. The GATK variant caller method may be performed using any suitable software designed to run GATK such as, for example, software available on the website for Genome Analysis Toolkit. A GATK variant caller method is described, for example, in McKenna et al. (2010) Genome Research 20:1297-303; M. DePristo et al. (2011) Nature Genetics 43:491-498; and Van der Auwera et al. (2013) Current Protocols in Bioinformatics 43:11.10.1-11.10.33, each of which is incorporated by reference herein.

In some embodiments, a GATK variant caller method is used for detecting CNA events (e.g., microduplications, microdeletions) having event sizes between about 25 bases to about 100 bases. For example, a GATK variant caller method may be used for detecting CNA events of about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, and/or about 100 bases. In some embodiments, a GATK variant caller method is used for detecting CNA events having event sizes between about 40 bases to about 95 bases. In some embodiments, a GATK variant caller method is used for detecting CNA events having event sizes between about 45 bases to about 90 bases. In some embodiments, a GATK variant caller method is used for detecting CNA events having event sizes between about 50 bases to about 85 bases.

In some embodiments, a copy number alteration (CNA) is determined according to a PINDEL variant caller method. PINDEL generally utilizes a pattern growth algorithm to identify break points, or edges of an insertion or deletion event. This can be accomplished by identifying read pairs where only one read uniquely maps to a reference genome, and the other read cannot be mapped given an alignment score threshold. The PINDEL variant caller method may be performed using any suitable software designed to run PINDEL such as, for example, software available on the website for PINDEL. A PINDEL variant caller method is described, for example, in Kai Ye et al. (2009) Bioinformatics 25(21):2865-2871, which is incorporated by reference herein.

In some embodiments, a PINDEL variant caller method is used for detecting CNA events (e.g., microduplications, microdeletions) having event sizes between about 25 bases to about 150 bases. For example, a PINDEL variant caller method may be used for detecting CNA events of about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, about 100 bases, about 105 bases, about 110 bases, about 115 bases, about 120 bases, about 125 bases, about 130 bases, about 140 bases, and/or about 150 bases. In some embodiments, a PIINDEL variant caller method is used for detecting CNA events having event sizes between about 50 bases to about 110 bases. In some embodiments, a PINDEL variant caller method is used for detecting CNA events having event sizes between about 55 bases to about 105 bases. In some embodiments, a PINDEL variant caller method is used for detecting CNA events having event sizes between about 60 bases to about 100 bases.

In some embodiments, the presence or absence of a copy number alteration is determined with a certain level of sensitivity and/or specificity. In some embodiments, the presence or absence of a copy number alteration is determined with a sensitivity of about 85% to about 100%. For example, the presence or absence of a copy number alteration may be determined with a sensitivity of about 85%, 86%, 87%, 88%, 89%, 90%, 91%, 92%, 93%, 94%, 95%, 96%, 97%, 98%, 99% or 100%. In some embodiments, the presence or absence of a copy number alteration is determined with a specificity of about 85% to about 100%. For example, the presence or absence of a copy number alteration may be determined with a specificity of about 85%, 86%, 87%, 88%, 89%, 90%, 91%, 92%, 93%, 94%, 95%, 96%, 97%, 98%, 99% or 100%.

Figure 3:
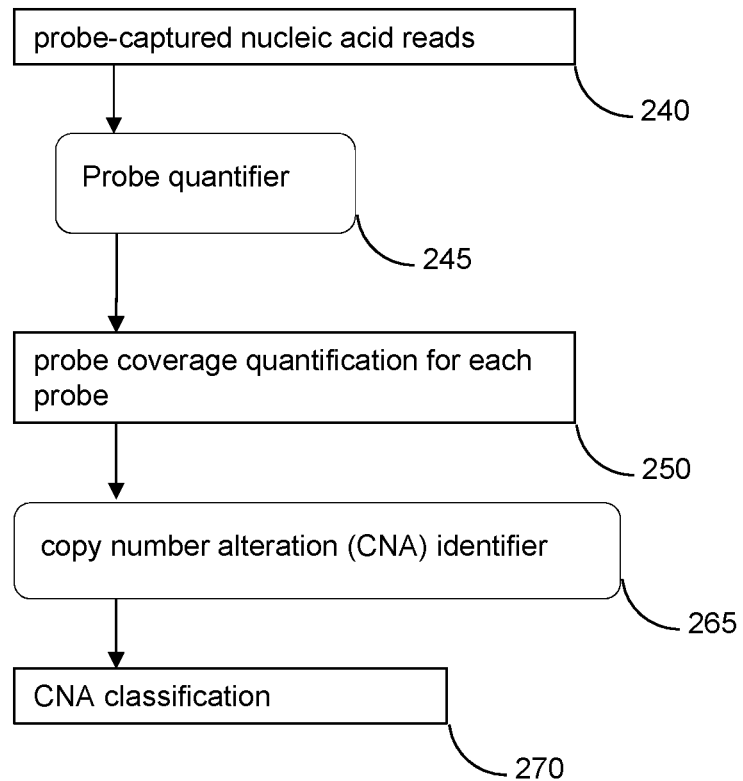
FIG. 3 shows a process flow in accordance with various embodiments.

An embodiment of a copy number alteration (CNA) classification process is illustrated in FIG. 3. Probe-captured nucleic acid reads 240 for a sample (e.g., test sample) are subjected to a probe quantifier 245 and a probe coverage quantification for each probe 250 is determined. Probe coverage quantifications for each probe 250 are input for a copy number alteration (CNA) identifier 265 which generates a CNA classification 270.

Figure 4:
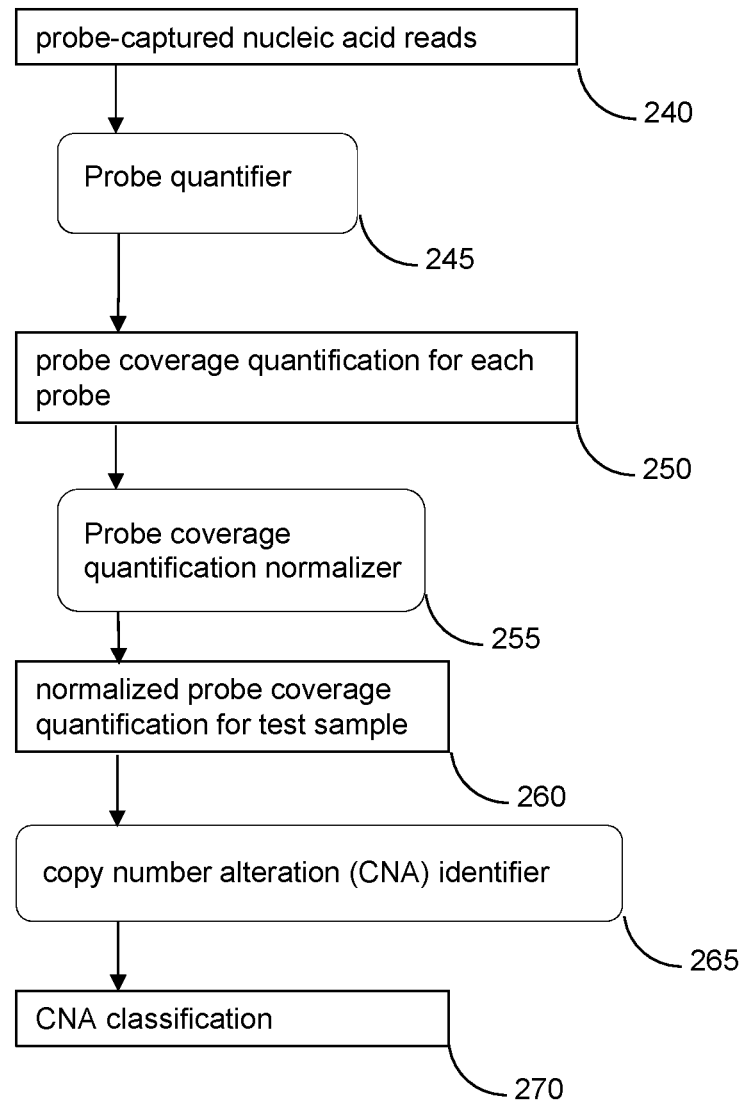
FIG. 4 shows a process flow in accordance with various embodiments.

Another embodiment of a copy number alteration (CNA) classification process is illustrated in FIG. 4. Probe-captured nucleic acid reads 240 for a sample (e.g., test sample) are subjected to a probe quantifier 245 and a probe coverage quantification for each probe 250 is determined. Probe coverage quantifications for each probe 250 are input for a probe coverage quantification normalizer 255 which generates normalized probe coverage quantifications for a test sample 260. Normalized probe coverage quantifications for a test sample 260 are input for a copy number alteration (CNA) identifier 265 which generates a CNA classification 270.

Figure 5:
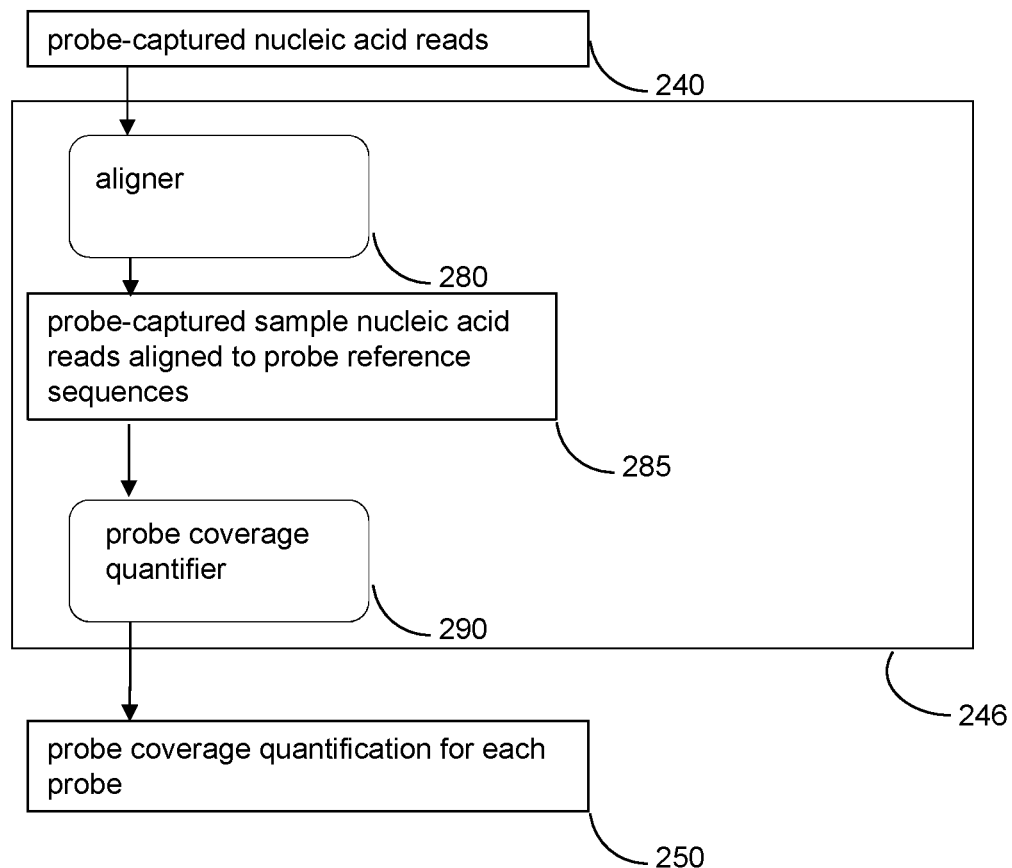
FIG. 5 shows a process flow in accordance with various embodiments.

In some embodiments, a copy number alteration (CNA) classification process comprises a probe coverage quantification process. An embodiment of a probe coverage quantification process is illustrated in FIG. 5. Probe-captured nucleic acid reads 240 for a sample (e.g., test sample) are subjected to a probe quantifier and a probe coverage quantification for each probe 250 is determined. One embodiment of a probe quantifier is illustrated as process 246 in FIG. 5. Probe-captured nucleic acid reads 240 for a sample (e.g., test sample) are input for an aligner 280 which generates probe-captured sample nucleic acid reads aligned to probe reference sequences 285. Probe-captured sample nucleic acid reads aligned to probe reference sequences 285 are input for a probe coverage quantifier 290 which generates a probe coverage quantification for each probe 250.

Figure 6:
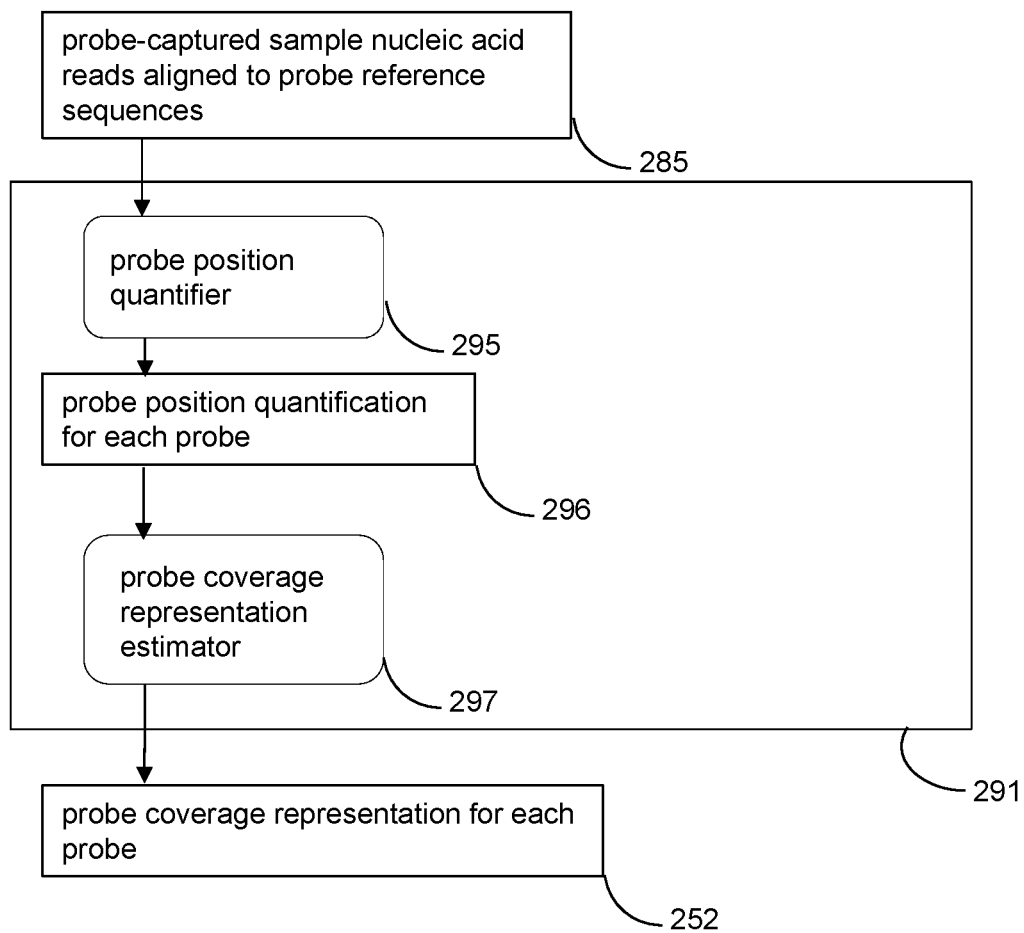
FIG. 6 shows a process flow in accordance with various embodiments.

In some embodiments, a probe coverage quantification process comprises generating a probe coverage representation for each probe. An embodiment of a probe coverage representation process is illustrated in FIG. 6. Probe-captured sample nucleic acid reads aligned to probe reference sequences 285 are subjected to a probe coverage quantifier and a probe coverage representation for each probe 252 is determined. One embodiment of a probe coverage quantifier is illustrated as process 291 in FIG. 6. Probe-captured sample nucleic acid reads aligned to probe reference sequences 285 are input for a probe position quantifier 295 which generates a probe position quantification for each probe 296. Probe position quantifications for each probe 296 are input for a probe coverage representation estimator 297 which generates a probe coverage representation for each probe 252.

Figure 7:
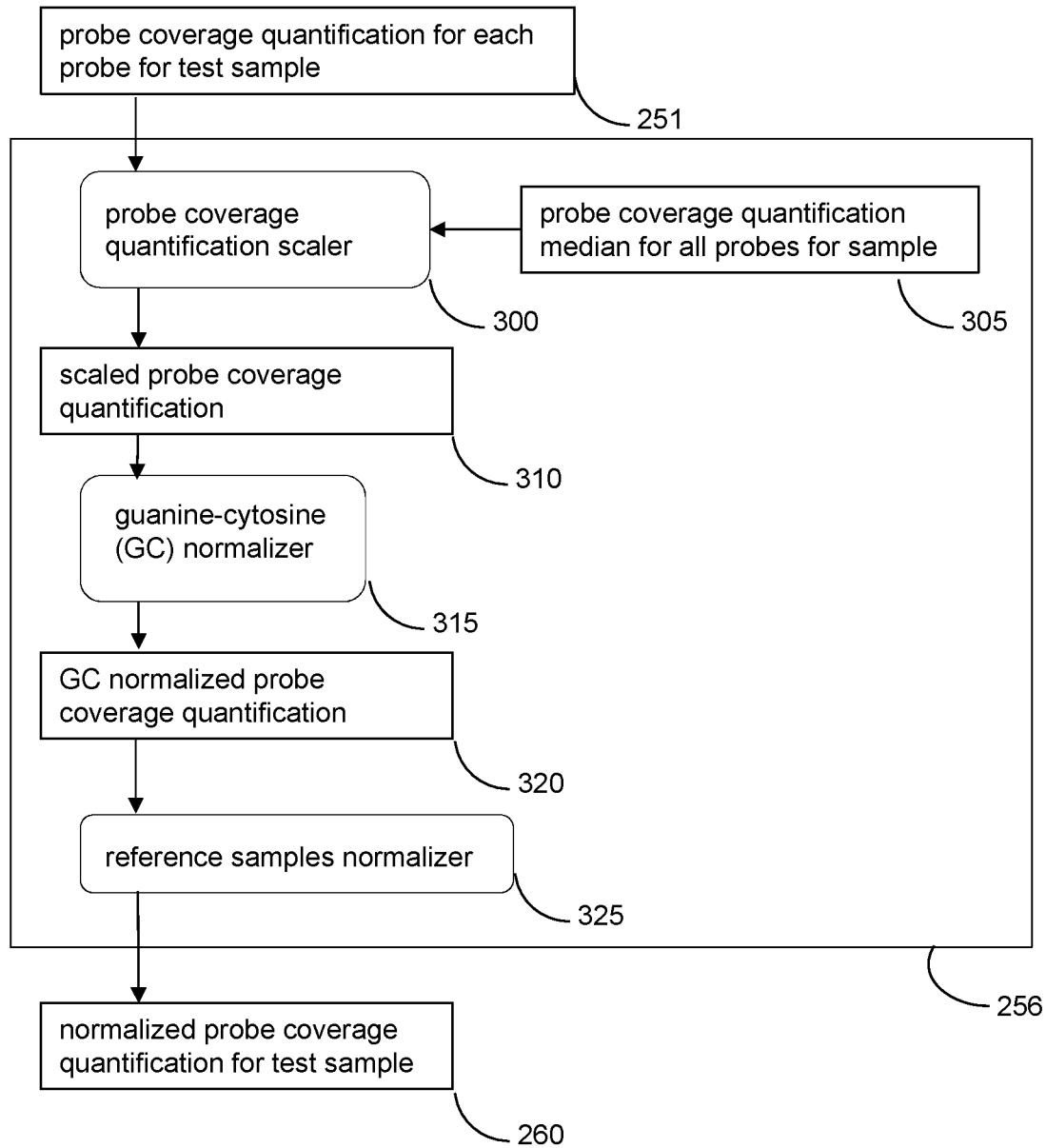
FIG. 7 shows a process flow in accordance with various embodiments.

In some embodiments, a normalized probe coverage quantification for a test sample is determined. An embodiment of a normalized probe coverage quantification is illustrated in FIG. 7. Probe coverage quantifications for each probe for a test sample 251 are subjected to a probe coverage quantification normalizer and a normalized probe coverage quantification for a test sample 260 is determined. One embodiment of a probe coverage quantification normalizer is illustrated as process 256 in FIG. 7. Probe coverage quantifications for each probe for a test sample 251 and a probe coverage quantification median for all probes for a sample 305 are input for a probe coverage quantification scaler 300, which generates a scaled probe coverage quantification 310. Scaled probe coverage quantification 310 is input for a guanine-cytosine (GC) normalizer 315 which generates a GC normalized probe coverage quantification 320. GC normalized probe coverage quantification 320 is input for a reference samples normalizer 325 which generates a normalized probe coverage quantification for a test sample 260.

Figure 8:
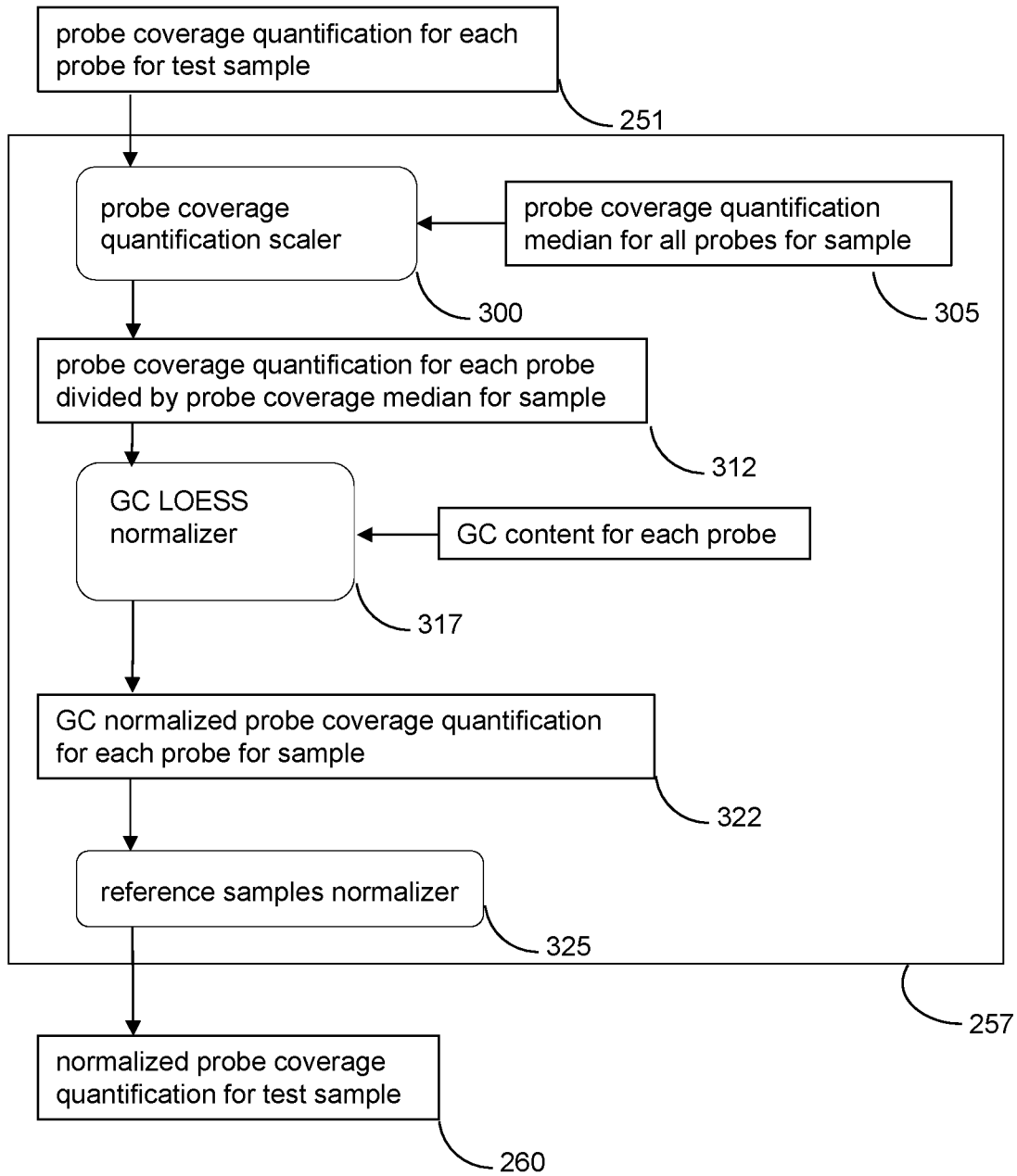
FIG. 8 shows a process flow in accordance with various embodiments.

Another embodiment of a normalized probe coverage quantification is illustrated in FIG. 8. Probe coverage quantifications for each probe for a test sample 251 are subjected to a probe coverage quantification normalizer and a normalized probe coverage quantification for a test sample 260 is determined. One embodiment of a probe coverage quantification normalizer is illustrated as process 257 in FIG. 8. Probe coverage quantifications for each probe for a test sample 251 and a probe coverage quantification median for all probes for a sample 305 are input for a probe coverage quantification scaler 300, which generates a scaled probe coverage quantification (i.e., probe coverage quantification for each probe divided by probe coverage median for sample 312). The scaled probe coverage quantification (i.e., probe coverage quantification for each probe divided by probe coverage median for a sample 312) and GC content for each probe are input for a GC LOESS normalizer 317, which generates a GC normalized probe coverage quantification for each probe for a sample 322. GC normalized probe coverage quantification for each probe for a sample 322 is input for a reference samples normalizer 325 which generates a normalized probe coverage quantification for a test sample 260.

Figure 9:
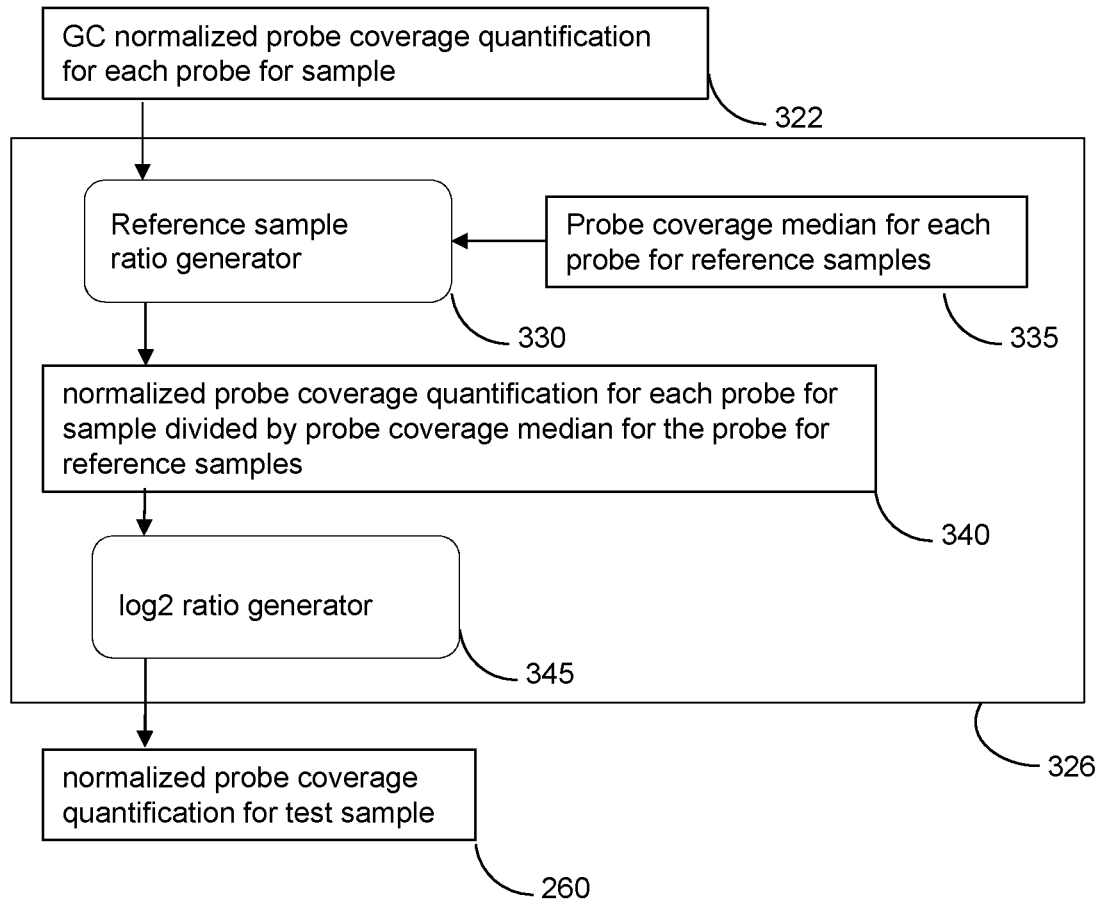
FIG. 9 shows a process flow in accordance with various embodiments.

Another embodiment of a normalized probe coverage quantification is illustrated in FIG. 9. GC normalized probe coverage quantifications for each probe for a sample 322 are subjected to a reference samples normalizer and a normalized probe coverage quantification for a test sample 260 is determined. One embodiment of a reference samples normalizer is illustrated as process 326 in FIG. 9. GC normalized probe coverage quantifications for each probe for a sample 322 and a probe coverage median for each probe for reference samples 335 are input for a reference sample ratio generator 330, which generates a normalized probe coverage quantification for each probe for a sample divided by probe coverage median for the probe for reference samples 340. Normalized probe coverage quantifications for each probe for a sample divided by probe coverage median for the probe for reference samples 340 are input for a log 2 ratio generator 345 which generates a normalized probe coverage quantification for a test sample 260.

Figure 10:
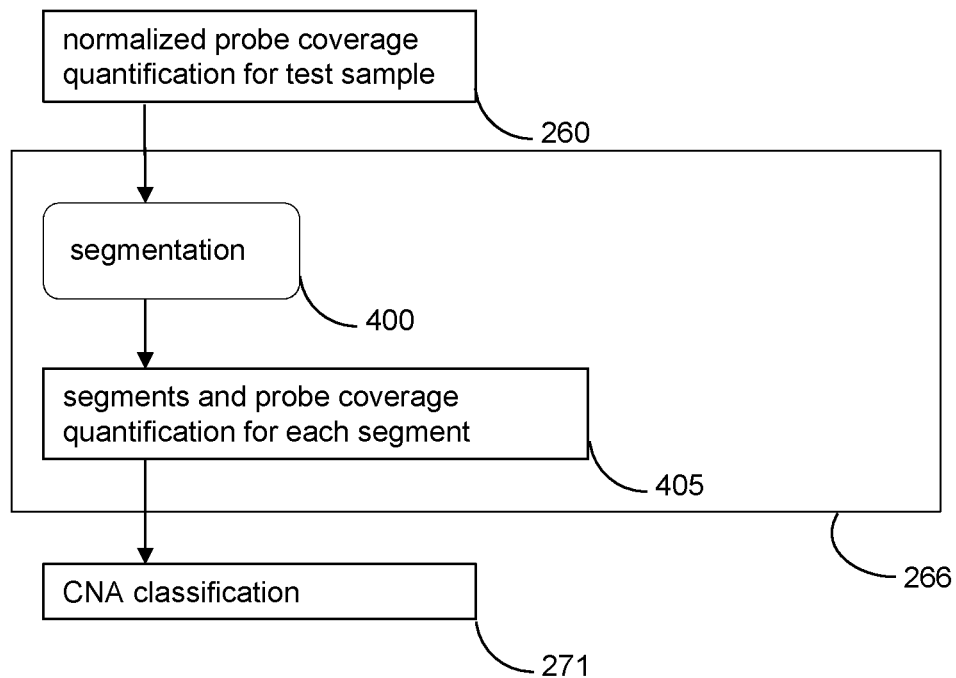
FIG. 10 shows a process flow in accordance with various embodiments.

In some embodiments, a CNA classification is determined according to a normalized probe coverage quantification for a test sample. An embodiment of a CNA classification process is illustrated in FIG. 10. Normalized probe coverage quantifications for a test sample 260 are subjected to a copy number alteration (CNA) identifier and a CNA classification 271 is determined. One embodiment of a copy number alteration (CNA) identifier is illustrated as process 266 in FIG. 10. Normalized probe coverage quantifications for a test sample 260 are input for segmentation 400 which generates segments and probe coverage quantifications for each segment 405. CNA classification 271 may be determined according to the segments and probe coverage quantifications for each segment 405.

Figure 11:
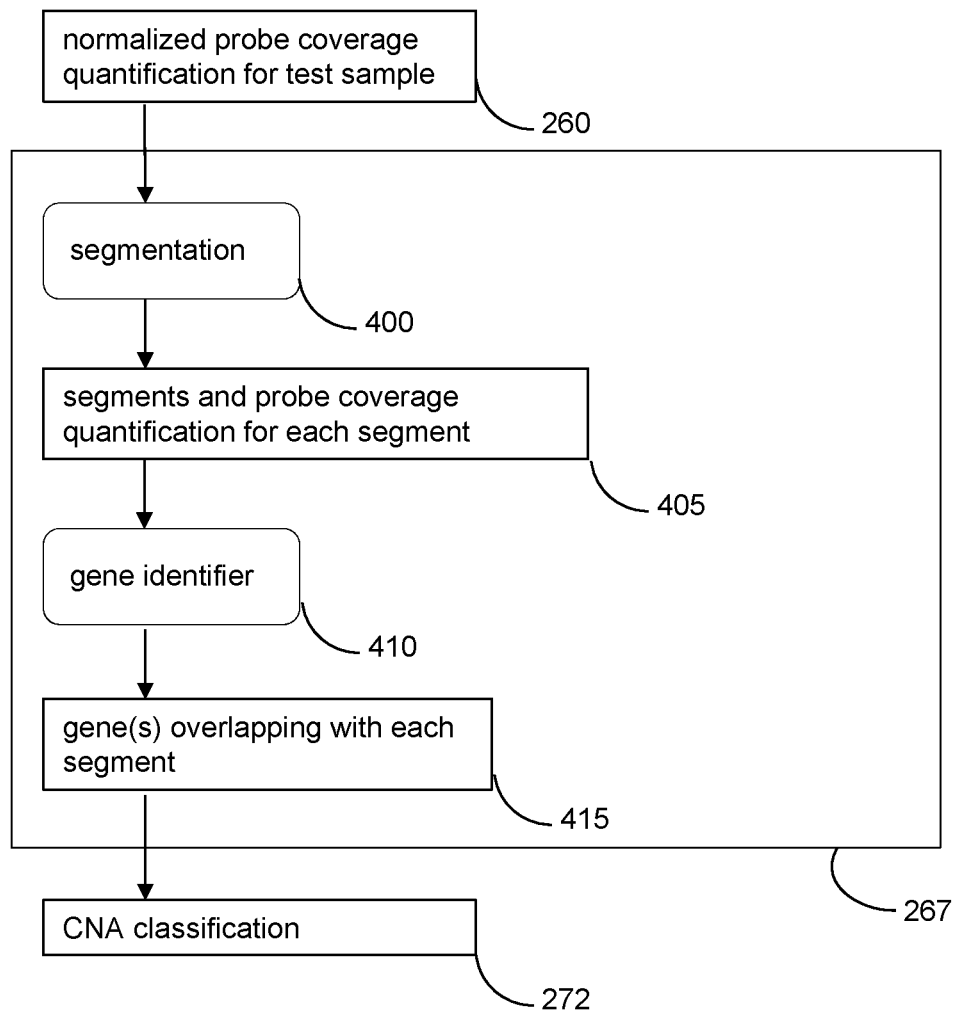
FIG. 11 shows a process flow in accordance with various embodiments.

Another embodiment for a CNA classification process is illustrated in FIG. 11. Normalized probe coverage quantifications for a test sample 260 are subjected to a copy number alteration (CNA) identifier and a CNA classification 272 is determined. One embodiment of a copy number alteration (CNA) identifier is illustrated as process 267 in FIG. 11. Normalized probe coverage quantifications for a test sample 260 are input for segmentation 400 which generates segments and probe coverage quantifications for each segment 405. Segments and probe coverage quantifications for each segment 405 are input for a gene identifier 410, which identifies gene(s) overlapping with each segment 415. CNA classification 272 may be determined according to the identified gene(s) overlapping with each segment 415.

Figure 12:
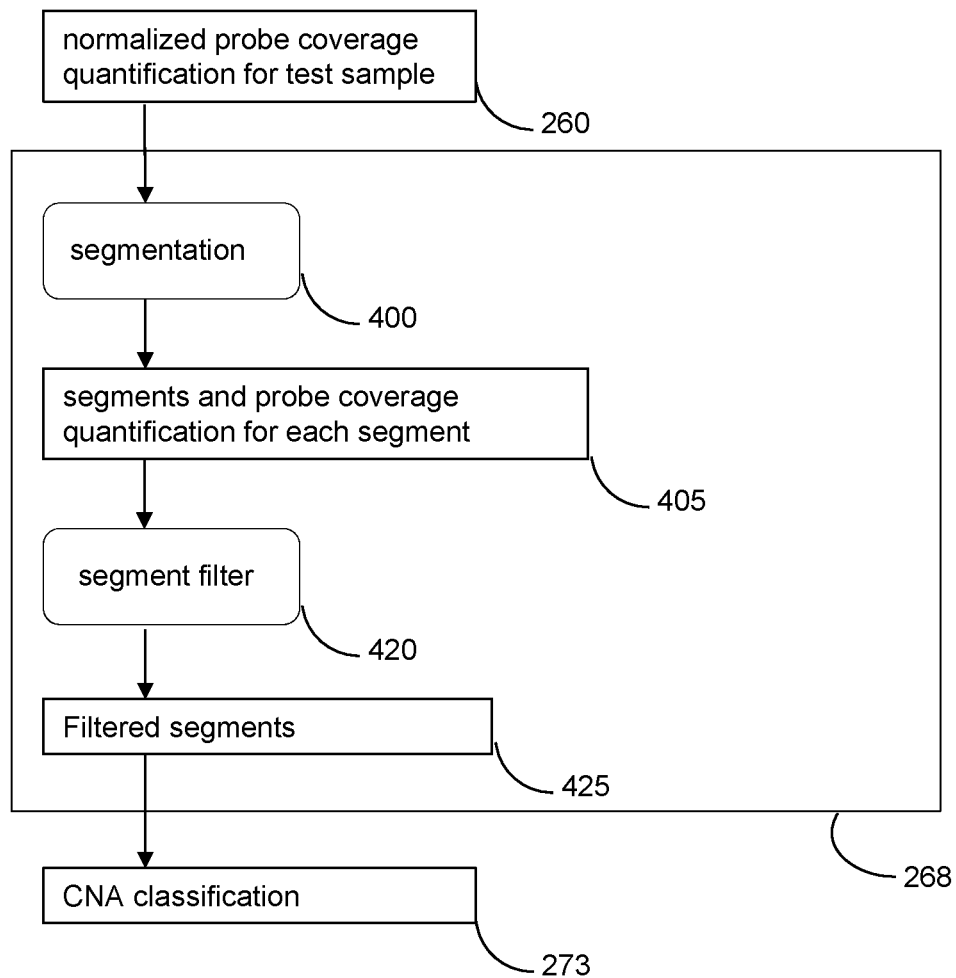
FIG. 12 shows a process flow in accordance with various embodiments.

Another embodiment for a CNA classification process is illustrated in FIG. 12. Normalized probe coverage quantifications for a test sample 260 are subjected to a copy number alteration (CNA) identifier and a CNA classification 273 is determined. One embodiment of a copy number alteration (CNA) identifier is illustrated as process 268 in FIG. 12. Normalized probe coverage quantifications for a test sample 260 are input for segmentation 400 which generates segments and probe coverage quantifications for each segment 405. Segments and probe coverage quantifications for each segment 405 are input for a segment filter 420, which generates filtered segments 425. CNA classification 273 may be determined according to the filtered segments 425.

Figure 13:
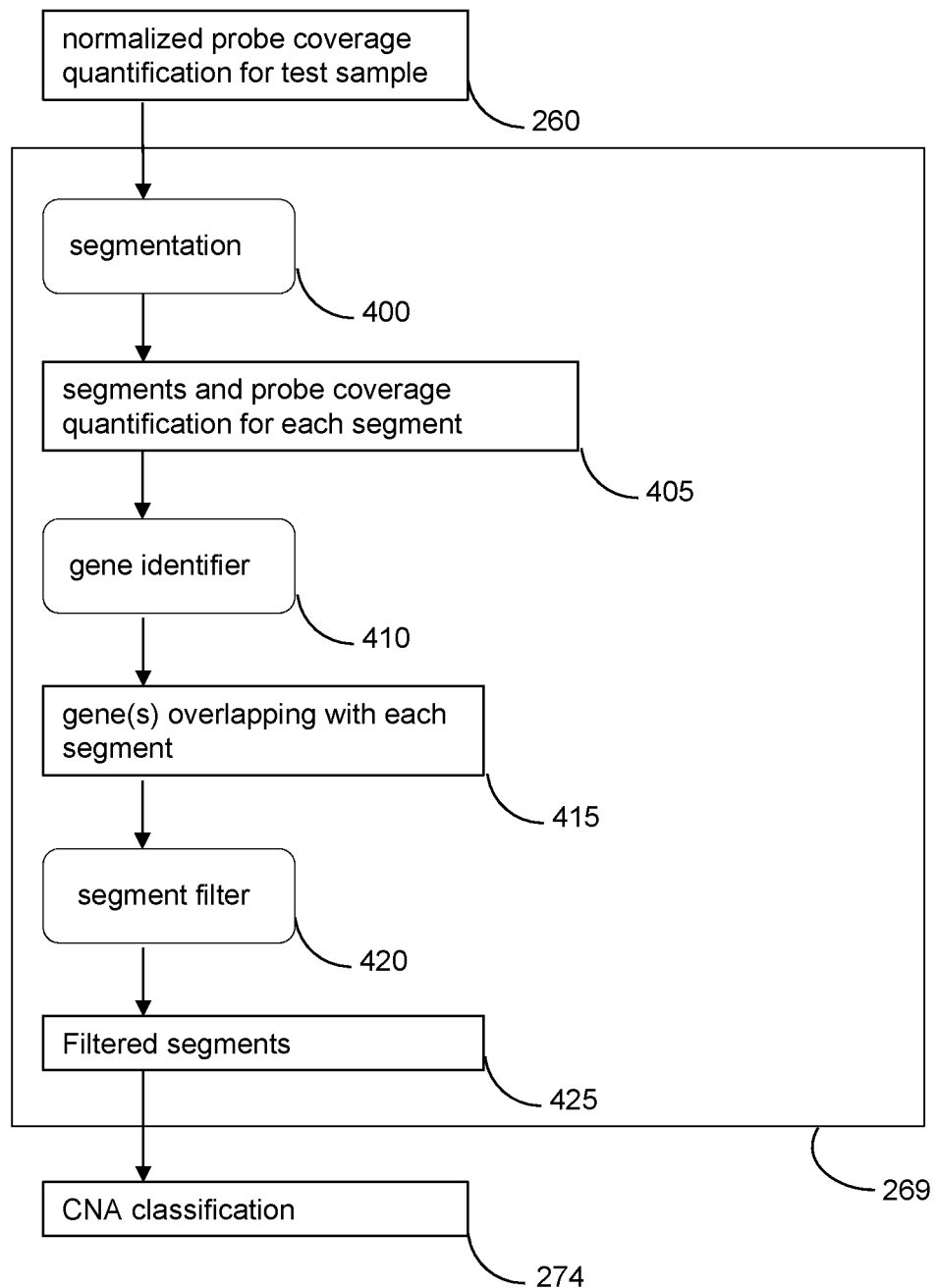
FIG. 13 shows a process flow in accordance with various embodiments.

Another embodiment for a CNA classification process is illustrated in FIG. 13. Normalized probe coverage quantifications for a test sample 260 are subjected to a copy number alteration (CNA) identifier and a CNA classification 274 is determined. One embodiment of a copy number alteration (CNA) identifier is illustrated as process 269 in FIG. 13. Normalized probe coverage quantifications for a test sample 260 are input for segmentation 400 which generates segments and probe coverage quantifications for each segment 405. Segments and probe coverage quantifications for each segment 405 are input for a gene identifier 410, which identifies gene(s) overlapping with each segment 415. Gene(s) overlapping with each segment 415 are input for a segment filter 420, which generates filtered segments 425. CNA classification 274 may be determined according to the filtered segments 425.

Samples

Provided herein are systems, methods and products for analyzing nucleic acids. In some embodiments, nucleic acid fragments in a mixture of nucleic acid fragments are analyzed. Nucleic acid fragments may be referred to as nucleic acid templates, and the terms may be used interchangeably herein. A mixture of nucleic acids can comprise two or more nucleic acid fragment species having the same or different nucleotide sequences, different fragment lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acid or a nucleic acid mixture utilized in systems, methods and products described herein often is isolated from a sample obtained from a subject (e.g., a test subject). A subject can be any living or non-living organism, including but not limited to a human, a non-human animal, a plant, a bacterium, a fungus, a protest or a pathogen. Any human or non-human animal can be selected, and may include, for example, mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. In some embodiments, a test subject is a female. In some embodiments, a test subject is a human female. In some embodiments, a test subject is a male. In some embodiments, a test subject is a human male.

Nucleic acid may be isolated from any type of suitable biological specimen or sample (e.g., a test sample). A sample or test sample can be any specimen that is isolated or obtained from a subject or part thereof (e.g., a human subject, a pregnant female, a cancer patient, a fetus, a tumor). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), urine, biopsy sample (e.g., liquid biopsy for the detection of cancer), a liquid sample described above, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

In some embodiments, a biological sample may be blood, plasma or serum. The term "blood" encompasses whole blood, blood product or any fraction of blood, such as serum, plasma, buffy coat, or the like as conventionally defined. Blood or fractions thereof often comprise nucleosomes. Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3 to 40 milliliters, between 5 to 50 milliliters) often is collected and can be stored according to standard procedures prior to or after preparation.

An analysis of nucleic acid found in a subjects blood may be performed using, e.g., whole blood, serum, or plasma. An analysis of fetal DNA found in maternal blood, for example, may be performed using, e.g., whole blood, serum, or plasma. An analysis of tumor DNA found in a patient's blood, for example, may be performed using, e.g., whole blood, serum, or plasma. Methods for preparing serum or plasma from blood obtained from a subject (e.g., a maternal subject; cancer patient) are known. For example, a subject's blood (e.g., a pregnant woman's blood; cancer patient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

A sample may be heterogeneous. For example, a sample may include more than one cell type and/or one or more nucleic acid species. In some instances, a sample may include (i) fetal cells and maternal cells, (ii) cancer cells and non-cancer cells, and/or (iii) pathogenic cells and host cells. In some instances, a sample may include (i) cancer and non-cancer nucleic acid, (ii) pathogen and host nucleic acid, (iii) fetal derived and maternal derived nucleic acid, and/or more generally, (iv) mutated and wild-type nucleic acid. In some instances, a sample may include a minority nucleic acid species and a majority nucleic acid species, as described in further detail below. In some instances, a sample may include cells and/or nucleic acid from a single subject or may include cells and/or nucleic acid from multiple subjects.

Cell Types

As used herein, a "cell type" refers to a type of cell that can be distinguished from another type of cell. Extracellular nucleic acid can include nucleic acid from several different cell types. Non-limiting examples of cell types that can contribute nucleic acid to circulating cell-free nucleic acid include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney/renal cells, heart cells, muscle cells, blood cells (e.g., white blood cells), central nervous system (CNS) cells, the like and combinations of the foregoing. In some embodiments, cell types that contribute nucleic acid to circulating cell-free nucleic acid analyzed include white blood cells, endothelial cells and hepatocyte liver cells. Different cell types can be screened as part of identifying and selecting nucleic acid loci for which a marker state is the same or substantially the same for a cell type in subjects having a medical condition and for the cell type in subjects not having the medical condition, as described in further detail herein.

A particular cell type sometimes remains the same or substantially the same in subjects having a medical condition and in subjects not having a medical condition. In a non-limiting example, the number of living or viable cells of a particular cell type may be reduced in a cell degenerative condition, and the living, viable cells are not modified, or are not modified significantly, in subjects having the medical condition.

A particular cell type sometimes is modified as part of a medical condition and has one or more different properties than in its original state. In a non-limiting example, a particular cell type may proliferate at a higher than normal rate, may transform into a cell having a different morphology, may transform into a cell that expresses one or more different cell surface markers and/or may become part of a tumor, as part of a cancer condition. In embodiments for which a particular cell type (i.e., a progenitor cell) is modified as part of a medical condition, the marker state for each of the one or more markers assayed often is the same or substantially the same for the particular cell type in subjects having the medical condition and for the particular cell type in subjects not having the medical condition. Thus, the term "cell type" sometimes pertains to a type of cell in subjects not having a medical condition, and to a modified version of the cell in subjects having the medical condition. In some embodiments, a "cell type" is a progenitor cell only and not a modified version arising from the progenitor cell. A "cell type" sometimes pertains to a progenitor cell and a modified cell arising from the progenitor cell. In such embodiments, a marker state for a marker analyzed often is the same or substantially the same for a cell type in subjects having a medical condition and for the cell type in subjects not having the medical condition.

In certain embodiments, a cell type is a cancer cell. Certain cancer cell types include, for example, leukemia cells (e.g., acute myeloid leukemia, acute lymphoblastic leukemia, chronic myeloid leukemia, chronic lymphoblastic leukemia); cancerous kidney/renal cells (e.g., renal cell cancer (clear cell, papillary type 1, papillary type 2, chromophobe, oncocytic, collecting duct), renal adenocarcinoma, hypernephroma, Wilm's tumor, transitional cell carcinoma); brain tumor cells (e.g., acoustic neuroma, astrocytoma (grade I: pilocytic astrocytoma, grade II: low-grade astrocytoma, grade III: anaplastic astrocytoma, grade IV: glioblastoma (GBM)), chordoma, cns lymphoma, craniopharyngioma, glioma (brain stem glioma, ependymoma, mixed glioma, optic nerve glioma, subependymoma), medulloblastoma, meningioma, metastatic brain tumors, oligodendroglioma, pituitary tumors, primitive neuroectodermal (PNET), schwannoma, juvenile pilocytic astrocytoma (JPA), pineal tumor, rhabdoid tumor).

Different cell types can be distinguished by any suitable characteristic, including without limitation, one or more different cell surface markers, one or more different morphological features, one or more different functions, one or more different protein (e.g., histone) modifications and one or more different nucleic acid markers. Non-limiting examples of nucleic acid markers include single-nucleotide polymorphisms (SNPs), methylation state of a nucleic acid locus, short tandem repeats, insertions (e.g., microinsertions), deletions (microdeletions) the like and combinations thereof. Non-limiting examples of protein (e.g., histone) modifications include acetylation, methylation, ubiquitylation, phosphorylation, sumoylation, the like and combinations thereof.

As used herein, the term a "related cell type" refers to a cell type having multiple characteristics in common with another cell type. In related cell types, 75% or more cell surface markers sometimes are common to the cell types (e.g., about 80%, 85%, 90% or 95% or more of cell surface markers are common to the related cell types).

Nucleic Acid

Provided herein are methods for analyzing nucleic acid. The terms "nucleic acid," "nucleic acid molecule," "nucleic acid fragment," and "nucleic acid template" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, bacterium, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain; and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be derived from one or more sources (e.g., biological sample, blood, cells, serum, plasma, buffy coat, urine, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as QIAGEN's QIAAMP Circulating Nucleic Acid Kit, QIAAMP DNA Mini Kit or QIAAMP DNA Blood Mini Kit (QIAGEN, Hilden, Germany), GenomicPrep™ Blood DNA Isolation Kit (Promega, Madison, Wis.), and GFX™ Genomic Blood DNA Purification Kit (Amersham, Piscataway, N.J.), the like or combinations thereof.

In some embodiments, nucleic acid is extracted from cells using a cell lysis procedure. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. In some instances, a high salt and/or an alkaline lysis procedure may be utilized.

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments, ccf DNA) and/or "cell-free circulating nucleic acid." Extracellular nucleic acid can be present in and obtained from blood (e.g., from the blood of a human subject). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample.

Without being limited by theory, extracellular nucleic acid may be a product of cell apoptosis and cell breakdown, which provides basis for extracellular nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject.

Extracellular nucleic acid can include different nucleic acid species, and therefore is referred to herein as "heterogeneous" in certain embodiments. For example, blood serum or plasma from a person having cancer can include nucleic acid from cancer cells (e.g., tumor, neoplasia) and nucleic acid from non-cancer cells. In another example, blood serum or plasma from a pregnant female can include maternal nucleic acid and fetal nucleic acid. In some instances, cancer or fetal nucleic acid sometimes is about 5% to about 50% of the overall nucleic acid (e.g., about 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer or fetal nucleic acid).

At least two different nucleic acid species can exist in different amounts in extracellular nucleic acid and sometimes are referred to as minority species and majority species. In certain instances, a minority species of nucleic acid is from an affected cell type (e.g., cancer cell, wasting cell, cell attacked by immune system). In certain embodiments, a genetic variation or genetic alteration (e.g., copy number alteration, copy number variation, single nucleotide alteration, single nucleotide variation, chromosome alteration, and/or translocation) is determined for a minority nucleic acid species. In certain embodiments, a genetic variation or genetic alteration is determined for a majority nucleic acid species. Generally it is not intended that the terms "minority" or "majority" be rigidly defined in any respect. In one aspect, a nucleic acid that is considered "minority," for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40% of the overall nucleic acid (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue affected by a cell proliferative disorder. In some embodiments, the minority nucleic acid is extracellular DNA from a tumor cell. In some embodiments, the minority nucleic acid is extracellular fetal DNA.

In another aspect, a nucleic acid that is considered "majority," for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 250 base pairs or less (e.g., about 80, 85, 90, 91, 92, 93, 94, 95, 96, 97, 98, 99 or 100% of minority species nucleic acid is of a length of about 250 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, a minority species of extracellular nucleic acid is of a length of about 100 base pairs or less (e.g., about 80, 90, 91, 92, 93, 94, 95, 96, 97, 98, 99 or 100% of minority species nucleic acid is of a length of about 100 base pairs or less). In some embodiments, a minority species of extracellular nucleic acid is of a length of about 50 base pairs or less (e.g., about 80, 85, 90, 91, 92, 93, 94, 95, 96, 97, 98, 99 or 100% of minority species nucleic acid is of a length of about 50 base pairs or less).

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of fetal nucleic acid (e.g., to 500 bp fragments) can be purified, or partially purified, from a mixture comprising both fetal and maternal nucleic acid fragments. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

In some embodiments nucleic acids, such as, for example, cellular nucleic acids, are sheared or cleaved prior to, during or after a method described herein. The term "shearing" or "cleavage" generally refers to a procedure or conditions in which a nucleic acid molecule, such as a nucleic acid template gene molecule or amplified product thereof, may be severed into two (or more) smaller nucleic acid molecules. Such shearing or cleavage can be sequence specific, base specific, or nonspecific, and can be accomplished by any of a variety of methods, reagents or conditions, including, for example, chemical, enzymatic, physical shearing (e.g., physical fragmentation). Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

Sheared or cleaved nucleic acids can be generated by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 2005/0112590, the like or combinations thereof. The average, mean or nominal length of the resulting nucleic acid fragments can be controlled by selecting an appropriate fragment-generating method.

The term "amplified" as used herein refers to subjecting a target nucleic acid in a sample to a process that linearly or exponentially generates amplicon nucleic acids having the same or substantially the same nucleotide sequence as the target nucleic acid, or part thereof. In certain embodiments the term "amplified" refers to a method that comprises a polymerase chain reaction (PCR). In certain instances, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a sequence analysis.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, cancer nucleic acid, patient nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, cancer or fetal nucleic acid. In certain embodiments, a method for determining fraction of cancer cell nucleic acid or fetal fraction also can be used to enrich for cancer or fetal nucleic acid. In certain embodiments, nucleic acid from normal tissue (e.g., non-cancer cells) is selectively removed (partially, substantially, almost completely or completely) from the sample. In certain embodiments, maternal nucleic acid is selectively removed (partially, substantially, almost completely or completely) from the sample. In certain embodiments, enriching for a particular low copy number species nucleic acid (e.g., cancer or fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, the entire content of each is incorporated herein by reference, including all text, tables, equations and drawings.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art.

Non-limiting examples of methods for enriching for a nucleic acid subpopulation in a sample include methods that exploit epigenetic differences between nucleic acid species (e.g., methylation-based fetal nucleic acid enrichment methods described in U.S. Patent Application Publication No. 2010/0105049, which is incorporated by reference herein); restriction endonuclease enhanced polymorphic sequence approaches (e.g., such as a method described in U.S. Patent Application Publication No. 2009/0317818, which is incorporated by reference herein); selective enzymatic degradation approaches; massively parallel signature sequencing (MPSS) approaches; amplification (e.g., PCR)-based approaches (e.g., loci-specific amplification methods, multiplex SNP allele PCR approaches; universal amplification methods); pull-down approaches (e.g., biotinylated ultramer pull-down methods); extension and ligation-based methods (e.g., molecular inversion probe (MIP) extension and ligation); and combinations thereof.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from a nucleic acid sample. Commercially available nucleic acid capture systems include, for example, NIMBLEGEN sequence capture system (ROCHE NIMBLEGEN, Madison, WI); ILLUMINA BEADARRAY platform (ILLUMINA, San Diego, CA); AFFYMETRIX GENECHIP platform (AFFYMETRIX, Santa Clara, CA); AGILENT SURESELECT Target Enrichment System (AGILENT Technologies, Santa Clara, CA); and related platforms. Such methods typically involve hybridization of a capture oligonucleotide to a part or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest), genes or regions of interest thereof. Thus, in some embodiments, a nucleic acid sample is optionally enriched by capturing a subset of fragments using capture oligonucleotides complementary to, for example, selected genes in sample nucleic acid. An example selective nucleic acid capture process is described in further detail herein and in the Examples. In certain instances, captured fragments are amplified. For example, captured fragments containing adapters may be amplified using primers complementary to the adapter oligonucleotides to form collections of amplified fragments, indexed according to adapter sequence. Indexing according to adapter sequence is described in further detail herein. In some embodiments, nucleic acid is enriched for fragments from a select genomic region (e.g., chromosome, a gene) by amplification of one or more regions of interest using oligonucleotides (e.g., PCR primers) complementary to sequences in fragments containing the region(s) of interest, or part(s) thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain instances, length-based separation approaches can include selective sequence tagging approaches, fragment circularization, chemical treatment (e.g., formaldehyde, polyethylene glycol (PEG) precipitation), mass spectrometry and/or size-specific nucleic acid amplification, for example.

Nucleic Acid Quantification

The amount of nucleic acid (e.g., concentration, relative amount, absolute amount, copy number, and the like) in a sample may be determined. The amount of a minority nucleic acid (e.g., concentration, relative amount, absolute amount, copy number, and the like) in nucleic acid is determined in some embodiments. In certain embodiments, the amount of a minority nucleic acid species in a sample is referred to as "minority species fraction." In some embodiments "minority species fraction" refers to the fraction of a minority nucleic acid species in circulating cell-free nucleic acid in a sample (e.g., a blood sample, a serum sample, a plasma sample, a urine sample) obtained from a subject.

The amount of a minority nucleic acid in extracellular nucleic acid can be quantified and used in conjunction with a method provided herein. Thus, in certain embodiments, methods described herein comprise an additional step of determining the amount of a minority nucleic acid. The amount of a minority nucleic acid can be determined in a sample from a subject before or after processing to prepare sample nucleic acid. In certain embodiments, the amount of a minority nucleic acid is determined in a sample after sample nucleic acid is processed and prepared, which amount is utilized for further assessment. In some embodiments, an outcome comprises factoring the minority species fraction in the sample nucleic acid (e.g., adjusting counts, removing samples, making a call or not making a call).

A determination of minority species fraction can be performed before, during, or at any one point in a method described herein, or after certain methods described herein (e.g., detection of a genetic variation or genetic alteration). For example, to conduct a genetic variation/genetic alteration determination method with a certain sensitivity or specificity, a minority nucleic acid quantification method may be implemented prior to, during or after genetic variation/genetic alteration determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more minority nucleic acid. In some embodiments, samples determined as having a certain threshold amount of minority nucleic acid (e.g., about 15% or more minority nucleic acid; about 4% or more minority nucleic acid) are further analyzed for a genetic variation/genetic alteration, or the presence or absence of a genetic variation/genetic alteration, for example. In certain embodiments, determinations of, for example, a genetic variation or genetic alteration are selected (e.g., selected and communicated to a patient) only for samples having a certain threshold amount of a minority nucleic acid (e.g., about 15% or more minority nucleic acid; about 4% or more minority nucleic acid).

The amount of cancer cell nucleic acid (e.g., concentration, relative amount, absolute amount, copy number, and the like) in nucleic acid is determined in some embodiments. In certain instances, the amount of cancer cell nucleic acid in a sample is referred to as "fraction of cancer cell nucleic acid," and sometimes is referred to as "cancer fraction" or "tumor fraction." In some embodiments "fraction of cancer cell nucleic acid" refers to the fraction of cancer cell nucleic acid in circulating cell-free nucleic acid in a sample (e.g., a blood sample, a serum sample, a plasma sample, a urine sample) obtained from a subject.

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction." In some embodiments "fetal fraction" refers to the fraction of fetal nucleic acid in circulating cell-free nucleic acid in a sample (e.g., a blood sample, a serum sample, a plasma sample, a urine sample) obtained from a pregnant female. Certain methods described herein or known in the art for determining fetal fraction can be used for determining a fraction of cancer cell nucleic acid and/or a minority species fraction.

In certain instances, fetal fraction may be determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation) between mother and fetus, or fetal RNA markers in maternal blood plasma (see e.g., Lo, 2005, Journal of Histochemistry and Cytochemistry 53 (3): 293-296)). Determination of fetal fraction sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample.

In certain embodiments, a minority species fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method for determining fetal fraction, for example, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome.

A minority species fraction can be determined, in some embodiments, using methods that incorporate information derived from chromosomal aberrations as described, for example, in International Patent Application Publication No. WO2014/055774, which is incorporated by reference herein. A minority species fraction can be determined, in some embodiments, using methods that incorporate information derived from sex chromosomes as described, for example, in U.S. Patent Application Publication No. 2013/0288244 and U.S. Patent Application Publication No. 2013/0338933, each of which is incorporated by reference herein.

A minority species fraction can be determined in some embodiments using methods that incorporate fragment length information (e.g., fragment length ratio (FLR) analysis, fetal ratio statistic (FRS) analysis as described in International Patent Application Publication No. WO2013/177086, which is incorporated by reference herein). Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts, for example, to counts from fragments over a particular length threshold and/or to the amount of total nucleic acid in the sample. Methods for counting nucleic acid fragments of a particular length are described in further detail in International Patent Application Publication No. WO2013/177086.

A minority species fraction can be determined, in some embodiments, according to portion-specific fraction estimates (e.g., as described in International Patent Application Publication No. WO 2014/205401, which is incorporated by reference herein). Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus). Portion-specific fetal fraction estimates generally are determined according to portion-specific parameters and their relation to fetal fraction.

In some embodiments, the determination of minority species fraction (e.g., fraction of cancer cell nucleic acid; fetal fraction) is not required or necessary for identifying the presence or absence of a genetic variation or genetic alteration. In some embodiments, identifying the presence or absence of a genetic variation or genetic alteration does not require a sequence differentiation of a minority nucleic acid versus a majority nucleic acid. In certain embodiments, this is because the summed contribution of both minority and majority sequences in a particular chromosome, chromosome portion or part thereof is analyzed. In some embodiments, identifying the presence or absence of a genetic variation or genetic alteration does not rely on a priori sequence information that would distinguish minority nucleic acid from majority nucleic acid.

Nucleic Acid Library

In some embodiments a nucleic acid library is a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments, a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adapters. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments, a polynucleotide of known sequence comprises a universal sequence. A universal sequence is a specific nucleotide sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using cell-free DNA).

In certain embodiments, a ligation-based library preparation method is used (e.g., ILLUMINA TRUSEQ, ILLUMINA, San Diego CA). Ligation-based library preparation methods often make use of an adapter (e.g., a methylated adapter) design which can incorporate an index sequence at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides.

In some embodiments nucleic acid library preparation comprises ligating an adapter oligonucleotide (e.g., to a sample nucleic acid, to a sample nucleic acid fragment, to a template nucleic acid). Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). In some embodiments, an adapter oligonucleotide comprises one or more of primer annealing polynucleotide (e.g., for annealing to flow cell attached oligonucleotides and/or to free amplification primers), an index polynucleotide (e.g., sample index sequence for tracking nucleic acid from different samples; also referred to as a sample ID), and a barcode polynucleotide (e.g., single molecule barcode (SMB) for tracking individual molecules of sample nucleic acid that are amplified prior to sequencing; also referred to as a molecular barcode). In some embodiments, a primer annealing component of an adapter oligonucleotide comprises one or more universal sequences (e.g., sequences complementary to one or more universal amplification primers). In some embodiments, an index polynucleotide (e.g., sample index; sample ID) is a component of an adapter oligonucleotide. In some embodiments, an index polynucleotide (e.g., sample index; sample ID) is a component of a universal amplification primer sequence.

In some embodiments, adapter oligonucleotides when used in combination with amplification primers (e.g., universal amplification primers) are designed generate library constructs comprising one or more of: universal sequences, molecular barcodes, sample ID sequences, spacer sequences, and a sample nucleic acid sequence. In some embodiments, adapter oligonucleotides when used in combination with universal amplification primers are designed generate library constructs comprising an ordered combination of one or more of: universal sequences, molecular barcodes, sample ID sequences, spacer sequences, and a sample nucleic acid sequence. For example, a library construct may comprise a first universal sequence, followed by a second universal sequence, followed by first molecular barcode, followed by a spacer sequence, followed by a template sequence (e.g., sample nucleic acid sequence), followed by a spacer sequence, followed by a second molecular barcode, followed by a third universal sequence, followed by a sample ID, followed by a fourth universal sequence. In some embodiments, adapter oligonucleotides when used in combination with amplification primers (e.g., universal amplification primers) are designed generate library constructs for each strand of a template molecule (e.g., sample nucleic acid molecule). In some embodiments, adapter oligonucleotides are duplex adapter oligonucleotides, such as, for example, duplex adapters shown in FIG. 20A to FIG. 20D.

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, EPICENTRE, Madison, WI). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support. In some embodiments, modified nucleic acid (e.g., nucleic acid modified by addition of adapters) is amplified.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WILDFIRE-amplification (e.g., U.S. Patent Application Publication No. 2013/0012399), the like or combinations thereof.

Nucleic Acid Capture

In some embodiments, a sample nucleic acid (or a sample nucleic acid library) is subjected to a target capture process. Generally a target capture process is performed by contacting sample nucleic acid (or a sample nucleic acid library) with a set of probe oligonucleotides under hybridization conditions. A set of probe oligonucleotides (e.g., capture oligonucleotides) generally includes a plurality of probe oligonucleotides having sequences that are complementary to, or substantially complementary to, sequences in sample nucleic acid. A plurality of probe oligonucleotides may include about 10 probe oligonucleotide species, about 50 probe oligonucleotide species, about 100 probe oligonucleotide species, about 500 probe oligonucleotide species, about 1,000 probe oligonucleotide species, 2,000 probe oligonucleotide species, 3,000 probe oligonucleotide species, 4,000 probe oligonucleotide species, 5000 probe oligonucleotide species, 10,000 probe oligonucleotide species, or more. Generally, a first probe oligonucleotide species has a different nucleotide sequence than a second probe oligonucleotide species, and different species of probe oligonucleotides in a set each have a different nucleotide sequence.

A probe oligonucleotide typically comprises a nucleotide sequence capable of hybridizing or annealing to a nucleic acid fragment of interest (e.g. target fragment) or a portion thereof. A probe oligonucleotide may be naturally occurring or synthetic and may be DNA or RNA based. Probe oligonucleotides can allow for specific separation of, for example, a target fragment away from other fragments in a nucleic acid sample. The term "specific" or "specificity," as used herein, refers to the binding or hybridization of one molecule to another molecule, such as an oligonucleotide for a target polynucleotide. "Specific" or "specificity" refers to the recognition, contact, and formation of a stable complex between two molecules, as compared to substantially less recognition, contact, or complex formation of either of those two molecules with other molecules. As used herein, the terms "anneal" and "hybridize" refer to the formation of a stable complex between two molecules. The terms "probe," probe oligonucleotide," "capture probe," "capture oligonucleotide," "capture oligo," "oligo," or "oligonucleotide" may be used interchangeably throughout the document, when referring to probe oligonucleotides.

A probe oligonucleotide can be designed and synthesized using a suitable process, and may be of any length suitable for hybridizing to a nucleotide sequence of interest and performing separation and/or analysis processes described herein. Oligonucleotides may be designed based upon a nucleotide sequence of interest (e.g., target fragment sequence, genomic sequence, gene sequence). An oligonucleotide (e.g., a probe oligonucleotide), in some embodiments, may be about 10 to about 300 nucleotides, about 50 to about 200 nucleotides, about 75 to about 150 nucleotides, about 110 to about 130 nucleotides, or about 111, 112, 113, 114, 115, 116, 117, 118, 119, 120, 121, 122, 123, 124, 125, 126, 127, 128, or 129 nucleotides in length. An oligonucleotide may be composed of naturally occurring and/or non-naturally occurring nucleotides (e.g., labeled nucleotides), or a mixture thereof. Oligonucleotides suitable for use with embodiments described herein, may be synthesized and labeled using known techniques. Oligonucleotides may be chemically synthesized according to the solid phase phosphoramidite triester method first described by Beaucage and Caruthers (1981) Tetrahedron Letts. 22:1859-1862, using an automated synthesizer, and/or as described in Needham-VanDevanter et al. (1984) Nucleic Acids Res. 12:6159-6168. Purification of oligonucleotides can be effected by native acrylamide gel electrophoresis or by anion-exchange high-performance liquid chromatography (HPLC), for example, as described in Pearson and Regnier (1983) J. Chrom. 255:137-149.

All or a portion of a probe oligonucleotide sequence (naturally occurring or synthetic) may be substantially complementary to a target sequence or portion thereof, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and oligonucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Probe oligonucleotides that are substantially complimentary to a nucleotide sequence of interest (e.g., target sequence) or portion thereof are also substantially similar to the compliment of the target sequence or relevant portion thereof (e.g., substantially similar to the anti-sense strand of the nucleic acid). One test for determining whether two nucleotide sequences are substantially similar is to determine the percent of identical nucleotide sequences shared. As referred to herein, "substantially similar" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other.

Hybridization conditions (e.g., annealing conditions) can be determined and/or adjusted, depending on the characteristics of the oligonucleotides used in an assay. Oligonucleotide sequence and/or length sometimes may affect hybridization to a nucleic acid sequence of interest. Depending on the degree of mismatch between an oligonucleotide and nucleic acid of interest, low, medium or high stringency conditions may be used to effect the annealing. As used herein, the term "stringent conditions" refers to conditions for hybridization and washing. Methods for hybridization reaction temperature condition optimization are known in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

In some embodiments, one or more probe oligonucleotides are associated with an affinity ligand such as a member of a binding pair (e.g., biotin) or antigen that can bind to a capture agent such as avidin, streptavidin, an antibody, or a receptor. For example, a probe oligonucleotide may be biotinylated such that it can be captured onto a streptavidin-coated bead.

In some embodiments, one or more probe oligonucleotides and/or capture agents are effectively linked to a solid support or substrate. A solid support or substrate can be any physically separable solid to which a probe oligonucleotide can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). The probe oligonucleotides may be linked to the solid support by covalent bonds or by non-covalent interactions and may be linked to the solid support directly or indirectly (e.g., via an intermediary agent such as a spacer molecule or biotin). A probe oligonucleotide may be linked to the solid support before, during or after nucleic acid capture.

Nucleic acid that has been modified, such as modified by the addition of adapter sequences described herein, may be captured. In some embodiments, unmodified nucleic acid is captured. Nucleic acid may be amplified before and/or after capture, in some embodiments, by an amplification process such as PCR. The term "captured nucleic acid" generally includes nucleic acid that has been captured and includes nucleic acid that has been captured and amplified. Captured nucleic acid may be subjected to additional rounds of capture and amplification, in some embodiments. Captured nucleic acid may be sequenced, such as by a sequencing process described herein.

Figure 2:
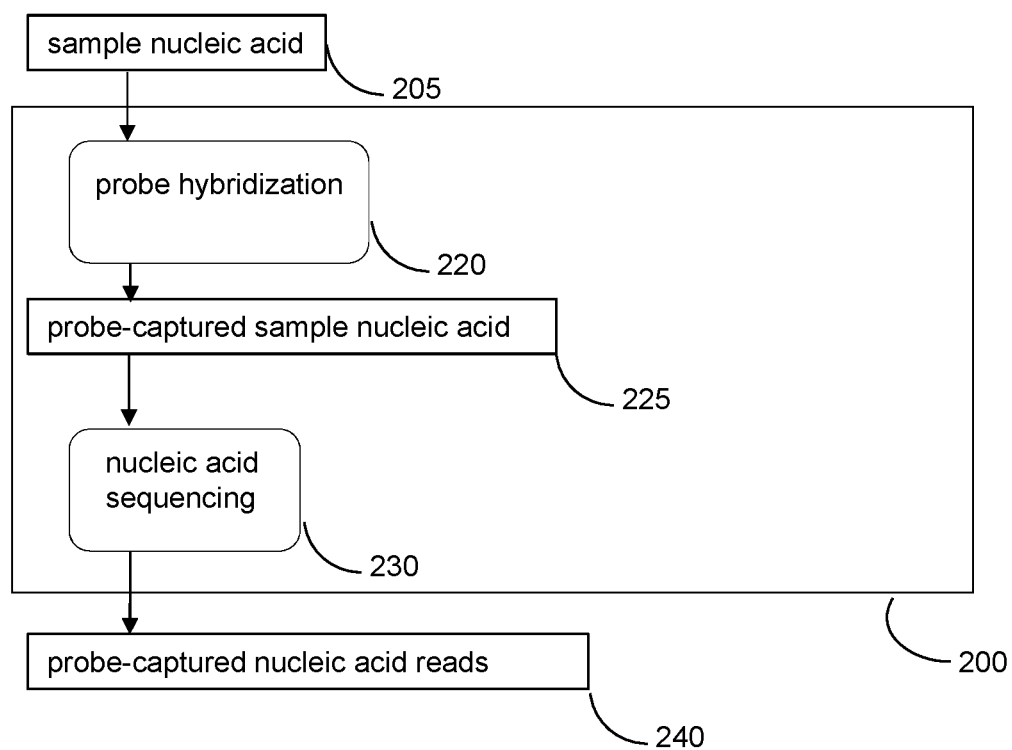
FIG. 2 shows a process flow in accordance with various embodiments.

An embodiment of a nucleic acid target capture process is illustrated in FIG. 2. Sample nucleic acid 205 is subjected a nucleic acid capture process which generates probe-captured nucleic acid sequence reads 240. One embodiment of a nucleic acid capture process is illustrated as process 200. Sample nucleic acid 205 is subjected to probe hybridization 220 which generates probe-captured sample nucleic acid 225. Probe-captured sample nucleic acid 225 is subjected to nucleic acid sequencing 230 which generates probe-captured nucleic acid sequence reads 240.

Nucleic Acid Sequencing and Processing

Methods provided herein generally include nucleic acid sequencing and analysis. In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering portions, selecting portions, counting, normalizing, weighting, generating a profile, and the like, and combinations thereof. Certain processing steps may be performed in any order and certain processing steps may be repeated. For example, portions may be filtered followed by sequence read count normalization, and, in certain embodiments, sequence read counts may be normalized followed by portion filtering. In some embodiments, a portion filtering step is followed by sequence read count normalization followed by a further portion filtering step. Certain sequencing methods and processing steps are described in further detail below.

Sequencing

In some embodiments, nucleic acid (e.g., nucleic acid fragments, sample nucleic acid, cell-free nucleic acid) is sequenced. In certain instances, a full or substantially full sequence is obtained and sometimes a partial sequence is obtained. Nucleic acid sequencing generally produces a collection of sequence reads. As used herein, "reads" (e.g., "a read," "a sequence read") are short nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. In some embodiments sequence reads are of a mean, median, average or absolute length of about 1500, 2000, 2500, 3000, 3500, 4000, 4500, or 5000 bp or more. In some embodiments, sequence reads are of a mean, median, average or absolute length of about 100 bp to about 200 bp. In some embodiments, sequence reads are of a mean, median, average or absolute length of about 140 bp to about 160 bp. For example, sequence reads may be of a mean, median, average or absolute length of about 140, 141, 142, 143, 144, 145, 146, 147, 148, 149, 150, 151, 152, 153, 154, 155, 156, 157, 158, 159 or 160 bp.

In some embodiments the nominal, average, mean or absolute length of single-end reads sometimes is about 10 continuous nucleotides to about 250 or more contiguous nucleotides, about 15 contiguous nucleotides to about 200 or more contiguous nucleotides, about 15 contiguous nucleotides to about 150 or more contiguous nucleotides, about 15 contiguous nucleotides to about 125 or more contiguous nucleotides, about 15 contiguous nucleotides to about 100 or more contiguous nucleotides, about 15 contiguous nucleotides to about 75 or more contiguous nucleotides, about 15 contiguous nucleotides to about 60 or more contiguous nucleotides, 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length. In certain embodiments the nominal, average, mean or absolute length of single-end reads is about 20 to about 200 bases, about 100 to about 200 bases, or about 140 to about 160 bases in length. In certain embodiments the nominal, average, mean or absolute length of single-end reads is about 40, 50, 60, 70, 80, 90, 100, 110, 120, 130, 140, 150, 160, 170, 180, 190, or about 200 bases or more in length. In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides. In certain embodiments, the nominal, average, mean or absolute length of paired-end reads sometimes is about 25 contiguous nucleotides to about 400 contiguous nucleotides or more (e.g., about 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nucleotides in length or more), about 50 contiguous nucleotides to about 350 contiguous nucleotides or more, about 100 contiguous nucleotides to about 325 contiguous nucleotides, about 150 contiguous nucleotides to about 325 contiguous nucleotides, about 200 contiguous nucleotides to about 325 contiguous nucleotides, about 275 contiguous nucleotides to about 310 contiguous nucleotides, about 100 contiguous nucleotides to about 200 contiguous nucleotides, about 100 contiguous nucleotides to about 175 contiguous nucleotides, about 125 contiguous nucleotides to about 175 contiguous nucleotides, and sometimes is about 140 contiguous nucleotides to about 160 contiguous nucleotides. In certain embodiments, the nominal, average, mean, or absolute length of paired-end reads is about 150 contiguous nucleotides, and sometimes is 150 contiguous nucleotides.

In some embodiments, nucleotide sequence reads obtained from a sample are partial nucleotide sequence reads. As used herein, "partial nucleotide sequence reads" refers to sequence reads of any length with incomplete sequence information, also referred to as sequence ambiguity. Partial nucleotide sequence reads may lack information regarding nucleobase identity and/or nucleobase position or order. Partial nucleotide sequence reads generally do not include sequence reads in which the only incomplete sequence information (or in which less than all of the bases are sequenced or determined) is from inadvertent or unintentional sequencing errors. Such sequencing errors can be inherent to certain sequencing processes and include, for example, incorrect calls for nucleobase identity, and missing or extra nucleobases. Thus, for partial nucleotide sequence reads herein, certain information about the sequence is often deliberately excluded. That is, one deliberately obtains sequence information with respect to less than all of the nucleobases or which might otherwise be characterized as or be a sequencing error. In some embodiments, a partial nucleotide sequence read can span a portion of a nucleic acid fragment. In some embodiments, a partial nucleotide sequence read can span the entire length of a nucleic acid fragment. Partial nucleotide sequence reads are described, for example, in International Patent Application Publication No. WO2013/052907, the entire content of which is incorporated herein by reference, including all text, tables, equations and drawings.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. A mixture of relatively short reads can be transformed by processes described herein into a representation of genomic nucleic acid present in the subject, and/or a representation of genomic nucleic acid present in a tumor or a fetus. In certain instances, a mixture of relatively short reads can be transformed into a representation of a copy number alteration, a genetic variation/genetic alteration or an aneuploidy, for example. In one example, reads of a mixture of cancer and non-cancer nucleic acid can be transformed into a representation of a composite chromosome or a part thereof comprising features of one or both cancer cell and non-cancer cell chromosomes. In another example, reads of a mixture of maternal and fetal nucleic acid can be transformed into a representation of a composite chromosome or a part thereof comprising features of one or both maternal and fetal chromosomes.

In some instances, circulating cell free nucleic acid fragments (CCF fragments) obtained from a cancer patient comprise nucleic acid fragments originating from normal cells (i.e., non-cancer fragments) and nucleic acid fragments originating from cancer cells (i.e., cancer fragments). Sequence reads derived from CCF fragments originating from normal cells (i.e., non-cancerous cells) are referred to herein as "non-cancer reads." Sequence reads derived from CCF fragments originating from cancer cells are referred to herein as "cancer reads." CCF fragments from which non-cancer reads are obtained may be referred to herein as non-cancer templates and CCF fragments from which cancer reads are obtained may be referred herein to as cancer templates.

In some instances, circulating cell free nucleic acid fragments (CCF fragments) obtained from a pregnant female comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, e.g., by a PCR based method) prior to or during sequencing. In certain embodiments specific nucleic acid species or subsets in a sample are enriched and/or amplified prior to or during sequencing. In some embodiments, a species or subset of a pre-selected pool of nucleic acids is sequenced randomly. In some embodiments, nucleic acids in a sample are not enriched and/or amplified prior to or during sequencing.

In some embodiments, a representative fraction of a genome is sequenced and is sometimes referred to as "coverage" or "fold coverage." For example, a 1-fold coverage indicates that roughly 100% of the nucleotide sequences of the genome are represented by reads. In some instances, fold coverage is referred to as (and is directly proportional to) "sequencing depth." In some embodiments, "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage). In some embodiments, a genome (e.g., a whole genome) is sequenced with about 0.01-fold to about 100-fold coverage, about 0.1-fold to coverage, or about 0.1-fold to about 1-fold coverage (e.g., about 0.015-, 0.02-, 0.03-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold or greater coverage). In some embodiments, specific parts of a genome (e.g., genomic parts from targeted and/or probe-based methods) are sequenced and fold coverage values generally refer to the fraction of the specific genomic parts sequenced (i.e., fold coverage values do not refer to the whole genome). In some instances, specific genomic parts are sequenced at 1000-fold coverage or more. For example, specific genomic parts may be sequenced at 2000-fold, 5,000-fold, 10,000-fold, 20,000-fold, 30,000-fold, 40,000-fold or 50,000-fold coverage. In some embodiments, sequencing is at about 1,000-fold to about 100,000-fold coverage. In some embodiments, sequencing is at about 10,000-fold to about 70,000-fold coverage. In some embodiments, sequencing is at about 20,000-fold to about 60,000-fold coverage. In some embodiments, sequencing is at about 30,000-fold to about 50,000-fold coverage.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments, a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include ILLUMINA's multiplexing sample preparation oligonucleotide kit and multiplexing sequencing primers and PHIX control kit (e.g., ILLUMINA's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., ILLUMINA's Genome Analyzer; Genome Analyzer II; HISEQ 2000; HISEQ 2500 (ILLUMINA, San Diego CA)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include ILLUMINA/SOLEX/HISEQ (e.g., ILLUMINA's Genome Analyzer; Genome Analyzer II; HISEQ 2000; HISEQ), SOLID, ROCHE/454, PACBIO and/or SMRT, HELICOS True Single Molecule Sequencing (TSMS), ION TORRENT and ION semiconductor-based sequencing (e.g., as developed by Life Technologies), WILDFIRE, 5500, 5500xl W and/or 5500xl W Genetic Analyzer based technologies (e.g., as developed and sold by Life Technologies, U.S. Patent Application Publication No. 2013/0012399); POLONY sequencing, PYROSEQUENCING, Massively Parallel Signature Sequencing (MPSS), RNA polymerase (RNAP) sequencing, LASERGEN_systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In some embodiments, sequence reads are generated, obtained, gathered, assembled, manipulated, transformed, processed, and/or provided by a sequence module. A machine comprising a sequence module can be a suitable machine and/or apparatus that determines the sequence of a nucleic acid utilizing a sequencing technology known in the art. In some embodiments a sequence module can align, assemble, fragment, complement, reverse complement, and/or error check (e.g., error correct sequence reads).

Mapping Reads

Sequence reads can be mapped and the number of reads mapping to a specified nucleic acid region (e.g., a chromosome or portion thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions, which are discussed in further detail below.

The terms "aligned," "alignment," or "aligning" generally refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the ILLUMINA Genomics Analysis pipeline.

Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, mappability is assessed for a genomic region (e.g., portion, genomic portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Portions

In some embodiments, mapped sequence reads are grouped together according to various parameters and assigned to particular genomic portions (e.g., portions of a reference genome). A "portion" also may be referred to herein as a "genomic section," "bin," "partition," "portion of a reference genome," "portion of a chromosome" or "genomic portion."

A portion often is defined by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

Partitioning sometimes is based on, or is based in part on, certain informational features, such as, information content and information gain, for example. Non-limiting examples of certain informational features include speed and/or convenience of alignment, sequencing coverage variability, GC content (e.g., stratified GC content, particular GC contents, high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features. In some embodiments, information content may be quantified using a p-value profile measuring the significance of particular genomic locations for distinguishing between groups of confirmed normal and abnormal subjects (e.g. euploid and trisomy subjects, respectively).

In some embodiments, partitioning a genome may eliminate similar regions (e.g., identical or homologous regions or sequences) across a genome and only keep unique regions. Regions removed during partitioning may be within a single chromosome, may be one or more chromosomes, or may span multiple chromosomes. In some embodiments, a partitioned genome is reduced and optimized for faster alignment, often focusing on uniquely identifiable sequences.

In some embodiments, genomic portions result from a partitioning based on non-overlapping fixed size, which results in consecutive, non-overlapping portions of fixed length. Such portions often are shorter than a chromosome and often are shorter than a copy number variation (or copy number alteration) region (e.g., a region that is duplicated or is deleted), the latter of which can be referred to as a segment. A "segment" or "genomic segment" often includes two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)).

Multiple portions sometimes are analyzed in groups, and sometimes reads mapped to portions are quantified according to a particular group of genomic portions. Where portions are partitioned by structural features and correspond to regions in a genome, portions sometimes are grouped into one or more segments and/or one or more regions. Non-limiting examples of regions include sub-chromosome (i.e., shorter than a chromosome), chromosome, autosome, sex chromosome and combinations thereof. One or more sub-chromosome regions sometimes are genes, gene fragments, regulatory sequences, introns, exons, segments (e.g., a segment spanning a copy number alteration region), microduplications, microdeletions and the like. A region sometimes is smaller than a chromosome of interest or is the same size of a chromosome of interest, and sometimes is smaller than a reference chromosome or is the same size as a reference chromosome.

Filtering and/or Selecting Portions

In various embodiments, one or more processing steps can comprise one or more portion filtering steps and/or portion selection steps. In some embodiments, filtering includes removing portions or portions of a reference genome from consideration. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions.

Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or underrepresented sequences, noisy data, the like, or combinations of the foregoing. A filtering process may include removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or part of a chromosome by a predetermined multiple of the profile variance, and in certain embodiments, a filtering process comprises removing data points from a data set that do not deviate from the mean profile level of a portion, a chromosome or part of a chromosome by a predetermined multiple of the profile variance. In some embodiments, a filtering process is utilized to reduce the number of candidate portions of a reference genome analyzed for the presence or absence of a genetic variation/genetic alteration and/or copy number alteration (e.g., aneuploidy, microdeletion, microduplication). Reducing the number of candidate portions of a reference genome analyzed for the presence or absence of a genetic variation/genetic alteration and/or copy number alteration often reduces the complexity and/or dimensionality of a data set, and sometimes increases the speed of searching for and/or identifying genetic variations/genetic alteration and/or copy number alterations by two or more orders of magnitude.

Portions may be processed (e.g., filtered and/or selected) by any suitable method and according to any suitable parameter. Non-limiting examples of features and/or parameters that can be used to filter and/or select portions include redundant data (e.g., redundant or overlapping mapped reads), non-informative data (e.g., portions of a reference genome with zero mapped counts), portions of a reference genome with over represented or under represented sequences, noisy data, counts, count variability, coverage, mappability, variability, a repeatability measure, read density, variability of read density, a level of uncertainty, guanine-cytosine (GC) content, CCF fragment length and/or read length (e.g., a fragment length ratio (FLR), a fetal ratio statistic (FRS)), DNaseI-sensitivity, methylation state, acetylation, histone distribution, chromatin structure, percent repeats, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

In some embodiments, portions may be filtered according to a measure of error (e.g., standard deviation, standard error, calculated variance, p-value, mean absolute error (MAE), average absolute deviation and/or mean absolute deviation (MAD)). In certain instances, a measure of error may refer to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments, portions with a count variability above a pre-determined upper range are filtered (e.g., excluded from consideration). In some embodiments portions with a count variability below a pre-determined lower range are filtered (e.g., excluded from consideration). In some embodiments, portions with a count variability outside a pre-determined range are filtered (e.g., excluded from consideration). In some embodiments portions with a count variability within a pre-determined range are selected (e.g., used for determining the presence or absence of a copy number alteration). In some embodiments, count variability of portions represents a distribution (e.g., a normal distribution). In some embodiments portions are selected within a quantile of the distribution. In some embodiments portions within a 99% quantile of the distribution of count variability are selected.

Sequence reads from any suitable number of samples can be utilized to identify a subset of portions that meet one or more criteria, parameters and/or features described herein. Sequence reads from a group of samples from multiple subjects sometimes are utilized. In some embodiments, the multiple subjects include pregnant females. In some embodiments, the multiple subjects include healthy subjects. In some embodiments, the multiple subjects include cancer patients. One or more samples from each of the multiple subjects can be addressed (e.g., 1 to about 20 samples from each subject (e.g., about 2, 3, 4, 5, 6, 7, 8, 9, 10, 11, 12, 13, 14, 15, 16, 17, 18 or 19 samples)), and a suitable number of subjects may be addressed (e.g., about 2 to about 10,000 subjects (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 subjects)). In some embodiments, sequence reads from the same test sample(s) from the same subject are mapped to portions in the reference genome and are used to generate the subset of portions.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

In some embodiments, sequence reads derived from a sample are mapped to all or most portions of a reference genome and a pre-selected subset of portions are thereafter selected. For example, a subset of portions to which reads from fragments under a particular length threshold preferentially map may be selected. Certain methods for pre-selecting a subset of portions are described in U.S. Patent Application Publication No. 2014/0180594, which is incorporated by reference herein. Reads from a selected subset of portions often are utilized in further steps of a determination of the presence or absence of a genetic variation or genetic alteration, for example. Often, reads from portions not selected are not utilized in further steps of a determination of the presence or absence of a genetic variation or genetic alteration (e.g., reads in the non-selected portions are removed or filtered).

In some embodiments portions associated with read densities (e.g., where a read density is for a portion) are removed by a filtering process and read densities associated with removed portions are not included in a determination of the presence or absence of a copy number alteration (e.g., a chromosome aneuploidy, microduplication, microdeletion). In some embodiments a read density profile comprises and/or consists of read densities of filtered portions. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples may be referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process.

In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

Sequence Read Quantification

Sequence reads that are mapped or partitioned based on a selected feature or variable can be quantified to determine the amount or number of reads that are mapped to one or more portions (e.g., portion of a reference genome), in some embodiments. In certain embodiments the quantity of sequence reads that are mapped to a portion or segment is referred to as a count or read density.

A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region (described herein)).

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region a to a quantification for portion(s) in region b. Region a sometimes is one portion, segment region, copy number variation region, copy number alteration region, copy number duplication region, copy number deletion region, microduplication region, microdeletion region, chromosome region, autosome region and/or sex chromosome region. Region b independently sometimes is one portion, segment region, copy number variation region, copy number alteration region, copy number duplication region, copy number deletion region, microduplication region, microdeletion region, chromosome region, autosome region, sex chromosome region, a region including all autosomes, a region including sex chromosomes and/or a region including all chromosomes.

In some embodiments, a count is derived from raw sequence reads and/or filtered sequence reads. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which are described herein. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value.

A level for one or more portions is synonymous with a "genomic section level" herein. The term "level" as used herein is sometimes synonymous with the term "elevation." A determination of the meaning of the term "level" can be determined from the context in which it is used. For example, the term "level," when used in the context of portions, profiles, reads and/or counts often means an elevation. The term "level," when used in the context of a substance or composition (e.g., level of RNA, plexing level) often refers to an amount. The term "level," when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a fist level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or part thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a part of a chromosome).

In some embodiments, a level is determined for normalized or non-normalized counts of portions that are contiguous. In some embodiments portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or part thereof. In some embodiments a level is determined from a collection (e.g., a set) of contiguous portions and/or non-contiguous portions.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation or genetic alteration (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments one or more processing steps can comprise one or more normalization steps. Normalization can be performed by a suitable method described herein or known in the art. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter are certain examples of normalization processes that can be utilized, such as LOESS normalization, principal component normalization, and hybrid normalization methods, for example. Aspects of certain normalization processes also are described, for example, in International Patent Application Publication No. WO2013/052913 and International Patent Application Publication No. WO2015/051163, each of which is incorporated by reference herein.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization."

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include principal component analysis, decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principal component analysis, linear discriminant analysis, quadratic discriminant analysis, bagging, neural networks, support vector machine models, random forests, classification tree models, K-nearest neighbors, logistic regression and/or smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation/genetic alteration and/or copy number alteration, depending on the status of the reference samples (e.g., positive or negative for a selected copy number alteration). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation/genetic alteration and/or copy number alteration and/or medical condition.

After data sets have been counted, optionally filtered, normalized, and optionally weighted the processed data sets can be further manipulated by one or more filtering and/or normalizing and/or weighting procedures, in some embodiments. A data set that has been further manipulated by one or more filtering and/or normalizing and/or weighting procedures can be used to generate a profile, in certain embodiments. The one or more filtering and/or normalizing and/or weighting procedures sometimes can reduce data set complexity and/or dimensionality, in some embodiments. An outcome can be provided based on a data set of reduced complexity and/or dimensionality. In some embodiments, a profile plot of processed data further manipulated by weighting, for example, is generated to facilitate classification and/or providing an outcome. An outcome can be provided based on a profile plot of weighted data, for example.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fraction of a minority species (e.g., fraction of cancer cell nucleic acid; fetal fraction). In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fraction of a minority species (e.g., fraction of cancer cell nucleic acid; fetal fraction).

In some embodiments, analysis and processing of data can include the use of one or more assumptions. A suitable number or type of assumptions can be utilized to analyze or process a data set. Non-limiting examples of assumptions that can be used for data processing and/or analysis include subject ploidy, cancer cell contribution, maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a nucleic acid quantification assay (e.g., fetal quantifier assay (FQA)), assumptions regarding twins (e.g., if 2 twins and only 1 is affected the effective fetal fraction is only 50% of the total measured fetal fraction (similarly for triplets, quadruplets and the like)), cell free DNA (e.g., cfDNA) uniformly covers the entire genome, the like and combinations thereof.

In those instances where the quality and/or depth of mapped sequence reads does not permit an outcome prediction of the presence or absence of a genetic variation/genetic alteration and/or copy number alteration at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Described in greater detail hereafter are non-limiting examples of processing steps and normalization methods that can be utilized, such as normalizing to a window (static or sliding), weighting, determining bias relationship, LOESS normalization, principal component normalization, hybrid normalization, generating a profile and performing a comparison.

Normalizing to a Window (Static or Sliding)

In certain embodiments, a processing step comprises normalizing to a static window, and in some embodiments, a processing step comprises normalizing to a moving or sliding window.

The term "window" as used herein refers to one or more portions chosen for analysis, and sometimes is used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate surrounding portions, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of microdeletions and/or microduplications. In certain embodiments, displaying cumulative sums of one or more portions is used to identify the presence or absence of regions of copy number alteration (e.g., microdeletion, microduplication).

Weighting

In some embodiments, a processing step comprises a weighting. The terms "weighted," "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is [1/(standard deviation)]. Weighting portions sometimes removes portion dependencies. In some embodiments one or more portions are weighted by an eigen function (e.g., an eigenfunction). In some embodiments an eigen function comprises replacing portions with orthogonal eigen-portions. A weighting step sometimes is performed in a manner substantially similar to a normalizing step. In some embodiments, a data set is adjusted (e.g., divided, multiplied, added, subtracted) by a predetermined variable (e.g., weighting variable). In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

Bias Relationships

In some embodiments, a processing step comprises determining a bias relationship. For example, one or more relationships may be generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content.

In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments, a processing step comprises normalizing sequence read counts by comparing local genome bias estimates of sequence reads of a test sample to local genome bias estimates of a reference (e.g., a reference genome, or part thereof). In some embodiments, counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads may be normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

LOESS Normalization

In some embodiments, a processing step comprises a LOESS normalization. LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Principal Component Analysis

In some embodiments, a processing step comprises a principal component analysis (PCA). In some embodiments, sequence read counts (e.g., sequence read counts of a test sample) is adjusted according to a principal component analysis (PCA). In some embodiments a read density profile (e.g., a read density profile of a test sample) is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies and/or adjusts for one or more biases in a read density profile. A bias identified and/or adjusted for by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments, one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$ $6^{th}$, $7^{th}$, $8^{th}$, $9^{th}$, and a $10^{th}$ or more principal components. In certain embodiments, 1, 2, 3, 4, 5, 6, 7, 8, 9, 10 or more principal components are used to adjust a profile. In certain embodiments, 5 principal components are used to adjust a profile. Often, principal components are used to adjust a profile in the order of appearance in a PCA. For example, where three principal components are subtracted from a read density profile, a $1^{st}$, $2^{nd}$ and $3^{rd}$ principal component are used.

Sometimes a bias identified by a principal component comprises a feature of a profile that is not used to adjust a profile. For example, a PCA may identify a copy number alteration (e.g., an aneuploidy, microduplication, microdeletion, deletion, translocation, insertion) and/or a gender difference as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile.

A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). In certain instances, a PCA is performed on a median read density profile obtained from a training set comprising multiple samples resulting in the identification of a $1^{st}$ principal component and a $2^{nd}$ principal component. In some embodiments, principal components are obtained from a set of subjects devoid of a copy number alteration in question. In some embodiments, principal components are obtained from a set of known euploids. Principal component are often identified according to a PCA performed using one or more read density profiles of a reference (e.g., a training set). One or more principal components obtained from a reference are often subtracted from a read density profile of a test subject thereby providing an adjusted profile.

Hybrid Normalization

In some embodiments, a processing step comprises a hybrid normalization method. A hybrid normalization method may reduce bias (e.g., GC bias), in certain instances. A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method.

For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by LOESS, principal component, or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature (Tm) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample. In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis.

An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is predetermined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate levels, Z-scores, levels and/or profiles of a genome or a part thereof. In certain embodiments, counts normalized by a hybrid normalization approach are analyzed by methods described herein to determine the presence or absence of a genetic variation or genetic alteration (e.g., copy number alteration).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

Profiles

In some embodiments, a processing step comprises generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a part of a chromosome) often is a collection of normalized or non-normalized counts for two or more portions. A profile often includes at least one level, and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to copy number alterations (e.g., microduplications or microdeletions in a patient's genome, maternal microduplications or microdeletions). In some embodiments, levels are padded that are due to microduplications or microdeletions in a tumor or a fetus. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments, levels in a profile that are due to microduplications and/or deletions are identified and adjusted (e.g., padded and/or removed) by a process sometimes referred to as padding or hole padding.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured minority species fraction, principal components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured minority species fraction, principal components). The terms "raw count profile plot" or "raw profile plot" as used herein refer to a plot of counts in each portion in a region normalized to total counts in a region (e.g., genome, portion, chromosome, chromosome portions of a reference genome or a part of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions, e.g., assumptions described herein. In certain embodiments, a test profile often centers around a predetermined value representative of the absence of a copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for a selected portion is expected to vary significantly from the predetermined value for non-affected genomic locations. Depending on starting assumptions (e.g., fixed ploidy or optimized ploidy, fixed fraction of cancer cell nucleic acid or optimized fraction of cancer cell nucleic acid, fixed fetal fraction or optimized fetal fraction, or combinations thereof) the predetermined threshold or cutoff value or threshold range of values indicative of the presence or absence of a copy number alteration can vary while still providing an outcome useful for determining the presence or absence of a copy number alteration. In some embodiments, a profile is indicative of and/or representative of a phenotype.

In some embodiments, the use of one or more reference samples that are substantially free of a copy number alteration in question can be used to generate a reference count profile (e.g., a reference median count profile), which may result in a predetermined value representative of the absence of the copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for the selected portion or sections is expected to vary significantly from the predetermined value for non-affected genomic locations. In certain embodiments, the use of one or more reference samples known to carry the copy number alteration in question can be used to generate a reference count profile (a reference median count profile), which may result in a predetermined value representative of the presence of the copy number alteration, and often deviates from a predetermined value in areas corresponding to the genomic location in which a test subject does not carry the copy number alteration. In test subjects not at risk for, or suffering from a medical condition associated with a copy number alteration, the numerical value for the selected portion or sections is expected to vary significantly from the predetermined value for affected genomic locations.

By way of a non-limiting example, normalized sample and/or reference count profiles can be obtained from raw sequence read data by (a) calculating reference median counts for selected chromosomes, portions or parts thereof from a set of references known not to carry a copy number alteration, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

In some embodiments a read density profile is determined. In some embodiments a read density profile comprises at least one read density, and often comprises two or more read densities (e.g., a read density profile often comprises multiple read densities). In some embodiments, a read density profile comprises a suitable quantitative value (e.g., a mean, a median, a Z-score, or the like). A read density profile often comprises values resulting from one or more read densities. A read density profile sometimes comprises values resulting from one or more manipulations of read densities based on one or more adjustments (e.g., normalizations). In some embodiments a read density profile comprises unmanipulated read densities. In some embodiments, one or more read density profiles are generated from various aspects of a data set comprising read densities, or a derivation thereof (e.g., product of one or more mathematical and/or statistical data processing steps known in the art and/or described herein). In certain embodiments, a read density profile comprises normalized read densities. In some embodiments a read density profile comprises adjusted read densities. In certain embodiments a read density profile comprises raw read densities (e.g., unmanipulated, not adjusted or normalized), normalized read densities, weighted read densities, read densities of filtered portions, z-scores of read densities, p-values of read densities, integral values of read densities (e.g., area under the curve), average, mean or median read densities, principal components, the like, or combinations thereof. Often read densities of a read density profile and/or a read density profile is associated with a measure of uncertainty (e.g., a MAD). In certain embodiments, a read density profile comprises a distribution of median read densities. In some embodiments a read density profile comprises a relationship (e.g., a fitted relationship, a regression, or the like) of a plurality of read densities. For example, sometimes a read density profile comprises a relationship between read densities (e.g., read densities value) and genomic locations (e.g., portions, portion locations). In some embodiments, a read density profile is generated using a static window process, and in certain embodiments, a read density profile is generated using a sliding window process. In some embodiments a read density profile is sometimes printed and/or displayed (e.g., displayed as a visual representation, e.g., a plot or a graph).

In some embodiments, a read density profile corresponds to a set of portions (e.g., a set of portions of a reference genome, a set of portions of a chromosome or a subset of portions of a part of a chromosome). In some embodiments a read density profile comprises read densities and/or counts associated with a collection (e.g., a set, a subset) of portions. In some embodiments, a read density profile is determined for read densities of portions that are contiguous. In some embodiments, contiguous portions comprise gaps comprising regions of a reference sequence and/or sequence reads that are not included in a density profile (e.g., portions removed by a filtering). Sometimes portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent an intact genome, chromosome, gene, intron, exon or part thereof. Sometimes a read density profile is determined from a collection (e.g., a set, a subset) of contiguous portions and/or non-contiguous portions. In some cases, a read density profile comprises one or more portions, which portions can be weighted, removed, filtered, normalized, adjusted, averaged, derived as a mean, added, subtracted, processed or transformed by any combination thereof.

A read density profile is often determined for a sample and/or a reference (e.g., a reference sample). A read density profile is sometimes generated for an entire genome, one or more chromosomes, or for a part of a genome or a chromosome. In some embodiments, one or more read density profiles are determined for a genome or part thereof. In some embodiments, a read density profile is representative of the entirety of a set of read densities of a sample, and in certain embodiments, a read density profile is representative of a part or subset of read densities of a sample. That is, sometimes a read density profile comprises or is generated from read densities representative of data that has not been filtered to remove any data, and sometimes a read density profile includes or is generated from data points representative of data that has been filtered to remove unwanted data.

In some embodiments a read density profile is determined for a reference (e.g., a reference sample, a training set). A read density profile for a reference is sometimes referred to herein as a reference profile. In some embodiments a reference profile comprises a read densities obtained from one or more references (e.g., reference sequences, reference samples). In some embodiments a reference profile comprises read densities determined for one or more (e.g., a set of) known euploid samples. In some embodiments a reference profile comprises read densities of filtered portions. In some embodiments a reference profile comprises read densities adjusted according to the one or more principal components.

Performing a Comparison

In some embodiments, a processing step comprises preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principal component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In some embodiments, a processing step comprises a comparison of two or more profiles (e.g., two or more read density profiles). Comparing profiles may comprise comparing profiles generated for a selected region of a genome.

For example, a test profile may be compared to a reference profile where the test and reference profiles were determined for a region of a genome (e.g., a reference genome) that is substantially the same region. Comparing profiles sometimes comprises comparing two or more subsets of portions of a profile (e.g., a read density profile). A subset of portions of a profile may represent a region of a genome (e.g., a chromosome, or region thereof). A profile (e.g., a read density profile) can comprise any amount of subsets of portions. Sometimes a profile (e.g., a read density profile) comprises two or more, three or more, four or more, or five or more subsets. In certain embodiments, a profile (e.g., a read density profile) comprises two subsets of portions where each portion represents regions of a reference genome that are adjacent. In some embodiments, a test profile can be compared to a reference profile where the test profile and reference profile both comprise a first subset of portions and a second subset of portions where the first and second subsets represent different regions of a genome. Some subsets of portions of a profile may comprise copy number alterations and other subsets of portions are sometimes substantially free of copy number alterations. Sometimes all subsets of portions of a profile (e.g., a test profile) are substantially free of a copy number alteration. Sometimes all subsets of portions of a profile (e.g., a test profile) comprise a copy number alteration. In some embodiments a test profile can comprise a first subset of portions that comprise a copy number alteration and a second subset of portions that are substantially free of a copy number alteration.

In certain embodiments, comparing two or more profiles comprises determining and/or comparing a measure of uncertainty for two or more profiles. Profiles (e.g., read density profiles) and/or associated measures of uncertainty are sometimes compared to facilitate interpretation of mathematical and/or statistical manipulations of a data set and/or to provide an outcome. A profile (e.g., a read density profile) generated for a test subject sometimes is compared to a profile (e.g., a read density profile) generated for one or more references (e.g., reference samples, reference subjects, and the like). In some embodiments, an outcome is provided by comparing a profile (e.g., a read density profile) from a test subject to a profile (e.g., a read density profile) from a reference for a chromosome, portions or parts thereof, where a reference profile is obtained from a set of reference subjects known not to possess a copy number alteration (e.g., a reference). In some embodiments an outcome is provided by comparing a profile (e.g., a read density profile) from a test subject to a profile (e.g., a read density profile) from a reference for a chromosome, portions or parts thereof, where a reference profile is obtained from a set of reference subjects known to possess a specific copy number alteration (e.g., a chromosome aneuploidy, a microduplication, a microdeletion).

In certain embodiments, a profile (e.g., a read density profile) of a test subject is compared to a predetermined value representative of the absence of a copy number alteration, and sometimes deviates from a predetermined value at one or more genomic locations (e.g., portions) corresponding to a genomic location in which a copy number alteration is located. For example, in test subjects (e.g., subjects at risk for, or suffering from a medical condition associated with a copy number alteration), profiles are expected to differ significantly from profiles of a reference (e.g., a reference sequence, reference subject, reference set) for selected portions when a test subject comprises a copy number alteration in question. Profiles (e.g., read density profiles) of a test subject are often substantially the same as profiles (e.g., read density profiles) of a reference (e.g., a reference sequence, reference subject, reference set) for selected portions when a test subject does not comprise a copy number alteration in question. Profiles (e.g., read density profiles) may be compared to a predetermined threshold and/or threshold range. The term "threshold" as used herein refers to any number that is calculated using a qualifying data set and serves as a limit of diagnosis of a copy number alteration (e.g., an aneuploidy, a microduplication, a microdeletion, and the like). In certain embodiments a threshold is exceeded by results obtained by methods described herein and a subject is diagnosed with a copy number alteration. In some embodiments, a threshold value or range of values may be calculated by mathematically and/or statistically manipulating sequence read data (e.g., from a reference and/or subject). A predetermined threshold or threshold range of values indicative of the presence or absence of a copy number alteration can vary while still providing an outcome useful for determining the presence or absence of a copy number alteration. In certain embodiments, a profile (e.g., a read density profile) comprising normalized read densities and/or normalized counts is generated to facilitate classification and/or providing an outcome. An outcome can be provided based on a plot of a profile (e.g., a read density profile) comprising normalized counts (e.g., using a plot of such a read density profile).

Decision Analysis

In some embodiments, a determination of an outcome (e.g., making a call) or a determination of the presence or absence of a copy number alteration (e.g., chromosome aneuploidy, microduplication, microdeletion) is made according to a decision analysis. Certain decision analysis features are described in International Patent Application Publication No. WO2014/190286, which is incorporated by reference herein. For example, a decision analysis sometimes comprises applying one or more methods that produce one or more results, an evaluation of the results, and a series of decisions based on the results, evaluations and/or the possible consequences of the decisions and terminating at some juncture of the process where a final decision is made. In some embodiments a decision analysis is a decision tree. A decision analysis, in some embodiments, comprises coordinated use of one or more processes (e.g., process steps, e.g., algorithms). A decision analysis can be performed by a person, a system, an apparatus, software (e.g., a module), a computer, a processor (e.g., a microprocessor), the like or a combination thereof. In some embodiments a decision analysis comprises a method of determining the presence or absence of a copy number alteration (e.g., chromosome aneuploidy, microduplication or microdeletion) with reduced false negative and reduced false positive determinations, compared to an instance in which no decision analysis is utilized (e.g., a determination is made directly from normalized counts). In some embodiments a decision analysis comprises determining the presence or absence of a condition associated with one or more copy number alterations.

In some embodiments a decision analysis comprises generating a profile for a genome or a region of a genome (e.g., a chromosome or part thereof). A profile can be generated by any suitable method, known or described herein. In some embodiments, a decision analysis comprises a segmenting process. Segmenting can modify and/or transform a profile thereby providing one or more decomposition renderings of a profile. A profile subjected to a segmenting process often is a profile of normalized counts mapped to portions in a reference genome or part thereof. As addressed herein, raw counts mapped to the portions can be normalized by one or more suitable normalization processes (e.g., LOESS, GC-LOESS, principal component normalization, or combination thereof) to generate a profile that is segmented as part of a decision analysis. A decomposition rendering of a profile is often a transformation of a profile. A decomposition rendering of a profile is sometimes a transformation of a profile into a representation of a genome, chromosome or part thereof.

In certain embodiments, a segmenting process utilized for the segmenting locates and identifies one or more levels within a profile that are different (e.g., substantially or significantly different) than one or more other levels within a profile. A level identified in a profile according to a segmenting process that is different than another level in the profile, and has edges that are different than another level in the profile, is referred to herein as a level for a discrete segment. A segmenting process can generate, from a profile of normalized counts or levels, a decomposition rendering in which one or more discrete segments can be identified. A discrete segment generally covers fewer portions than what is segmented (e.g., chromosome, chromosomes, autosomes).

In some embodiments, segmenting locates and identifies edges of discrete segments within a profile. In certain embodiments, one or both edges of one or more discrete segments are identified. For example, a segmentation process can identify the location (e.g., genomic coordinates, e.g., portion location) of the right and/or the left edges of a discrete segment in a profile. A discrete segment often comprises two edges. For example, a discrete segment can include a left edge and a right edge. In some embodiments, depending upon the representation or view, a left edge can be a 5'-edge and a right edge can be a 3'-edge of a nucleic acid segment in a profile. In some embodiments, a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment is an edge of a chromosome.

In some embodiments, the edges of a discrete segment are determined according to a decomposition rendering generated for a reference sample (e.g., a reference profile). In some embodiments a null edge height distribution is determined according to a decomposition rendering of a reference profile (e.g., a profile of a chromosome or part thereof). In certain embodiments, the edges of a discrete segment in a profile are identified when the level of the discrete segment is outside a null edge height distribution. In some embodiments, the edges of a discrete segment in a profile are identified according a Z-score calculated according to a decomposition rendering for a reference profile.

In some instances, segmenting generates two or more discrete segments (e.g., two or more fragmented levels, two or more fragmented segments) in a profile. In some embodiments, a decomposition rendering derived from a segmenting process is over-segmented or fragmented and comprises multiple discrete segments. Sometimes discrete segments generated by segmenting are substantially different and sometimes discrete segments generated by segmenting are substantially similar. Substantially similar discrete segments (e.g., substantially similar levels) often refers to two or more adjacent discrete segments in a segmented profile each having a level that differs by less than a predetermined level of uncertainty. In some embodiments, substantially similar discrete segments are adjacent to each other and are not separated by an intervening segment. In some embodiments, substantially similar discrete segments are separated by one or more smaller segments. In some embodiments substantially similar discrete segments are separated by about 1 to about 20, about 1 to about 15, about 1 to about 10 or about 1 to about 5 portions where one or more of the intervening portions have a level significantly different than the level of each of the substantially similar discrete segments. In some embodiments, the level of substantially similar discrete segments differs by less than about 3 times, less than about 2 times, less than about 1 time or less than about 0.5 times a level of uncertainty. Substantially similar discrete segments, in some embodiments, comprise a median level that differs by less than 3 MAD (e.g., less than 3 sigma), less than 2 MAD, less than 1 MAD or less than about 0.5 MAD, where a MAD is calculated from a median level of each of the segments. Substantially different discrete segments, in some embodiments, are not adjacent or are separated by 10 or more, 15 or more or 20 or more portions. Substantially different discrete segments generally have substantially different levels. In certain embodiments, substantially different discrete segments comprises levels that differ by more than about 2.5 times, more than about 3 times, more than about 4 times, more than about 5 times, more than about 6 times a level of uncertainty. Substantially different discrete segments, in some embodiments, comprise a median level that differs by more than 2.5 MAD (e.g., more than 2.5 sigma), more than 3 MAD, more than 4 MAD, more than about 5 MAD or more than about 6 MAD, where a MAD is calculated from a median level of each of the discrete segments.

In some embodiments, a segmentation process comprises determining (e.g., calculating) a level (e.g., a quantitative value, e.g., a mean or median level), a level of uncertainty (e.g., an uncertainty value), Z-score, Z-value, p-value, the like or combinations thereof for one or more discrete segments in a profile or part thereof. In some embodiments a level (e.g., a quantitative value, e.g., a mean or median level), a level of uncertainty (e.g., an uncertainty value), Z-score, Z-value, p-value, the like or combinations thereof are determined (e.g., calculated) for a discrete segment.

Segmenting can be performed, in full or in part, by one or more decomposition generating processes. A decomposition generating process may provide, for example, a decomposition rendering of a profile. Any decomposition generating process described herein or known in the art may be used. Non-limiting examples of a decomposition generating process include circular binary segmentation (CBS) (see e.g., Olshen et al. (2004) Biostatistics 5(4):557-72; Venkatraman, ES, Olshen, AB (2007) Bioinformatics 23(6):657-63); Haar wavelet segmentation (see e.g., Haar, Alfred (1910) Mathematische Annalen 69(3):331-371); maximal overlap discrete wavelet transform (MODWT) (see e.g., Hsu et al. (2005) Biostatistics 6 (2):211-226); stationary wavelet (SWT) (see e.g., Y. Wang and S. Wang (2007) International Journal of Bioinformatics Research and Applications 3(2): 206-222); dual-tree complex wavelet transform (DTCWT) (see e.g., Nguyen et al. (2007) Proceedings of the 7th IEEE International Conference, Boston MA, on Oct. 14-17, 2007, pages 137-144); maximum entropy segmentation, convolution with edge detection kernel, Jensen Shannon Divergence, Kullback-Leibler divergence, Binary Recursive Segmentation, a Fourier transform, the like or combinations thereof.

In some embodiments, segmenting is accomplished by a process that comprises one process or multiple sub-processes, non-limiting examples of which include a decomposition generating process, thresholding, leveling, smoothing, polishing, the like or combination thereof. Thresholding, leveling, smoothing, polishing and the like can be performed in conjunction with a decomposition generating process, for example.

In some embodiments, a decision analysis comprises identifying a candidate segment in a decomposition rendering. A candidate segment is determined as being the most significant discrete segment in a decomposition rendering. A candidate segment may be the most significant in terms of the number of portions covered by the segment and/or in terms of the absolute value of the level of normalized counts for the segment. A candidate segment sometimes is larger and sometimes substantially larger than other discrete segments in a decomposition rendering. A candidate segment can be identified by a suitable method. In some embodiments, a candidate segment is identified by an area under the curve (AUC) analysis. In certain embodiments, where a first discrete segment has a level and/or covers a number of portions substantially larger than for another discrete segment in a decomposition rendering, the first segment comprises a larger AUC. Where a level is analyzed for AUC, an absolute value of a level often is utilized (e.g., a level corresponding to normalized counts can have a negative value for a deletion and a positive value for a duplication). In certain embodiments, an AUC is determined as an absolute value of a calculated AUC (e.g., a resulting positive value). In certain embodiments, a candidate segment, once identified (e.g., by an AUC analysis or by a suitable method) and optionally after it is validated, is selected for a z-score calculation, or the like, to determine if the candidate segment represents a genetic variation or genetic alteration (e.g., an aneuploidy, microdeletion or microduplication).

In some embodiments, a decision analysis comprises a comparison. In some embodiments, a comparison comprises comparing at least two decomposition renderings. In some embodiments, a comparison comprises comparing at least two candidate segments. In certain embodiments, each of the at least two candidate segments is from a different decomposition rendering. For example, a first candidate segment can be from a first decomposition rendering and a second candidate segment can be from a second decomposition rendering. In some embodiments, a comparison comprises determining if two decomposition renderings are substantially the same or different. In some embodiments, a comparison comprises determining if two candidate segments are substantially the same or different. Two candidate segments can be determined as substantially the same or different by a suitable comparison method, non-limiting examples of which include by visual inspection, by comparing levels or Z-scores of the two candidate segments, by comparing the edges of the two candidate segments, by overlaying either the two candidate segments or their corresponding decomposition renderings, the like or combinations thereof.

Classifications and Uses Thereof

Methods described herein can provide an outcome indicative of a genotype and/or presence or absence of a genetic variation/alteration in a genomic region for a test sample (e.g., providing an outcome determinative of the presence or absence of a genetic variation). Methods described herein sometimes provide an outcome indicative of a phenotype and/or presence or absence of a medical condition for a test sample (e.g., providing an outcome determinative of the presence or absence of a medical condition and/or phenotype). An outcome often is part of a classification process, and a classification (e.g., classification of presence or absence of a genotype, phenotype, genetic variation and/or medical condition for a test sample) sometimes is based on and/or includes an outcome. An outcome and/or classification sometimes is based on and/or includes a result of data processing for a test sample that facilitates determining presence or absence of a genotype, phenotype, genetic variation, genetic alteration, and/or medical condition in a classification process (e.g., a statistic value (e.g., standard score (e.g., z-score)). An outcome and/or classification sometimes includes or is based on a score determinative of, or a call of, presence or absence of a genotype, phenotype, genetic variation, genetic alteration, and/or medical condition. In certain embodiments, an outcome and/or classification includes a conclusion that predicts and/or determines presence or absence of a genotype, phenotype, genetic variation, genetic alteration, and/or medical condition in a classification process.

A genotype and/or genetic variation often includes a gain, a loss and/or alteration of a region comprising one or more nucleotides (e.g., duplication, deletion, fusion, insertion, short tandem repeat (STR), mutation, single nucleotide alteration, reorganization, substitution or aberrant methylation) that results in a detectable change in the genome or genetic information for a test sample. A genotype and/or genetic variation often is in a particular genomic region (e.g., chromosome, portion of a chromosome (i.e., sub-chromosome region), STR, polymorphic region, translocated region, altered nucleotide sequence, the like or combinations of the foregoing). A genetic variation sometimes is a copy number alteration for a particular region, such as a trisomy or monosomy for chromosome region, or a microduplication or microdeletion event for a particular region (e.g., gain or loss of a region of about 10 megabases or less (e.g., about 9 megabases or less, 8 megabases or less, 7 megabases or less, 6 megabases or less, 5 megabases or less, 4 megabases or less, 3 megabases or less, 2 megabases or less or 1 megabase or less)), for example. A copy number alteration sometimes is expressed as having no copy or one, two, three or four or more copies of a particular region (e.g., chromosome, sub-chromosome, STR, microduplication or microdeletion region).

Presence or absence of a genotype, phenotype, genetic variation and/or medical condition can be determined by transforming, analyzing and/or manipulating sequence reads that have been mapped to genomic portions (e.g., counts, counts of genomic portions of a reference genome). In certain embodiments, an outcome and/or classification is determined according to normalized counts, read densities, read density profiles, and the like, and can be determined by a method described herein. An outcome and/or classification sometimes includes one or more scores and/or calls that refer to the probability that a particular genotype, phenotype, genetic variation, or medical condition is present or absent for a test sample. The value of a score may be used to determine, for example, a variation, difference, or ratio of mapped sequence reads that may correspond to a genotype, phenotype, genetic variation, or medical condition. For example, calculating a positive score for a selected genotype, phenotype, genetic variation, or medical condition from a data set, with respect to a reference genome, can lead to a classification of the genotype, phenotype, genetic variation, or medical condition, for a test sample.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining whether a subject is at risk of having, or has, a genotype, phenotype, genetic variation and/or medical condition, and an outcome and/or classification determinative of the foregoing sometimes includes such a consideration.

In certain embodiments, an outcome and/or classification is based on and/or includes a conclusion that predicts and/or determines a risk or probability of the presence or absence of a genotype, phenotype, genetic variation and/or medical condition for a test sample. A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report (described in greater detail hereafter) for particular test sample as a probability (e.g., odds ratio, p-value), likelihood, or risk factor, associated with the presence or absence of a genotype, phenotype, genetic variation and/or medical condition. An outcome and/or classification for a test sample sometimes is provided as "positive" or "negative" with respect a particular genotype, phenotype, genetic variation and/or medical condition. For example, an outcome and/or classification sometimes is designated as "positive" in a laboratory test report for a particular test sample where presence of a genotype, phenotype, genetic variation and/or medical condition is determined, and sometimes an outcome and/or classification is designated as "negative" in a laboratory test report for a particular test sample where absence of a genotype, phenotype, genetic variation and/or medical condition is determined. An outcome and/or classification sometimes is determined and sometimes includes an assumption used in data processing.

An outcome and/or classification sometimes is based on or is expressed as a value in or out of a cluster, value over or under a threshold value, value within a range (e.g., a threshold range), and/or a value with a measure of variance or confidence. In some embodiments, an outcome and/or classification is based on or is expressed as a value above or below a predetermined threshold or cutoff value and/or a measure of uncertainty, confidence level or confidence interval associated with the value. In certain embodiments, a predetermined threshold or cutoff value is an expected level or an expected level range. In some embodiments, a value obtained for a test sample is a standard score (e.g., z-score), where presence of a genotype, phenotype, genetic variation and/or medical condition is determined when the absolute value of the score is greater than a particular score threshold (e.g., threshold between about 2 and about 5; between about 3 and about 4), and where the absence of a genotype, phenotype, genetic variation and/or medical condition is determined when the absolute value of the score is less than the particular score threshold. In certain embodiments, an outcome and/or classification is based on or is expressed as a value that falls within or outside a predetermined range of values (e.g., a threshold range) and the associated uncertainty or confidence level for that value being inside or outside the range. In some embodiments, an outcome and/or classification comprises a value that is equal to a predetermined value (e.g., equal to 1, equal to zero), or is equal to a value within a predetermined value range, and its associated uncertainty or confidence level for that value being equal or within or outside the range. An outcome and/or classification sometimes is graphically represented as a plot (e.g., profile plot). An outcome and/or classification sometimes comprises use of a reference value or reference profile, and sometimes a reference value or reference profile is obtained from one or more reference samples (e.g., reference sample(s) euploid for a selected part of a genome (e.g., region)).

In some embodiments, an outcome and/or classification is based on or includes use of a measure of uncertainty between a test value or profile and a reference value or profile for a selected region. In some embodiments, a determination of the presence or absence of a genotype, phenotype, genetic variation and/or medical condition is according to the number of deviations (e.g., sigma) between a test value or profile and a reference value or profile for a selected region (e.g., a chromosome, or part thereof). A measure of deviation often is an absolute value or absolute measure of deviation (e.g., mean absolute deviation or median absolute deviation (MAD)). In some embodiments, the presence of a genotype, phenotype, genetic variation and/or medical condition is determined when the number of deviations between a test value or profile and a reference value or profile is about 1 or greater (e.g., about 1.5, 2, 2.5, 2.6, 2.7, 2.8, 2.9, 3, 3.1, 3.2, 3.3, 3.4, 3.5, 3.6, 3.7, 3.8, 3.9, 4, 5 or 6 deviations or greater). In certain embodiments, presence of a genotype, phenotype, genetic variation and/or medical condition is determined when a test value or profile and a reference value or profile differ by about 2 to about 5 measures of deviation (e.g., sigma, MAD), or more than 3 measures of deviation (e.g., 3 sigma, 3 MAD). A deviation of greater than three between a test value or profile and a reference value or profile often is indicative of a non-euploid test subject (e.g., presence of a genetic variation (e.g., presence of trisomy, monosomy, microduplication, microdeletion) for a selected region. Test values or profiles significantly above a reference profile, which reference profile is indicative of euploidy, sometimes are determinative of a trisomy, sub-chromosome duplication or microduplication. Test values or profiles significantly below a reference profile, which reference profile is indicative of euploidy, sometimes are determinative of a monosomy, sub-chromosome deletion or microdeletion. In some embodiments, absence of a genotype, phenotype, genetic variation and/or medical condition is determined when the number of deviations between a test value or profile and reference value or profile for a selected region of a genome is about 3.5 or less (e.g., about less than about 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1 or less less). In certain embodiments, absence of a genotype, phenotype, genetic variation and/or medical condition is determined when a test value or profile differs from a reference value or profile by less than three measures of deviation (e.g., 3 sigma, 3 MAD). In some embodiments, a measure of deviation of less than three between a test value or profile and reference value or profile (e.g., 3-sigma for standard deviation) often is indicative of a region that is euploid (e.g., absence of a genetic variation). A measure of deviation between a test value or profile for a test sample and a reference value or profile for one or more reference subjects can be plotted and visualized (e.g., z-score plot).

In some embodiments, an outcome and/or classification is determined according to a call zone. In certain embodiments, a call is made (e.g., a call determining presence or absence of a genotype, phenotype, genetic variation and/or medical condition) when a value (e.g., a profile, a read density profile and/or a measure of uncertainty) or collection of values falls within a pre-defined range (e.g., a zone, a call zone). In some embodiments, a call zone is defined according to a collection of values (e.g., profiles, read density profiles, measures or determination of probability and/or measures of uncertainty) obtained from a particular group of samples. In certain embodiments, a call zone is defined according to a collection of values that are derived from the same chromosome or part thereof. In some embodiments, a call zone for determining presence or absence of a genotype, phenotype, genetic variation and/or medical condition is defined according a measure of uncertainty (e.g., high level of confidence or low measure of uncertainty) and/or a quantification of a minority nucleic acid species (e.g., about 1% minority species or greater (e.g., about 2, 3, 4, 5, 6, 7, 8, 9, 10% or more minority nucleic acid species)) determined for a test sample. A minority nucleic acid species quantification sometimes is a fraction or percent of cancer cell nucleic acid or fetal nucleic acid (i.e., fetal fraction) ascertained for a test sample. In some embodiments, a call zone is defined by a confidence level or confidence interval (e.g., a confidence interval for 95% level of confidence). A call zone sometimes is defined by a confidence level, or confidence interval based on a particular confidence level, of about 90% or greater (e.g., about 91, 92, 93, 94, 95, 96, 97, 98, 99, 99.1, 99.2, 99.3, 99.4, 99.5, 99.6, 99.7, 99.8, 99.9% or greater). In some embodiments, a call is made using a call zone and additional data or information. In some embodiments, a call is made without using a call zone. In some embodiments, a call is made based on a comparison without the use of a call zone. In some embodiments, a call is made based on visual inspection of a profile (e.g., visual inspection of read densities).

In some embodiments, a classification or call is not provided for a test sample when a test value or profile is in a no-call zone. In some embodiments, a no-call zone is defined by a value (e.g., collection of values) or profile that indicates low accuracy, high risk, high error, low level of confidence, high measure of uncertainty, the like or combination thereof. In some embodiments, a no-call zone is defined, in part, by a minority nucleic acid species quantification (e.g., a minority nucleic acid species of about 10% or less (e.g., about 9, 8, 7, 6, 5, 4, 3, 2% or less minority nucleic acid species)). An outcome and/or classification generated for determining the presence or absence of a genotype, phenotype, genetic variation and/or medical condition sometimes includes a null result. A null result sometimes is a data point between two clusters, a numerical value with a standard deviation that encompasses values for both the presence and absence of a genotype, phenotype, genetic variation and/or medical condition, a data set with a profile plot that is not similar to profile plots for subjects having or free from the genetic variation being investigated). In some embodiments, an outcome and/or classification indicative of a null result is considered a determinative result, and the determination can include a conclusion of the need for additional information and/or a repeat of data generation and/or analysis for determining the presence or absence of a genotype, phenotype, genetic variation and/or medical condition.

There typically are four types of classifications generated in a classification process: true positive, false positive, true negative and false negative. The term "true positive" as used herein refers to presence of a genotype, phenotype, genetic variation, or medical condition correctly determined for a test sample. The term "false positive" as used herein refers to presence of a genotype, phenotype, genetic variation, or medical condition incorrectly determined for a test sample. The term "true negative" as used herein refers to absence of a genotype, phenotype, genetic variation, or medical condition correctly determined for a test sample. The term "false negative" as used herein refers to absence of a genotype, phenotype, genetic variation, or medical condition incorrectly determined for a test sample. Two measures of performance for a classification process can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein. Specific examples of generating an outcome and/or classification and associated confidence levels are described, for example, in International Patent Application Publication Nos. WO2013/052913, WO2014/190286 and WO2015/051163, the entire content of which is incorporated herein by reference, including all text, tables, equations and drawings.

An outcome and/or classification for a test sample often is ordered by, and often is provided to, a health care professional or other qualified individual (e.g., physician or assistant) who transmits an outcome and/or classification to a subject from whom the test sample is obtained. In certain embodiments, an outcome and/or classification is provided using a suitable visual medium (e.g., a peripheral or component of a machine, e.g., a printer or display). A classification and/or outcome often is provided to a healthcare professional or qualified individual in the form of a report. A report typically comprises a display of an outcome and/or classification (e.g., a value, or an assessment or probability of presence or absence of a genotype, phenotype, genetic variation and/or medical condition), sometimes includes an associated confidence parameter, and sometimes includes a measure of performance for a test used to generate the outcome and/or classification. A report sometimes includes a recommendation for a follow-up procedure (e.g., a procedure that confirms the outcome or classification). A report sometimes includes a visual representation of a chromosome or portion thereof (e.g., a chromosome ideogram or karyogram), and sometimes shows a visualization of a duplication and/or deletion region for a chromosome (e.g., a visualization of a whole chromosome for a chromosome deletion or duplication; a visualization of a whole chromosome with a deleted region or duplicated region shown; a visualization of a portion of chromosome duplicated or deleted; a visualization of a portion of a chromosome remaining in the event of a deletion of a portion of a chromosome) identified for a test sample.

A report can be displayed in a suitable format that facilitates determination of presence or absence of a genotype, phenotype, genetic variation and/or medical condition by a health professional or other qualified individual. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, medical record file, or any other medium described in the previous paragraph. A laboratory file or medical record file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a healthcare professional or other qualified individual to make a determination as to presence or absence of a genotype, phenotype, genetic variation and/or or medical condition for a test sample.

An outcome and/or classification may be provided by and obtained from a laboratory (e.g., obtained from a laboratory file). A laboratory file can be generated by a laboratory that carries out one or more tests for determining presence or absence of a genotype, phenotype, genetic variation and/or medical condition for a test sample. Laboratory personnel (e.g., a laboratory manager) can analyze information associated with test samples (e.g., test profiles, reference profiles, test values, reference values, level of deviation, patient information) underlying an outcome and/or classification. For calls pertaining to presence or absence of a genotype, phenotype, genetic variation and/or medical condition that are close or questionable, laboratory personnel can re-run the same procedure using the same (e.g., aliquot of the same sample) or different test sample from a test subject. A laboratory may be in the same location or different location (e.g., in another country) as personnel assessing the presence or absence of a genotype, phenotype, genetic variation and/or a medical condition from the laboratory file. For example, a laboratory file can be generated in one location and transmitted to another location in which the information for a test sample therein is assessed by a healthcare professional or other qualified individual, and optionally, transmitted to the subject from which the test sample was obtained. A laboratory sometimes generates and/or transmits a laboratory report containing a classification of presence or absence of genomic instability, a genotype, phenotype, a genetic variation and/or a medical condition for a test sample. A laboratory generating a laboratory test report sometimes is a certified laboratory, and sometimes is a laboratory certified under the Clinical Laboratory Improvement Amendments (CLIA).

An outcome and/or classification sometimes is a component of a diagnosis for a subject, and sometimes an outcome and/or classification is utilized and/or assessed as part of providing a diagnosis for a test sample. For example, a healthcare professional or other qualified individual may analyze an outcome and/or classification and provide a diagnosis based on, or based in part on, the outcome and/or classification. In some embodiments, determination, detection or diagnosis of a medical condition, disease, syndrome or abnormality comprises use of an outcome and/or classification determinative of presence or absence of a genotype, phenotype, genetic variation and/or medical condition. In some embodiments, an outcome and/or classification based on counted mapped sequence reads, normalized counts and/or transformations thereof is determinative of presence or absence of a genotype and/or genetic variation. In certain embodiments, a diagnosis comprises determining presence or absence of a condition, syndrome or abnormality. In certain instances, a diagnosis comprises a determination of a genotype or genetic variation as the nature and/or cause of a medical condition, disease, syndrome or abnormality. Thus, provided herein are methods for diagnosing presence or absence of a genotype, phenotype, a genetic variation and/or a medical condition for a test sample according to an outcome or classification generated by methods described herein, and optionally according to generating and transmitting a laboratory report that includes a classification for presence or absence of the genotype, phenotype, a genetic variation and/or a medical condition for the test sample.

An outcome and/or classification sometimes is a component of health care and/or treatment of a subject. An outcome and/or classification sometimes is utilized and/or assessed as part of providing a treatment for a subject from whom a test sample was obtained. For example, an outcome and/or classification indicative of presence or absence of a genotype, phenotype, genetic variation, and/or medical condition is a component of health care and/or treatment of a subject from whom a test sample was obtained. Medical care, treatment and or diagnosis can be in any suitable area of health, such as medical treatment of subjects for prenatal care, cell proliferative conditions, cancer and the like, for example. An outcome and/or classification determinative of presence or absence of a genotype, phenotype, genetic variation and/or medical condition, disease, syndrome or abnormality by methods described herein sometimes is independently verified by further testing. Any suitable type of further test to verify an outcome and/or classification can be utilized, non-limiting examples of which include blood level test (e.g., serum test), biopsy, scan (e.g., CT scan, MRI scan), invasive sampling (e.g., amniocentesis or chorionic villus sampling), karyotyping, microarray assay, ultrasound, sonogram, and the like, for example.

A healthcare professional or qualified individual can provide a suitable healthcare recommendation based on the outcome and/or classification provided in a laboratory report. In some embodiments, a recommendation is dependent on the outcome and/or classification provided (e.g., cancer, stage and/or type of cancer, Down's syndrome, Turner syndrome, medical conditions associated with genetic variations in T13, medical conditions associated with genetic variations in T18). Non-limiting examples of recommendations that can be provided based on an outcome or classification in a laboratory report includes, without limitation, surgery, radiation therapy, chemotherapy, genetic counseling, after-birth treatment solutions (e.g., life planning, long term assisted care, medicaments, symptomatic treatments), pregnancy termination, organ transplant, blood transfusion, further testing described in the previous paragraph, the like or combinations of the foregoing. Thus, methods for treating a subject and methods for providing health care to a subject sometimes include generating a classification for presence or absence of a genotype, phenotype, a genetic variation and/or a medical condition for a test sample by a method described herein, and optionally generating and transmitting a laboratory report that includes a classification of presence or absence of a genotype, phenotype, genetic variation and/or medical condition for the test sample.

Generating an outcome and/or classification can be viewed as a transformation of nucleic acid sequence reads from a test sample into a representation of a subject's cellular nucleic acid. For example, transmuting sequence reads of nucleic acid from a subject by a method described herein, and generating an outcome and/or classification can be viewed as a transformation of relatively small sequence read fragments to a representation of relatively large and complex structure of nucleic acid in the subject. In some embodiments, an outcome and/or classification results from a transformation of sequence reads from a subject into a representation of an existing nucleic acid structure present in the subject (e.g., a genome, a chromosome, chromosome segment, mixture of circulating cell-free nucleic acid fragments in the subject).

In some embodiments, a method herein comprises treating a subject when the presence of a genetic alteration or genetic variation is determined for a test sample from the subject. In some embodiments, treating a subject comprises performing a medical procedure when the presence of a genetic alteration or genetic variation is determined for a test sample. In some embodiments, a medical procedure includes an invasive diagnostic procedure such as, for example, amniocentesis, chorionic villus sampling, biopsy, and the like. For example, a medical procedure comprising amniocentesis or chorionic villus sampling may be performed when the presence of a fetal aneuploidy is determined for a test sample from a pregnant female. In another example, a medical procedure comprising a biopsy may be performed when presence of a genetic alteration indicative of or associated with the presence of cancer is determined for a test sample from a subject. An invasive diagnostic procedure may be performed to confirm a determination of the presence of a genetic alteration or genetic variation and/or may be performed to further characterize a medical condition associated with a genetic alteration or genetic variation, for example. In some embodiments, a medical procedure may be performed as a treatment of a medical condition associated with a genetic alteration or genetic variation. Treatments may include one or more of surgery, radiation therapy, chemotherapy, pregnancy termination, organ transplant, cell transplant, blood transfusion, medicaments, symptomatic treatments, and the like, for example.

In some embodiments, a method herein comprises treating a subject when the absence of a genetic alteration or genetic variation is determined for a test sample from the subject. In some embodiments, treating a subject comprises performing a medical procedure when the absence of a genetic alteration or genetic variation is determined for a test sample. For example, when the absence of a genetic alteration or genetic variation is determined for a test sample, a medical procedure may include health monitoring, retesting, further screening, follow-up examinations, and the like. In some embodiments, a method herein comprises treating a subject consistent with a euploid pregnancy or normal pregnancy when the absence of a fetal aneuploidy, genetic variation or genetic alteration is determined for a test sample from a pregnant female. For example, a medical procedure consistent with a euploid pregnancy or normal pregnancy may be performed when the absence of a fetal aneuploidy, genetic variation or genetic alteration is determined for a test sample from a pregnant female. A medical procedure consistent with a euploid pregnancy or normal pregnancy may include one or more procedures performed as part of monitoring health of the fetus and/or the mother, or monitoring feto-maternal well-being. A medical procedure consistent with a euploid pregnancy or normal pregnancy may include one or more procedures for treating symptoms of pregnancy which may include, for example, one or more of nausea, fatigue, breast tenderness, frequent urination, back pain, abdominal pain, leg cramps, constipation, heartburn, shortness of breath, hemorrhoids, urinary incontinence, varicose veins and sleeping problems. A medical procedure consistent with a euploid pregnancy or normal pregnancy may include one or more procedures performed throughout the course of prenatal care for assessing potential risks, treating complications, addressing preexisting medical conditions (e.g., hypertension, diabetes), and monitoring the growth and development of the fetus, for example. Medical procedures consistent with a euploid pregnancy or normal pregnancy may include, for example, complete blood count (CBC) monitoring, Rh antibody testing, urinalysis, urine culture monitoring, rubella screening, hepatitis B and hepatitis C screening, sexually transmitted infection (STI) screening (e.g., screening for syphilis, chlamydia, gonorrhea), human immunodeficiency virus (HIV) screening, tuberculosis (TB) screening, alpha-fetoprotein screening, fetal heart rate monitoring (e.g., using an ultrasound transducer), uterine activity monitoring (e.g., using toco transducer), genetic screening and/or diagnostic testing for genetic disorders (e.g., cystic fibrosis, sickle cell anemia, hemophilia A), glucose screening, glucose tolerance testing, treatment of gestational diabetes, treatment of prenatal hypertension, treatment of preeclampsia, group B streptococci (GBS) blood type screening, group B strep culture, treatment of group B strep (e.g., with antibiotics), ultrasound monitoring (e.g., routine ultrasound monitoring, level II ultrasound monitoring, targeted ultrasound monitoring), non-stress test monitoring, biophysical profile monitoring, amniotic fluid index monitoring, serum testing (e.g., plasma protein-A (PAPP-A), alpha-fetoprotein (AFP), human chorionic gonadotropin (hCG), unconjugated estriol (uE3), and inhibin-A (inhA) testing), genetic testing, amniocentesis diagnostic testing and chorionic villus sampling (CVS) diagnostic testing.

In some embodiments, a method herein comprises treating a subject consistent with having no cancer when the absence of a genetic variation or genetic alteration is determined for a test sample from a subject. In certain embodiments, a medical procedure consistent with a healthy prognosis may be performed when absence of a genetic alteration or genetic variation associated with cancer is determined for a test sample. For example, medical procedures consistent with a healthy prognosis include without limitation monitoring health of the subject from whom a test sample was tested, performing a secondary test (e.g., a secondary screening test), performing a confirmatory test, monitoring one or more biomarkers associated with cancer (e.g., prostate specific antigen (PSA) in males), monitoring blood cells (e.g., red blood cells, white blood cells, platelets), monitoring one or more vital signs (e.g., heart rate, blood pressure), and/or monitoring one or more blood metabolites (e.g., total cholesterol, HDL (high-density lipoprotein), LDL (low-density lipo-protein), triglycerides, total cholesterol/HDL ratio, glucose, fibrinogen, hemoglobin, dehydroepiandrosterone (DHEA), homocysteine, C-reactive protein, hormones (e.g., thyroid stimulating hormone, testosterone, estrogen, estradiol), creatine, salt (e.g., potassium, calcium), and the like). In some embodiments, a method herein comprises performing no medical procedure, and sometimes no medical procedure that includes invasive sampling, when the absence of a genetic alteration or genetic variation is determined for a test sample.

Machines, Software and Interfaces

Certain processes and methods described herein (e.g., mapping, counting, normalizing, range setting, adjusting, categorizing and/or determining sequence reads, counts, levels and/or profiles) often cannot be performed without a computer, microprocessor, software, module or other machine. Methods described herein typically are computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

Also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., quantifying, counting, filtering, normalizing, transforming, clustering and/or determining sequence reads, counts, levels, profiles and/or outcomes) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Sequence reads, counts, levels and/or profiles sometimes are referred to as "data" or "data sets." In some embodiments, data or data sets can be characterized by one or more features or variables (e.g., sequence based (e.g., GC content, specific nucleotide sequence, the like), function specific (e.g., expressed genes, cancer genes, the like), location based (genome specific, chromosome specific, portion or portion-specific), the like and combinations thereof). In certain embodiments, data or data sets can be organized into a matrix having two or more dimensions based on one or more features or variables. Data organized into matrices can be organized using any suitable features or variables. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine a classification outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a part thereof, and/or padding), providing identification (e.g., identifying a copy number alteration, genetic variation/genetic alteration or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence read quantifications (e.g., counts) sometimes are accessed by a microprocessor that executes instructions configured to carry out a method described herein.

Sequence read quantifications that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation or genetic alteration.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

FIG. 1 illustrates a non-limiting example of a computing environment 110 in which various systems, methods, algorithms, and data structures described herein may be implemented. The computing environment 110 is only one example of a suitable computing environment and is not intended to suggest any limitation as to the scope of use or functionality of the systems, methods, and data structures described herein. Neither should computing environment 110 be interpreted as having any dependency or requirement relating to any one or combination of components illustrated in computing environment 110. A subset of systems, methods, and data structures shown in FIG. 1 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 110 of FIG. 1 includes a general purpose computing device in the form of a computer 120, including a processing unit 121, a system memory 122, and a system bus 123 that operatively couples various system components including the system memory 122 to the processing unit 121. There may be only one or there may be more than one processing unit 121, such that the processor of computer 120 includes a single central-processing unit (CPU), or a plurality of processing units, commonly referred to as a parallel processing environment. The computer 120 may be a conventional computer, a distributed computer, or any other type of computer.

The system bus 123 may be any of several types of bus structures including a memory bus or memory controller, a peripheral bus, and a local bus using any of a variety of bus architectures. The system memory may also be referred to as simply the memory, and includes read only memory (ROM) 124 and random access memory (RAM). A basic input/output system (BIOS) 126, containing the basic routines that help to transfer information between elements within the computer 120, such as during start-up, is stored in ROM 124. The computer 120 may further include a hard disk drive interface 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media.

The hard disk drive 127, magnetic disk drive 128, and optical disk drive 130 are connected to the system bus 123 by a hard disk drive interface 132, a magnetic disk drive interface 133, and an optical disk drive interface 134, respectively. The drives and their associated computer-readable media provide nonvolatile storage of computer-readable instructions, data structures, program modules and other data for the computer 120. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 129, optical disk 131, ROM 124, or RAM, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port, or a universal serial bus (USB). A monitor 147 or other type of display device is also connected to the system bus 123 via an interface, such as a video adapter 148. In addition to the monitor, computers typically include other peripheral output devices (not shown), such as speakers and printers.

The computer 120 may operate in a networked environment using logical connections to one or more remote computers, such as remote computer 149. These logical connections may be achieved by a communication device coupled to or a part of the computer 120, or in other manners. The remote computer 149 may be another computer, a server, a router, a network PC, a client, a peer device or other common network node, and typically includes many or all of the elements described above relative to the computer 120, although only a memory storage device 150 has been illustrated in FIG. 1. The logical connections depicted in FIG. 1 include a local-area network (LAN) 151 and a wide-area network (WAN) 152. Such networking environments are commonplace in office networks, enterprise-wide computer networks, intranets and the Internet, which all are types of networks.

When used in a LAN-networking environment, the computer 120 is connected to the local network 151 through a network interface or adapter 153, which is one type of communications device. When used in a WAN-networking environment, the computer 120 often includes a modem 154, a type of communications device, or any other type of communications device for establishing communications over the wide area network 152. The modem 154, which may be internal or external, is connected to the system bus 123 via the serial port interface 146. In a networked environment, program modules depicted relative to the personal computer 120, or portions thereof, may be stored in the remote memory storage device. It is appreciated that the network connections shown are non-limiting examples and other communications devices for establishing a communications link between computers may be used.

Transformations

As noted above, data sometimes is transformed from one form into another form. The terms "transformed," "transformation," and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's nucleic acid.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, fragment size (e.g., length of CCF fragments, reads or a suitable representation thereof (e.g., FRS)), fragment sequence, identification of a copy number alteration, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principal component analysis of derived quantities; and the like or combinations thereof.

Genetic Variations/Genetic Alterations and Medical Conditions

The presence or absence of a genetic variation can be determined using a method or apparatus described herein. A genetic variation also may be referred to as a genetic alteration, and the terms are often used interchangeably herein and in the art. In certain instances, "genetic alteration" may be used to describe a somatic alteration whereby the genome in a subset of cells in a subject contains the alteration (such as, for example, in tumor or cancer cells). In certain instances, "genetic variation" may be used to describe a variation inherited from one or both parents (such as, for example, a genetic variation in a fetus).

In certain embodiments, the presence or absence of one or more genetic variations or genetic alterations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation or genetic alteration is a chromosome abnormality or copy number alteration (e.g., aneuploidy, duplication of one or more chromosomes, loss of one or more chromosomes, partial chromosome abnormality or mosaicism (e.g., loss or gain of one or more regions of a chromosome), translocation, inversion, each of which is described in greater detail herein). Non-limiting examples of genetic variations/genetic alterations include one or more copy number alterations/variations, deletions (e.g., microdeletions), duplications (e.g., microduplications), insertions, mutations (e.g., single nucleotide variations, single nucleotide alterations), polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

A genetic variation or genetic alteration is sometime a deletion. In certain instances, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a region of a chromosome, an allele, a gene, an intron, an exon, any non-coding region, any coding region, a part thereof or combination thereof. A deletion can comprise a microdeletion. A deletion can comprise the deletion of a single base.

A genetic variation or genetic alteration is sometimes a duplication. In certain instances, a duplication is a mutation (e.g., a genetic aberration) in which a part of a chromosome or a sequence of DNA is copied and inserted back into the genome. In certain embodiments, a genetic duplication (e.g., duplication) is any duplication of a region of DNA. In some embodiments, a duplication is a nucleic acid sequence that is repeated, often in tandem, within a genome or chromosome. In some embodiments, a duplication can comprise a copy of one or more entire chromosomes, a region of a chromosome, an allele, a gene, an intron, an exon, any non-coding region, any coding region, part thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation or genetic alteration is sometimes an insertion. An insertion is sometimes the addition of one or more nucleotide base pairs into a nucleic acid sequence. An insertion is sometimes a microinsertion. In certain embodiments, an insertion comprises the addition of a region of a chromosome into a genome, chromosome, or part thereof. In certain embodiments, an insertion comprises the addition of an allele, a gene, an intron, an exon, any non-coding region, any coding region, part thereof or combination thereof into a genome or part thereof. In certain embodiments, an insertion comprises the addition (e.g., insertion) of nucleic acid of unknown origin into a genome, chromosome, or part thereof. In certain embodiments, an insertion comprises the addition (e.g., insertion) of a single base.

As used herein a "copy number alteration" generally is a class or type of genetic variation, genetic alteration or chromosomal aberration. A copy number alteration also may be referred to as a copy number variation, and the terms are often used interchangeably herein and in the art. In certain instances, "copy number alteration" may be used to describe a somatic alteration whereby the genome in a subset of cells in a subject contains the alteration (such as, for example, in tumor or cancer cells). In certain instances, "copy number variation" may be used to describe a variation inherited from one or both parents (such as, for example, a copy number variation in a fetus). A copy number alteration can be a deletion (e.g., microdeletion), duplication (e.g., a microduplication) or insertion (e.g., a microinsertion). Often, the prefix "micro" as used herein sometimes is a region of nucleic acid less than 5 Mb in length. A copy number alteration can include one or more deletions (e.g., microdeletion), duplications and/or insertions (e.g., a microduplication, microinsertion) of a part of a chromosome. In certain embodiments, a duplication comprises an insertion. In certain embodiments, an insertion is a duplication. In certain embodiments, an insertion is not a duplication.

In some embodiments, a copy number alteration is a copy number alteration from a tumor or cancer cell. In some embodiments, a copy number alteration is a copy number alteration from a non-cancer cell. In certain embodiments, a copy number alteration is a copy number alteration within the genome of a subject (e.g., a cancer patient) and/or within the genome of a cancer cell or tumor in a subject. A copy number alteration can be a heterozygous copy number alteration where the variation (e.g., a duplication or deletion) is present on one allele of a genome. A copy number alteration can be a homozygous copy number alteration where the alteration is present on both alleles of a genome. In some embodiments, a copy number alteration is a heterozygous or homozygous copy number alteration. In some embodiments, a copy number alteration is a heterozygous or homozygous copy number alteration from a cancer cell or non-cancer cell. A copy number alteration sometimes is present in a cancer cell genome and a non-cancer cell genome, a cancer cell genome and not a non-cancer cell genome, or a non-cancer cell genome and not a cancer cell genome.

In some embodiments, a copy number alteration is a fetal copy number alteration. Often, a fetal copy number alteration is a copy number alteration in the genome of a fetus. In some embodiments, a copy number alteration is a maternal and/or fetal copy number alteration. In certain embodiments, a maternal and/or fetal copy number alteration is a copy number alteration within the genome of a pregnant female (e.g., a female subject bearing a fetus), a female subject that gave birth or a female capable of bearing a fetus. A copy number alteration can be a heterozygous copy number alteration where the alteration (e.g., a duplication or deletion) is present on one allele of a genome. A copy number alteration can be a homozygous copy number alteration where the alteration is present on both alleles of a genome. In some embodiments, a copy number alteration is a heterozygous or homozygous fetal copy number alteration. In some embodiments, a copy number alteration is a heterozygous or homozygous maternal and/or fetal copy number alteration. A copy number alteration sometimes is present in a maternal genome and a fetal genome, a maternal genome and not a fetal genome, or a fetal genome and not a maternal genome.

"Ploidy" is a reference to the number of chromosomes present in a subject. In certain embodiments, "ploidy" is the same as "chromosome ploidy." In humans, for example, autosomal chromosomes are often present in pairs. For example, in the absence of a genetic variation or genetic alteration, most humans have two of each autosomal chromosome (e.g., chromosomes 1-22). The presence of the normal complement of 2 autosomal chromosomes in a human is often referred to as euploid or diploid. "Microploidy" is similar in meaning to ploidy. "Microploidy" often refers to the ploidy of a part of a chromosome. The term "microploidy" sometimes is a reference to the presence or absence of a copy number alteration (e.g., a deletion, duplication and/or an insertion) within a chromosome (e.g., a homozygous or heterozygous deletion, duplication, or insertion, the like or absence thereof).

A genetic variation or genetic alteration for which the presence or absence is identified for a subject is associated with a medical condition in certain embodiments. Thus, technology described herein can be used to identify the presence or absence of one or more genetic variations or genetic alterations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations/genetic alterations, medical conditions and states are described hereafter.

Chromosome Abnormalities

In some embodiments, the presence or absence of a chromosome abnormality can be determined by using a method and/or apparatus described herein. Chromosome abnormalities include, without limitation, copy number alterations, and a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refer to a deviation between the structure of the subject chromosome and a normal homologous chromosome. The term "normal" refers to the predominate karyotype or banding pattern found in healthy individuals of a particular species, for example, a euploid genome (e.g., diploid in humans, e.g., 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a region of a chromosome. The term "euploid," in some embodiments, refers a normal complement of chromosomes.

The term "monosomy" as used herein refers to lack of one chromosome of the normal complement. Partial monosomy can occur in unbalanced translocations or deletions, in which only a part of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47,XYY in Jacobs Syndrome). In some embodiments, a trisomy is a duplication of most or all of an autosome. In certain embodiments, a trisomy is a whole chromosome aneuploidy resulting in three instances (e.g., three copies) of a particular type of chromosome (e.g., instead of two instances (e.g., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Medical Disorders and Medical Conditions

Methods described herein can be applicable to any suitable medical disorder or medical condition. Non-limiting examples of medical disorders and medical conditions include cell proliferative disorders and conditions, wasting disorders and conditions, degenerative disorders and conditions, autoimmune disorders and conditions, pre-eclampsia, chemical or environmental toxicity, liver damage or disease, kidney damage or disease, vascular disease, high blood pressure, and myocardial infarction.

In some embodiments, a cell proliferative disorder or condition sometimes is a cancer, tumor, neoplasm, metastatic disease, the like or combination thereof. A cell proliferative disorder or condition sometimes is a disorder or condition of the liver, lung, spleen, pancreas, colon, skin, bladder, eye, brain, esophagus, head, neck, ovary, testes, prostate, the like or combination thereof. Non-limiting examples of cancers include hematopoietic neoplastic disorders, which are diseases involving hyperplastic/neoplastic cells of hematopoietic origin (e.g., arising from myeloid, lymphoid or erythroid lineages, or precursor cells thereof), and can arise from poorly differentiated acute leukemias (e.g., erythroblastic leukemia and acute megakaryoblastic leukemia). Certain myeloid disorders include, but are not limited to, acute promyeloid leukemia (APML), acute myelogenous leukemia (AML) and chronic myelogenous leukemia (CML). Certain lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Certain forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. A cell proliferative disorder sometimes is a non-endocrine tumor or endocrine tumor. Illustrative examples of non-endocrine tumors include, but are not limited to, adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor sometimes is an islet cell tumor.

In some embodiments, a wasting disorder or condition, or degenerative disorder or condition, is cirrhosis, amyotrophic lateral sclerosis (ALS), Alzheimer's disease, Parkinson's disease, multiple system atrophy, atherosclerosis, progressive supranuclear palsy, Tay-Sachs disease, diabetes, heart disease, keratoconus, inflammatory bowel disease (IBD), prostatitis, osteoarthritis, osteoporosis, rheumatoid arthritis, Huntington's disease, chronic traumatic encephalopathy, chronic obstructive pulmonary disease (COPD), tuberculosis, chronic diarrhea, acquired immune deficiency syndrome (AIDS), superior mesenteric artery syndrome, the like or combination thereof.

In some embodiments, an autoimmune disorder or condition is acute disseminated encephalomyelitis (ADEM), Addison's disease, alopecia areata, ankylosing spondylitis, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohns Disease (a type of idiopathic inflammatory bowel disease "IBD"), dermatomyositis, diabetes mellitus type 1, endometriosis, Goodpasture's syndrome, Graves' disease, Guillain-Barré syndrome (GBS), Hashimoto's disease, hidradenitis suppurativa, idiopathic thrombocytopenic purpura, interstitial cystitis, Lupus erythematosus, mixed connective tissue disease, morphea, multiple sclerosis (MS), myasthenia gravis, narcolepsy, euromyotonia, pemphigus vulgaris, pernicious anaemia, polymyositis, primary biliary cirrhosis, rheumatoid arthritis, schizophrenia, scleroderma, Sjögren's syndrome, temporal arteritis (also known as "giant cell arteritis"), ulcerative colitis (a type of idiopathic inflammatory bowel disease "IBD"), vasculitis, vitiligo, Wegener's granulomatosis, the like or combination thereof.

Preeclampsia

In some embodiments, the presence or absence of preeclampsia is determined by using a method or apparatus described herein. Preeclampsia is a condition in which hypertension arises in pregnancy (e.g., pregnancy-induced hypertension) and is associated with significant amounts of protein in the urine. In certain instances, preeclampsia may be associated with elevated levels of extracellular nucleic acid and/or alterations in methylation patterns. For example, a positive correlation between extracellular fetal-derived hypermethylated RASSF1A levels and the severity of preeclampsia has been observed. In certain instances, increased DNA methylation is observed for the H19 gene in preeclamptic placentas compared to normal controls.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g., strain).

Use of Cell Free Nucleic Acid

In certain instances, nucleic acid from abnormal or diseased cells associated with a particular condition or disorder is released from the cells as circulating cell-free nucleic acid (CCF-NA). For example, cancer cell nucleic acid is present in CCF-NA, and analysis of CCF-NA using methods provided herein can be used to determining whether a subject has, or is at risk of having, cancer. Analysis of the presence or absence of cancer cell nucleic acid in CCF-NA can be used for cancer screening, for example. In certain instances, levels of CCF-NA in serum can be elevated in patients with various types of cancer compared with healthy patients. Patients with metastatic diseases, for example, can sometimes have serum DNA levels approximately twice as high as non-metastatic patients. Accordingly, methods described herein can provide an outcome by processing sequencing read counts obtained from CCF-NA extracted from a sample from a subject (e.g., a subject having, suspected of having, predisposed to, or suspected as being predisposed to, a particular condition or disease).

Markers

In certain instances, a polynucleotide in abnormal or diseased cells is modified with respect to nucleic acid in normal or non-diseased cells (e.g., single nucleotide alteration, single nucleotide variation, copy number alteration, copy number variation). In some instances, a polynucleotide is present in abnormal or diseased cells and not present in normal or non-diseased cells, and sometimes a polynucleotide is not present in abnormal or diseased cells and is present in normal or non-diseased cells. Thus, a marker sometimes is a single nucleotide alteration/variation and/or a copy number alteration/variation (e.g., a differentially expressed DNA or RNA (e.g., mRNA)). For example, patients with metastatic diseases may be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Accordingly, methods described herein sometimes provide an outcome based on determining the presence or absence of a particular marker, and sometimes an outcome is presence or absence of a particular type of condition (e.g., a particular type of cancer).

Certain methods described herein may be performed in conjunction with methods described, for example in International Patent Application Publication No. WO2013/052913, International Patent Application Publication No. WO2013/052907, International Patent Application Publication No. WO2013/055817, International Patent Application Publication No. WO2013/109981, International Patent Application Publication No. WO2013/177086, International Patent Application Publication No. WO2013/192562, International Patent Application Publication No. WO2014/116598, International Patent Application Publication No. WO2014/055774, International Patent Application Publication No. WO2014/190286, International Patent Application Publication No. WO2014/205401, International Patent Application Publication No. WO2015/051163, International Patent Application Publication No. WO2015/138774, International Patent Application Publication No. WO2015/054080, International Patent Application Publication No. WO2015/183872, International Patent Application Publication No. WO2016/019042, and International Patent Application Publication No. WO 2016/057901, the entire content of each is incorporated herein by reference, including all text, tables, equations and drawings.

EXAMPLES

The examples set forth below illustrate certain embodiments and do not limit the technology.

Example 1: Materials and Methods

The materials and methods set forth in this example were used, or can be used, to perform certain aspects of the methods and analysis described in Example 2 and Example 3, except where otherwise noted.

DNA Extraction

Whole blood is collected, for example in STRECK BCT tubes, and processed to plasma using the methods previously described (see e.g., Jensen et al. (2013) PLoS One 8(3): e57381). DNA extraction from plasma is performed using HAMILTON liquid handlers.

Library Preparation

After extraction, ccf DNA is used to create sequencing libraries. This process includes the following enzymatic reactions: end repair, mono-adenylation (a-tailing), adapter ligation, and PCR. Adapters include single molecule barcodes or unique molecule identifiers. Since the ligation process occurs prior to PCR, single molecule barcodes enable the differentiation of unique template molecules and can be useful for error correction.

In one example, indexed and single molecule barcoded sequencing libraries were prepared from plasma DNA samples for sequencing on ILLUMINA instruments using NEBNEXT ULTRA biochemistry modified for Oncology library custom adapters. Specifically, custom single molecule barcoded library adapters were hybridized in plate format prior to preparation of sequencing libraries. Generation of Y-shaped custom single molecule barcoded library adapters was achieved by mixing custom P5 and P7 oligonucleotides in equimolar concentration in STE buffer, denaturing this mixture on a thermal cycler, and slowly ramping to room temperature. Sequencing libraries were prepared in a multi-step, automated process using the ZEPHYR liquid handler. The starting material was 40 µL of DNA extracted from plasma or 40 µL of fragmented and size selected DNA extracted from tissue or buffy coat samples. During NEBNEXT ULTRA/Oncology library preparation, a series of enzymatic reactions were performed to modify the dsDNA fragments such that the molecules were amenable to clustering and sequencing on ILLUMINA sequencing platforms. These included: 1) end preparation, 2) adapter ligation, and 3) PCR. Adapter ligation and PCR were each followed by a cleanup step using AMPURE XP beads to remove excess proteins and nucleotides prior to further downstream processing. These cleanup steps were automated in a 96-well plate format. In the first enzymatic step, combined End Prep Enzyme Mix (NEB) and 10× End Repair Reaction Buffer (NEB) were used to: 1) create blunt-ended, 5' phosphorylated fragments via exonuclease and polymerase activities and 2) add a single adenine nucleotide to 3' fragment ends (A-tailing) in order to minimize the incidence of template concatenation and facilitate adapter ligation. To achieve these combined activities, a brief heat inactivation step immediately after blunt-end formation substituted for a more traditional magnetic bead cleanup and catalyzed the A-tailing of DNA fragments. These 3' adenine overhangs were complementary to the thymine overhangs present on custom single molecule barcoded library adapters. The addition of double-stranded Y-shaped adapters to the A-tailed fragments was mediated by Blunt/TA Ligase Master Mix (NEB) and Ligation Enhancer (NEB) in the second enzymatic reaction. Finally, DNA fragments with adapters properly ligated at both ends were selectively amplified using universal forward and universal reverse PCR primers and NEBNEXT Hot Start High-Fidelity 2×PCR Master Mix. The library preparation process was performed in two lab spaces separated by traditional pre- and post-PCR restrictions. The final PCR cleanup step yielded stock libraries eluted in HPLC water that were suitable for dilution, QC, normalization, target capture enrichment, and sequencing on ILLUMINA instruments.

Quantification

After library preparation, the libraries are quantified using capillary electrophoresis (e.g., CALIPER LABCHIP GX) or PCR-based methods (e.g., droplet digital PCR, quantitative PCR). A fixed amount of library is then used as the template for target enrichment. The amount of library used for target enrichment is dependent upon the number of samples multiplexed together prior to target enrichment (e.g., 1 to 24 samples).

Target Enrichment

In order to enable for a certain level of sequencing (e.g., 30,000-fold to 50,000-fold) using as few sequencing reads as possible, hybridization capture methods are utilized to enrich for genomic regions of interest. For this process, biotinylated probes (sometimes referred to as baits) are designed to span regions of interest, manufactured, and pooled together in a single reaction well.

The target enrichment process works by first denaturing the library/libraries and then hybridizing biotinylated probes to the target libraries. This process occurs at an elevated temperature (45° C. to 65° C.) for an extended period of time (4 to 72 hours). Upon completion of the hybridization process, the hybridized probe/library complex is then precipitated using streptavidin coated beads. The beads are washed and the enriched libraries are then amplified using an additional PCR reaction, similar to the PCR reaction used during library preparation. Target enrichment probes may be commercially manufactured, for example by integrated DNA technologies (IDT) and/or ROCHE/NIMBLEGEN, and may be about 60 to 120 bp in length.

In one example, single molecular barcode indexed libraries were target captured using an oncology probe panel for sequencing on ILLUMINA instruments. Specifically, single molecular indexed libraries were captured in a multi-step manual process. The starting material was an adapter ligated, cleaned library eluted in 50 µL of water prepared on the ZEPHYR liquid handler using NEBNEXT ULTRA Biochemistry. During the target capture procedure, a series of steps were performed to capture desired target loci which were amenable to clustering and sequencing on ILLUMINA's HISEQ 2500 instruments including 1) blocking of repetitive elements and adapter sequences, 2) hybridization of capture probes to target DNA, 3) bead binding of capture probes and washing, 3) PCR amplification, and 4) bead cleanup. In the first step, blocking oligos complementary to the ILLUMINA adapters were added along with Cot-1 DNA that blocked repetitive elements in the genome. The blocked DNA was then dried in a CENTRIVAP concentrator centrifuge at 65° C. until samples were completely evaporated. The dried samples were then immediately resuspended using hybridization buffer. During hybridization, the templates were denatured and the blocking elements and biotinylated capture probes subsequently were hybridized. The bound templates were captured with streptavidin-coated magnetic beads, washed to remove unbound template, and then PCR amplified. The amplified products were then SPRI cleaned using AMPURE beads and the entire process was repeated. The final PCR cleanup step yielded stock captured libraries that were ready for dilution, QC, and normalization.

Further Quantification

After completing the target enrichment process, the enriched libraries are quantified using capillary electrophoresis (CALIPER LABCHIP GX) or PCR-based methods (droplet digital PCR, quantitative PCR). Enriched libraries are then normalized to a fixed concentration and loaded onto a next generation sequencing instrument (e.g., ILLUMINA HISEQ 2000/2500).

In one example, an AGILENT BIOANALYZER 2100 was used to quantify sequencing libraries that were prepared from cell-free plasma DNA using NEBNEXT biochemistry and subsequently double captured with an oncology probe panel. Specifically, libraries were analyzed to determine average fragment size distribution and concentration via gel electrophoresis on a micro fluidic platform. The average fragment size of each captured library was determined using smear detection parameters and the concentration was calculated by integration of the electropherogram output. The calculated concentration was used in a subsequent normalization process prior to clustering and sequencing.

Sequencing

Sequencing by synthesis may be performed using single end sequencing or paired end sequencing, for example. Libraries may be sequenced for about 10 to 500 cycles, for example 100 to 150 cycles, for each of the reads.

In one example, sequencing was performed on the ILLUMINA HISEQ 2500 instrument. ILLUMINA's sequencing by synthesis technology uses a reversible terminator-based approach that is able to detect single bases as they are incorporated into a growing DNA strand. A fluorescently-labeled terminator is imaged as each dNTP is added and then cleaved to allow incorporation of the next base. All four reversible terminator-bound dNTPs are present at each cycle so a natural competition between the bases minimizes incorporation bias. After each round of synthesis the clusters are excited by a laser emitting a color that identifies the newly added base. The fluorescent label and blocking group are then removed allowing for the addition of the next base. This biochemistry allows for a single base to be read each cycle. Using the HISEQ 2500 sequencer and reagent kits from ILLUMINA for this example, the clusters on a flow cell were used as templates to generate paired 150 base pair sequencing reads of ~50 million uniquely aligned sequences per sample (when assayed in 6-plex).

Data Analysis

Sequencing reads are aligned to a reference genome with one or more distinct parameter settings. After alignment, certain processes described herein are utilized to evaluate various types of genetic alterations (e.g., single nucleotide alterations, insertions/deletions, fusions, and copy number alterations).

Example 2: Detection of a Copy Number Alteration

In this example, a test sample was analyzed for the presence or absence of a copy number alteration. Sample nucleic acid obtained from a plasma sample from a subject was modified by ligation of adapter oligonucleotides to generate single molecular indexed libraries. Adapter oligonucleotides included a primer annealing polynucleotide (for annealing to flow cell attached oligonucleotides and for annealing to amplification primers), an index polynucleotide (for sample tracking) and a barcode polynucleotide (for tracking individual molecules of sample nucleic acid amplified prior to sequencing). Modified sample nucleic acid was amplified by PCR using universal forward primers and universal reverse primers and NEBNEXT Hot Start High-Fidelity 2×PCR Master Mix.

After amplification, modified sample nucleic acid was subjected to a target capture process. Specifically, sample nucleic acid was contacted with a collection of 3074 probe oligonucleotides under hybridization conditions. Each probe oligonucleotide contained a sequence of 120 bases complementary to sequences in the sample nucleotide (i.e., complementary to certain regions of the human genome). Probes in the collection were selected to target regions of the human genome which may be altered in cancerous tissues. These probes were designed to cover multiple variant types including single nucleotide variants, insertions, deletions, InDels, fusions, translocations, microdeletions, microduplications, aneuploidies, and general copy number alterations.

For the target capture process, single molecular indexed libraries were captured in a multi-step manual process. The starting material was adapter ligated, cleaned library eluted in 50 μL of water prepared on the ZEPHYR liquid handler using NEBNEXT Ultra Biochemistry. During the target capture procedure, a series of steps were performed to capture desired target loci amenable to clustering and sequencing on ILLUMINA's HISEQ 2500 instruments. The steps included (1) blocking of repetitive elements and adapter sequences, (2) hybridization of capture probes to target DNA, (3) bead binding of capture probes and washing, (3) PCR amplification (4) bead cleanup. In the first step, blocking oligos complementary to the ILLUMINA adapters were added along with Cot-1 DNA that blocks repetitive elements in the genome. The blocked DNA was then dried in a CENTRIVAP concentrator centrifuge at 65° C. until samples were completely evaporated. The dried samples were then immediately resuspended using hybridization buffer. During hybridization, the templates (sample nucleic acid) were denatured and subsequently the hybrization of blocking elements and biotinylated capture probes took place. The bound templates were captured with streptavidin-coated magnetic beads, washed to remove unbound template, and then PCR amplified. The amplified products were then SPRI cleaned using AMPURE beads and the entire process was repeated.

After probe oligonucleotide capture and amplification, sample nucleic acid was sequenced using a sequencing by synthesis method (ILLUMINA HISEQ 2500). Sequence reads were aligned to a reference genome (hg19) using a Burrows-Wheeler Aligner (BWA) and subsequently matched to sequences in a padded probe panel (i.e., a panel of sequences comprising genomic sequences corresponding to probe sequences plus 250 nucleotides of genomic sequence upstream and downstream of the probe sequence). Probe coverage quantifications were determined. Specifically, position read coverage for each base in each probe was determined and a median position read coverage was determined for each probe.

Probe coverage quantifications were scaled and normalized according to a sample median and GC correction. Specifically, a probe coverage quantification median for all probes in the sample was determined and probe coverage quantifications for each probe was scaled according to the median by dividing each probe coverage quantification by the probe coverage median for the sample. Probe coverage quantifications also were normalized according to GC content for each probe using a LOESS normalization process.

Probe coverage quantifications from reference samples (i.e., nine euploid samples) also were determined. Specifically, a probe coverage median was determined for each probe according to probe coverage quantifications for each probe across the nine reference samples. Probe coverage quantifications for reference samples also were normalized according to GC content as described above for the test sample.

Probe coverage quantifications for each probe for the sample were transformed into probe log 2 ratios by dividing the normalized probe coverage quantification for each probe for the sample by the probe coverage median determined for each probe according to the reference samples and logarithmically transforming the ratio according to a log 2 transformation. Specifically, a log 2 ratio of probe coverage quantifications (which was proportional to a log 2 ratio for copy number (CN) gain or loss) was determined according to Equation A:

$$\log 2 \text{ ratio} = \log_2 \frac{\text{test coverage}}{\text{normal coverage}} \approx \log_2\left(\frac{CN+2}{2}\right) \quad \text{Equation A}$$

where "test coverage" refers to the scaled and normalized probe coverage quantification for each probe oligonucleotide for the test sample; "normal coverage" refers to probe coverage median for each probe oligonucleotide obtained from reference samples; and CN is the copy number gain or copy number loss for a segment represented by each probe oligonucleotide.

Probe log 2 ratios were fed into a copy number alteration detection procedure using a circular binary segmentation (CBS) method. By comparing to quantifications for the rest of the probes, segmentations (i.e., series of probes; duplicated or deleted) can be detected by CBS. Genes that overlapped with candidate segmentations were identified. Median total read depth (DP) was determined, which is the median log 2 ratio of a gene overlapping with an identified segment. A segment may overlap with multiple genes. For this method, each gene was treated independently such that copy number gain/loss (CN) was reported for each gene according to the median log 2 ratio of a gene (a gene generally contains more than one probe). Copy number gain/loss (CN) was determined according to Equation B:

$$CN = 2*(2^{(segment.median.\log 2ratio)} - 1) \quad \text{Equation B}$$

where the segment.median.log 2ratio=log 2(segment.tumor.median/segment.reference.median) and CN is the copy number gain or copy number loss for each of the segments. The start and end position of the segmentation also was determined.

Figure 14:
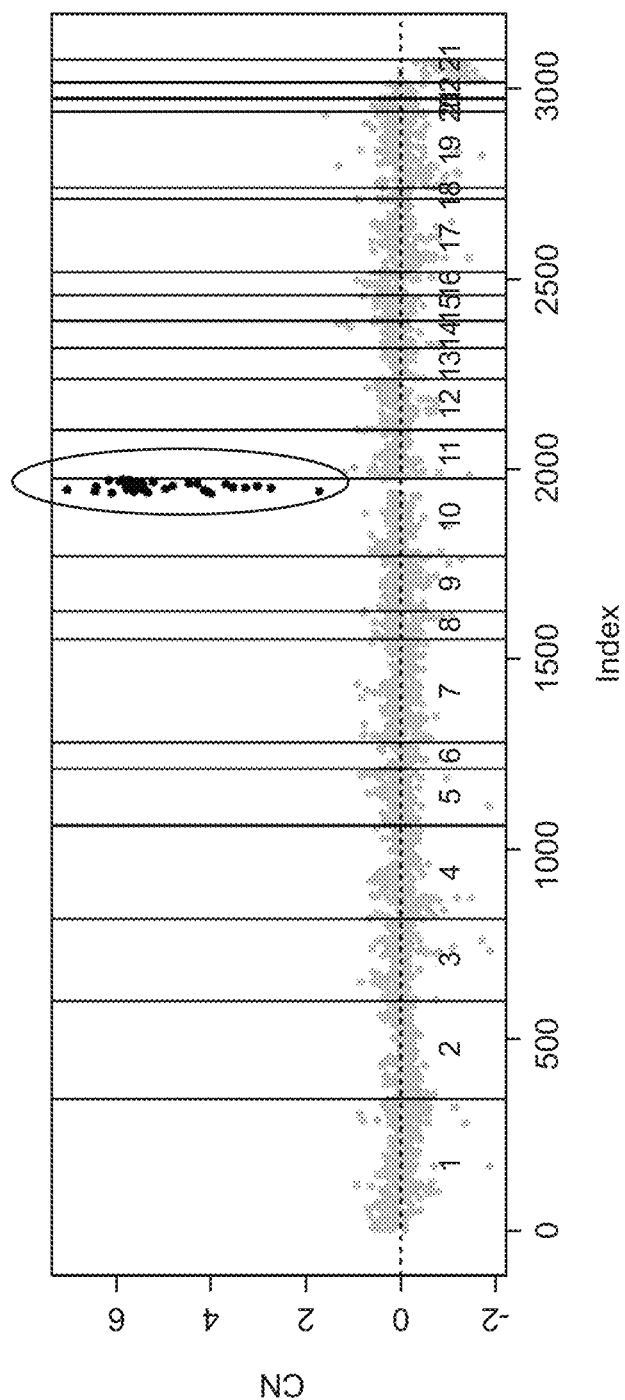
FIG. 14 shows an example plot for a test sample. Probe coverage quantifications (transformed to copy number (CN) gains/losses) are plotted along positions throughout the genome. Each dot represents a probe. A cluster of probes showing significantly higher than normal (i.e., higher than euploid) probe coverage quantifications is circled.

A filtering step was applied to filter out non-significant copy number alterations having low level copy number gains or losses. Segments having less than 0.9 copy number loss or less than 1 copy number gain were filtered out. Specifically, segments for which the corresponding copy number was between 0 and about 1 (for candidate duplications) or between −0.9 and about 0. (for candidate deletions) were filtered away. The results are presented in the profile plot shown in FIG. 14. Each dot represents a probe and the circled cluster of dots indicates a cluster of probes corresponding to filtered segments having significantly higher probe coverage than the other probes. The cluster shown in FIG. 14 was determined to overlap with the FGFR2 gene (chromosome 10, position 123239320-123352632) and the copy number alteration at this location was an approximate 5 copy number gain. Chromosomes are denoted in the plot along the x axis.

In summary, the methods in this Example include data preparation and CNA detection as outlined below.

Data Preparation

1. Probe coverage was obtained from median total read depth of all positions that fall into the probe.

2. Probe coverage was scaled by sample probe coverage median.
3. Probe level was subjected to GC correction using LOESS.
4. Log 2ratio of normalized probe coverage between a testing sample and a normal sample was calculated.

CNA Detection

1. Log 2ratio was used to detect potential CNA with CBS method.
2. All target genes that overlap with CNA were extracted and copy number loss/gain of every amplified/deleted gene was reported in vcf files.
3. Genes reported in vcf with copy number >=1 (amplified) and <=−0.9 (deleted) were considered as significant CNAs.

The methods described in this Example were implemented and tested using the following input files and custom R script:

```
# Input files:
# --tumor_profile: test sample all.calls.csv
# --out_folder: output_folder
# --normal_reference: normalized probe coverage of control samples
# --probe_design: probe bed file with chromosome, probe_start,probe_end and probe_id
# --gc_panel: probe GC content
# --reference_fasta: reference genome fasta file
library(DNAcopy)
arg=commandArgs( )
tumor_profile=unlist(strsplit(arg[ pmatch("--tumor_profile",arg)], "="))[2]
####Fixed input for now:
normal_reference=unlist(strsplit(arg[ pmatch("--normal_reference",arg)], "="))[2]
probe_design=unlist(strsplit(arg[ pmatch("--probe_design",arg)], "="))[2]
gc_panel=unlist(strsplit(arg[ pmatch("--gc_panel",arg)], "="))[2]
reference_fasta=unlist(strsplit(arg[ pmatch("--reference_fasta",arg)], "="))[2]
out_folder=unlist(strsplit(arg[ pmatch("--out_folder",arg)], "="))[2]
sample_ID=unlist(strsplit(tumor_profile,"/"))[
grep("RDOLN",unlist(strsplit(tumor_profile,"/")))[1]]
if (is.na(sample_ID)) {
    sample_ID=unlist(strsplit(unlist(strsplit(tumor_profile,"/"))[
grep("Sample",unlist(strsplit(tumor_profile,"/")))[1]], "_"))[2]
}
if (is.na(sample_ID)) {
    sample_ID=unlist(strsplit(tumor_profile,"/"))[
grep("RDLN",unlist(strsplit(tumor_profile,"/")))[1]]
}
###########################################################################Data preparation##############################################################
###########probe median extraction
tumor_all_calls=read.csv(tumor_profile,stringsAsFactors=F,header=T)
tumor_base_cov=rowSums(tumor_all_calls[,c(grep("AQual0",colnames(tumor_all_calls)):grep("AQual7",colnames(tumor_all_calls)),grep("CQual0",colnames(tumor_all_calls)):grep("CQual7",colnames(tumor_all_calls)),grep("GQual0",colnames(tumor_all_calls)):grep("GQual7",colnames(tumor_all_calls)),grep("TQual0",colnames(tumor_all_calls)):grep("TQual7",colnames(tumor_all_calls)))])
if (median(tumor_base_cov>0)){ ########check if half of the positions are non-zero coverage
probe_info=read.table(probe_design,header=F,sep="\t",stringsAsFactors=F)
probe_info=probe_info[order(probe_info$V2),] #ordered probes
tumor_probe_median=c( )
for (i in 1:nrow(probe_info)){
        tumor_probe_median=c(tumor_probe_median,
median(tumor_base_cov[which(tumor_all_calls$chromosome==probe_info[i,1] & tumor_all_calls$position>=probe_info[i,2] & tumor_all_calls$position<probe_info[i,3])],na.rm=T))
}
names(tumor_probe_median)=probe_info[,4]
scaled_tumor_probe_median=tumor_probe_median/median(tumor_probe_median,na.rm=T)
names(scaled_tumor_probe_median)=probe_info[,4]
############GC correction
gc_info=read.table(gc_panel,header=T,sep="\t",stringsAsFactors=F)
probe_id=sapply(gc_info$ID,function(x) unlist(strsplit(x,">"))[2])
gc_content=round(gc_info[,"X..GCContent"]/100,4)
names(gc_content)=probe_id
GC_correction=function(profile,gc_content){
    # additive fast loess
    median.count <- tapply(profile, gc_content[names(profile)], function(x) median(x, na.rm=T))
    loess.fitted <- loess(median.count ~ as.numeric(names(median.count))) #fit regression on autosome
    median.profile <- median(profile, na.rm=T)
    gc_corrected_profile <- profile + ( median.profile − predict(loess.fitted, gc_content[names(profile)]) )
    return(gc_corrected_profile)
}
gc_corrected_scaled_tumor_probe_median=GC_correction(scaled_tumor_probe_median,gc_content)
###########################################################################CNV detection##############################################################
############log ratio and cna detection
load(normal_reference)
```

```
gc_corrected_scaled_normal_probe_median=normal_control
index=which(gc_corrected_scaled_normal_probe_median>0 &
gc_corrected_scaled_tumor_probe_median>0) ##avoid error for log2( )
log2ratio=rep(0,length(gc_corrected_scaled_normal_probe_median))
log2ratio[index]=log(gc_corrected_scaled_tumor_probe_median[index]/gc_corrected_scaled_no
rmal_probe_median[index],base=2)
names(log2ratio)=probe_info[,4]
write.table(log2ratio,file=paste(out_folder,"/",sample_ID,".normalized.log2ratio.txt",sep=""),quo
te=F,sep="\t",row.names=T,col.names=F)
chromosome=paste("chr",seq(1,22),sep="")
CBS_vcf_out=c( )
for (chr in c(1:22)){
        chr_log2ratio=log2ratio[which(probe_info[,1]==chromosome[chr])]
        chr_tumor_probe_median=tumor_probe_median[which(probe_info[,1]==chromosome[chr])]
        ####probe level change-point detection
        if (length(chr_log2ratio)>0 & sum(chr_log2ratio!=0)>0){
                ##############CBS method
                CNA.object <- CNA(chr_log2ratio, chrom=rep(chr,length(chr_log2ratio)),
maploc=1:length(chr_log2ratio), data.type="logratio", sampleid=sample_ID)
                segment.smoothed.CNA.object <- segment(CNA.object, alpha=0.0005, min.width=5,
verbose=0,p.method="perm")
CBS_out_table=cbind(names(chr_log2ratio)[segment.smoothed.CNA.object$segRows$startRow
],names(chr_log2ratio)[segment.smoothed.CNA.object$segRows$endRow],
rep(chr,nrow(segment.smoothed.CNA.object$segRows)),segment.smoothed.CNA.object$segRo
ws$startRow,segment.smoothed.CNA.object$segRows$endRow,
                                    (segment.smoothed.CNA.object$segRows$endRow -
segment.smoothed.CNA.object$segRows$startRow+1))
        ##########summarize segment information for vcf
        if (nrow(CBS_out_table)>1){ #20160104 YW avoid no segmentation
        for (i in 1:nrow(CBS_out_table)){ ##for CBS
                seg.start=as.numeric(CBS_out_table[i,4])
                seg.end=as.numeric(CBS_out_table[i,5])
                temp.gene_id=sapply(names(chr_log2ratio)[see.start:seg.end],function(x)
unlist(strsplit(x,"_"))[which(is.na(suppressWarnings(as.numeric(unlist(strsplit(x,"_"))))))][1])
                gene.CBS=sapply(temp.gene_id,function(x) unlist(strsplit(unlist(strsplit(unlist(strsplit(x,"-
"))[1],"\\."))[1],";"))[1])
                gene.median.CBS=tapply(chr_log2ratio[seg.start:seg.end], gene.CBS,
median)[unique(gene.CBS)]
                DP.CBS.gene=tapply(chr_tumor_probe_median[seg.start:seg.end], gene.CBS,
median)[unique(gene.CBS)]
                probe_names=names(chr_log2ratio)[seg.start:seg.end]
                all_base_start=sapply(probe_names,function(x) probe_info$V2[which(probe_info$V4==x)])
                all_base_end=sapply(probe_names,function(x) probe_info$V3[which(probe_info$V4==x)])
                base_start=tapply(all_base_start,gene.CBS,min)[unique(gene.CBS)]
                base_end=tapply(all_base_end,gene.CBS,max)[unique(gene.CBS)]
                for (j in 1:length(unique(gene.CBS))){
                        if(gene.median.CBS[j]!=0){
                CN=2*(2^gene.median.CBS[j]-1)
                refbase=toupper(system(paste("samtools faidx ",reference_fasta," chr",chr,":",base_start[j],"-
",base_start[j],sep=""),intern = T)[2])
CBS_vcf_out=rbind(CBS_vcf_out,c(paste("chr",chr,sep=""),base_start[j],".",refbase,"<CNV>","
.","PASS",paste("SVTYPE=CNV;","END=",base_end[j],";","GI=",unique(gene.CBS)[j],sep="")
,"GT:DP:CN",paste("0/1",":",DP.CBS.gene[j],":",round(CN.2),sep="")))
                        }
                }
            }
        }
    }
}
colnames(CBS_vcf_out)=c("#CHROM","POS","ID","REF","ALT","QUAL","FILTER","INFO"
,"FORMAT",sample_ID)
###########vcf output
cat("##fileformat=VCFv4.2", file=paste(out_folder,"/",sample_ID,".CBS.CNV.vcf",sep=""))
cat("\n##source=CNV_detection_oncopipe_V1.2",
file=paste(out_folder,"/",sample_ID,".CBS.CNV.vcf",sep=""),append=TRUE)
cat(paste("\n##fileDate=",date( ),sep=""),
file=paste(out_folder,"/",sample_ID,".CBS.CNV.vcf",sep=""),append=TRUE)
cat(paste("\n##consensusCallsFile=",tumor_profile,sep=""),
file=paste(out_folder,"/",sample_ID,".CBS.CNV.vcf",sep=""),append=TRUE)
cat(paste("\n##INFO=<ID=GI,Number=.,Type=String,Description=\"Gene ID\">",
                    "##FORMAT=<ID=GT,Number=1,Type=String,Description=\"Genotype/">",
                    "##FORMAT=<ID=DP,Number=1,Type=Float,Description=\"Total depth at that
position\">",
                    "##FORMAT=<ID=CN,Number=1,Type=Float,Description\"Copy number gain/lose of
segment containing breakend\">\n",sep="\n"),
file=paste(out_folder,"/",sample_ID,".CBS.CNV.vcf",sep=""),append=TRUE)
write.table(CBS_vcf_out,file=paste(out_folder,"/",sample_ID,".CBS.CNV.vcf",sep=""),quote=F,
sep="\t",row.names=F,col.names=T,append=TRUE)
###############################################Post analysis
```

```
CBS_vcf_out=read.table(paste(out_folder,"/",sample_ID,".CBS.CNV.vcf",sep=""),stringsAsFact
ors = F)
sample_CNV=CBS_vcf_out
CNs=as.numeric(sapply(sample_CNV[,10],function(x) unlist(strsplit(x,":"))[3]))
#########sort CNV with CN values >1 or <-0.9
index=which(CNs<=-0.9 | CNs>=1)
sig_CNV=sample_CNV[index,]
if (nrow(sig_CNV)>0){
colnames(sig_CNV)=c("CHROM","POS","ID","REF","ALT","QUAL","FILTER","INFO","FO
RMAT",sample_ID,"Germline_cnv")
write.csv(sig_CNV,paste(out_folder,"/",sample_ID,".processed.CNV.csv",sep=""),row.names=F
)
}
#####################################################significant CNV visualization
chrs=paste("chr",c(seq(1,22),"X","Y"),sep="")
probe_info_sort_chr=c( )
probe_number_chr=c( )
for (i in 1:24){
    probe_into_sort_chr=rbind(probe_info_sort_chr,probe_info[probe_info[,1]==chrs[i],])
    probe_number_chr=c(probe_number_chr,sum(probe_info[,1]==chrs[i]))
}
chr_separater=cumsum(probe_number_chr)
pdf(paste(out_folder,"/",sample_ID,"_CBS_CNV.pdf",sep=""),width=10,height=5)
if (nrow(sig_CNV)>0){
    my_col=rep("grey",length(log2ratio))
    for (j in 1:nrow(sig_CNV)){
        start=sig_CNV[j,2]
        end=as.numeric(unlist(strsplit(unlist(strsplit(as.character(sig_CNV[j,8]),"END="))[2],";"))[1])
        if (which(probe_info_sort_chr[,1]==as.character(sig_CNV[j,1]) &
probe_info_sort_chr[,2]==start) == which(probe_info_sort_chr[,1]==as.character(sig_CNV[j,1])
& probe_info_sort_chr[,3]==end) ){
                index=which(probe_info_port_chr[,1]=as.character(sig_CNV[j,1]) &
probe_info_sort_chr[,2]==start)}else{
                        index=seq(which(probe_info_sort_chr[,1]==as.character(sig_CNV[j,1]) &
probe_info_sort_chr[,2]==start),which(probe_info_sort_chr[,1]=as.character(sig_CNV[j,1]) &
probe_info_sort_chr[,3]==end))}
        my_col[index]="red"
    }
    CN=2*(2^log2ratio[probe_info_sort _chr[,4]]-1)
    plot(CN,pch=20,col=my_col,ylab="CN")
    abline(v=chr_separater)
    abline(h=0,lty="dashed")
    text(x=c(0,chr_separater[-22])+probe_number_chr/2,y=-1,col="blue",labels =seq(1,22))
}else{
    CN=2*(2^log2ratio[probe_info_sort_chr[,4]]-1)
    plot(CN,pch=20,col="grey",ylab="CN")
    abline(v=chr_separater)
    abline(h=0,lty="dashed")
    text(x=c(0,chr_separater[-22])+probe_number_chr/2,y=-1,col="blue",labels =seq(1,22))
}
dev.off( )
}else{
    cat("##fileformat=VCFv4.2", file=paste(out_folder,"/",sample_ID,".CBS.CNV.vcf",sep=""))
    cat("\n##source=CNV_detection_oncopipe_V1.2",
file=paste(out_folder,"/",sample_ID,".CBS.CNV.vcf",sep=""),append=TRUE)
    cat(paste("\n##fileDate=",date( ),sep=""),
file=paste(out_folder,"/"sample_ID,".CBS.CNV.vcf",sep=""),append=TRUE)
    cat(paste("\n##consensusCallsFile=",tumor_profile,sep=""),
file=paste(out_folder,"/",sample_ID,".CBS.CNV.vcf",sep=""),append=TRUE)
    cat(paste("\n##INFO=<ID=GI,Number=.,Type=String,Description=\"Gene ID\">",
                    "##FORMAT=<ID=GT,Number=1,Type=String,Description=\"Genotype\">",
                    "##FORMAT=<ID=DP,Number=1,Type=Float,Description=\"Total depth at that
position\">",
                    "##FORMAT=<ID=CN,Number=1,Type=Float,Description=\"Copy number gain/lose of
segment containing breakend\">\n",sep="\n"),
file=paste(out_folder,"/",sample_ID,".CBS.CNV.vcf",sep=""),append=TRUE)
}
```

Example 3: Detection of a Copy Number Alteration Using a Z-Score, GATK or PINDEL Method In this example, a test sample was analyzed for the presence or absence of a copy number alteration (CNA) using a Z-score, GATK or PINDEL method. For these methods, sample nucleic acid was modified, captured and sequenced as described in Examples 1 and 2, with the exception that a different probe panel was used for capturing the sample nucleic acid (i.e., a universal carrier screening (UCS) panel).

Z-Score

Using a Z-score method, Z-score of the median probe coverage was calculated to identify copy number alterations. The Z-score was used to determine statistically significant probe coverage differing from expected probe coverage.

This method can be applied on any window size and/or event size, or whole probe, to detect CNA of a specific region.

Normalizing Probe Coverage

To calculate the median coverage per probe (median_coverage_W), the median coverage was computed across all positions spanning the probe:

$$\text{median\_coverage\_}W = \text{median}(\text{coverage\_per\_position\_}w)$$

To correct sample-to-sample coverage variation, median_coverage_W was scaled by the sample median of median_coverage_W:

$$\text{scaled\_median\_coverage\_}W = \frac{\text{median\_coverage\_}W}{\text{median (median\_coverage\_}W)}$$

Figure 15:
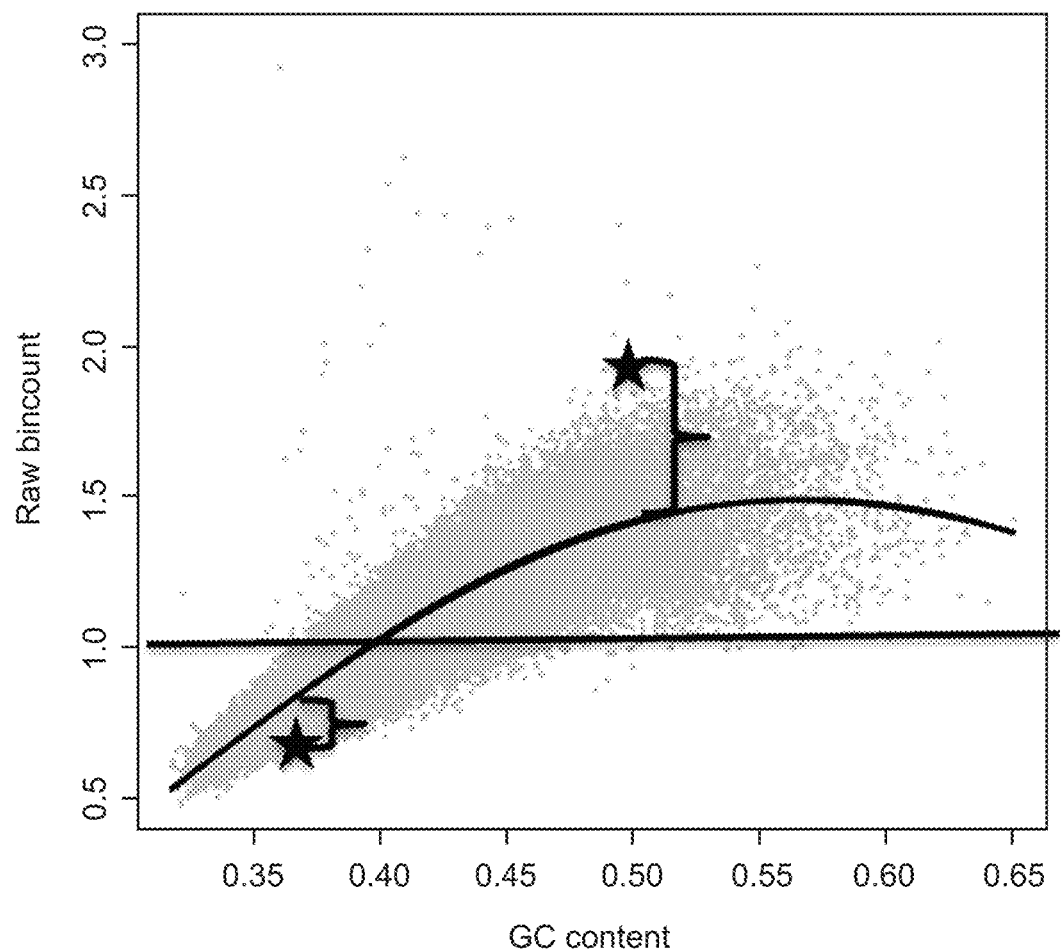
FIG. 15 shows a local polynomial regression of scaled median probe coverage vs. GC content. The horizontal line shows the median of scaled_median_coverage_W; the polynomial regression curve represents noise_due_to_GCbias. Two examples of scaled_median_coverage_W are highlighted as five-point stars and the braces show the GC corrected coverages, i.e., scaled_median_coverage_W− noise_due_to_GCbias.

For GC bias correction, noise_due_to_GCbias was estimated by local polynomial regression (i.e., LOESS) of scaled_median_coverage_W and GC content for all probes, as illustrated in FIG. 15. Then, gc_corrected_scaled_median_coverage_W was determined to eliminate coverage dependency on GC content:

$$\text{gc\_corrected\_scaled\_median\_coverage\_}W = \text{median (scaled\_median\_coverage\_}W) + (\text{scaled\_median\_coverage\_}W - \text{noise\_due\_to\_GCbias})$$

Generating a Normal Gender Specific Profile

Figure 16:
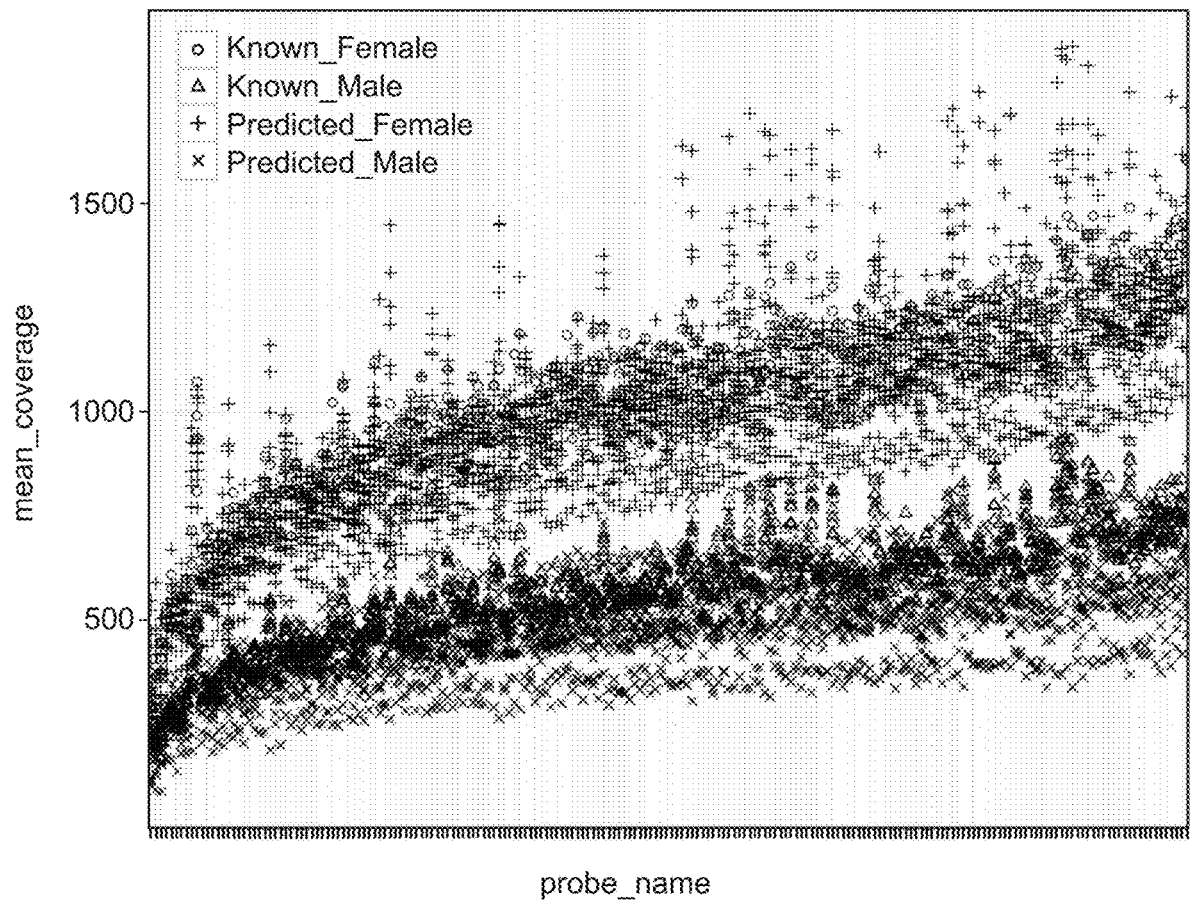
FIG. 16 shows gender specific normal coverage for each probe on chromosome X.

The UCS panel was made up of more than 4000 probes with more than 40% of these probes covering chromosome X. Due to ploidy difference on sex chromosomes (only chromosome X is considered here), gender specific normal coverage profiles were generated to assess the expected coverage, as shown in FIG. 16. 36 normal samples were used to determine normal coverage for each probe; 4 of which were known female samples and 8 of which were known male samples. For the other 24 samples, gender was determined by a paired T test on the mean coverage of chromosome X probes. In total, 17 male samples and 19 female samples were used to profile the normal coverage for each probe.

Chromosome X probes of female samples were processed in the same manner as probes of autosomal chromosomes. For any probe W on chromosome X of male samples, median_coverage_W was first scaled up by a factor of two to compute scaled_median_coverage_W and gc_corrected_scaled_median_coverage_W similar to probe coverage calculations of autosomal chromosomes, however the final median_coverage_W, scaled_median_coverage_W and gc_corrected_scaled_median_coverage_W are only half of the resulting values.

After determining probe coverages for each normal sample S, the normal (expected) and standard deviation of coverage values for each probe are computed across all normal samples:

$$\text{normal\_}v = \text{mean}(v\_S)$$

$$sd\_v = sd(v\_S)$$

where v can be median_coverage_W, scaled_median_coverage_W and gc_corrected_scaled_median_coverage_W.

Calculating Z-Score

For each probe W in a sample, Z-score is defined as:

$$v\_z = (v - \text{normal\_}v)/sd\_v$$

where v can be median_coverage_W, scaled_median_coverage_W and gc_corrected_scaled_median_coverage_W.

Evaluating Z-Score Method Performance

Figure 17:
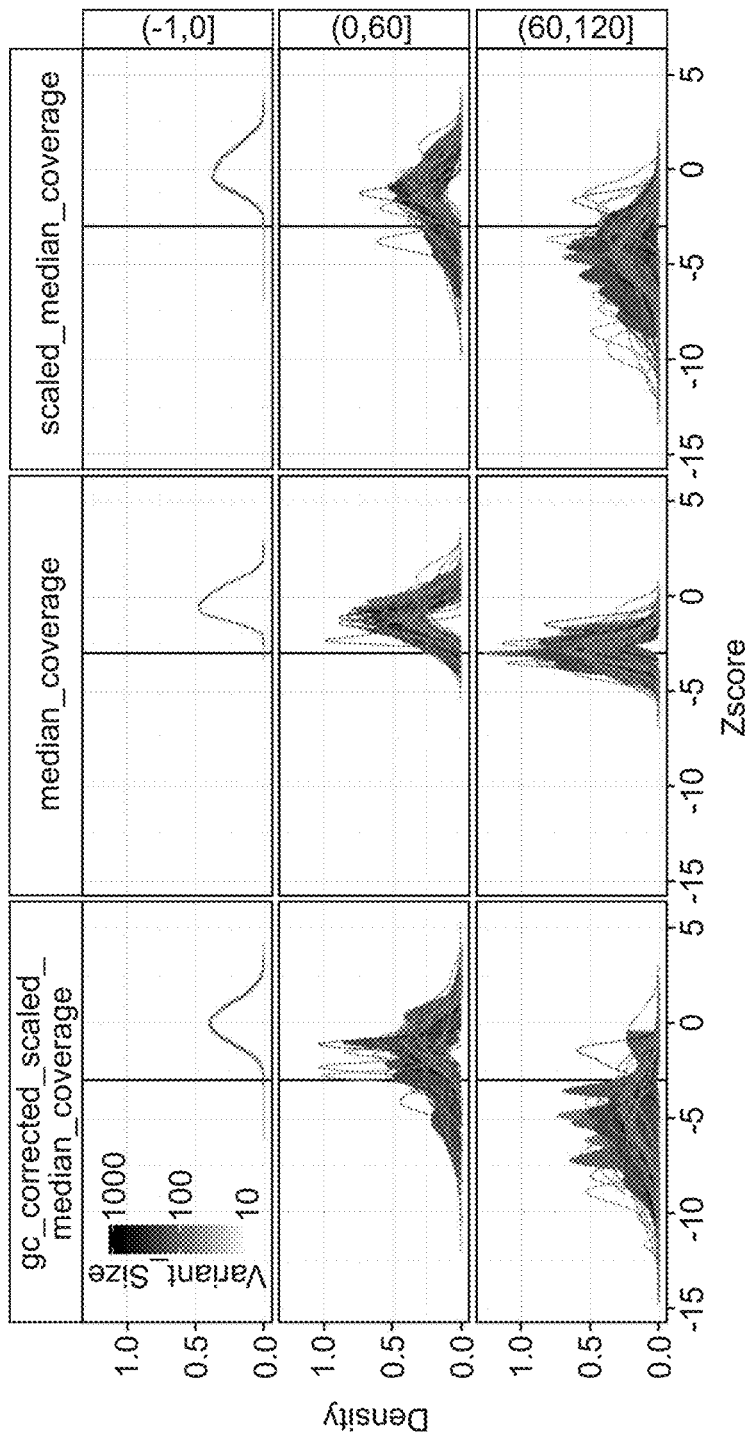
FIG. 17 shows Z-score distributions between no overlapping and high overlapping probes. A Z-score cutoff is shown as a black vertical line in each plot.

To assess the performance of a Z-score method, 110 deletions with sizes ranging from 61 bp to 303,375 bp were simulated. The simulated deletions were spiked into 12 normal samples. The distribution of Z-scores for each deletion simulation is plotted in FIG. 17 for all three coverage types (panel columns) and deletion-probe overlapping size window (panel rows):

As shown in FIG. 17, Z-score distributions between no overlapping and high overlapping probes show significant separation and a Z-score cutoff, z_cut, shown as black vertical lines, can be used to detect probes with a deletion.

Figure 18:
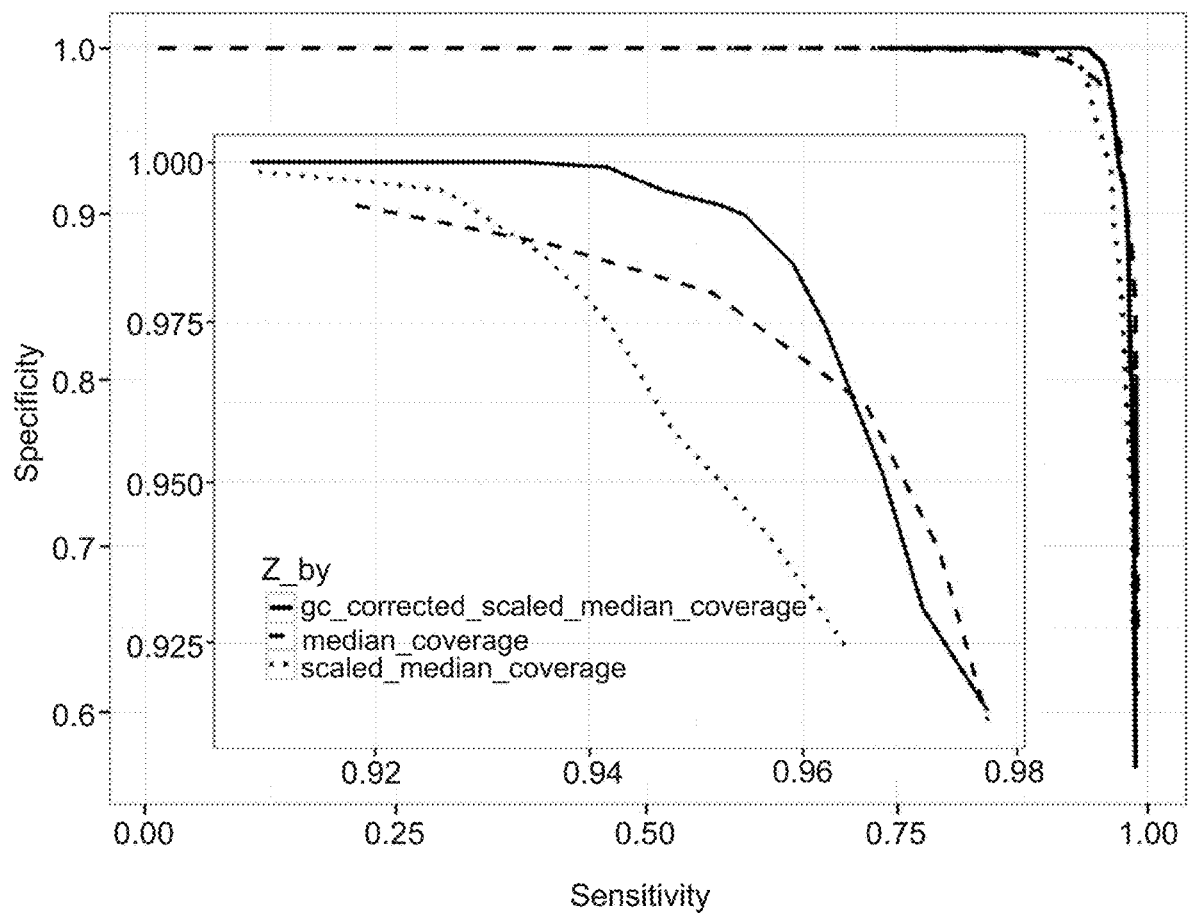
FIG. 18 shows a receiver operating curve generated for 12 normal samples for three types of coverage values: median probe coverage, scaled median probe coverage, and GC-corrected scaled median probe coverage.

To compare performance for all three coverage values and determine the best cutoff value, a receiver operating characteristic (ROC) curve was generated for 12 normal samples as shown in FIG. 18.

Specificity was calculated based on deletions called in the normal samples. Sensitivity was based on deletions called in the simulated samples. A deletion was called if v_z<z_cut for probe W and W overlapped with the deletion region.

Implementation

The methods described in this Example were implemented and tested using the following custom R script:

```
library(DNAcopy)
############ read in command line variables
arg=commandArgs( )
sample_profile=unlist(strsplit(arg[ pmatch("--sample_profile",arg)], "="))[2] # per base coverage
file for sample of interest, e.g. simulated sample with spike-in CNV
normal_reference=unlist(strsplit(arg[ pmatch("--normal_reference",arg)], "="))[2] # per base
reference coverage file for Female or Male
variant=unlist(strsplit(arg[ pmatch("--variant",arg)], "="))[2] # variant region of interest, in the
format of chromosome:variant_start-variant_end
out_prefix=unlist(strsplit(arg[ pmatch("--out_prefix",arg)], "="))[2] # output prefix
gender=sub('-.*','',normal_reference) # sample gender
vchr=sub(".*(chr[0-9XY]+).*","\\1",variant,perl=TRUE) # variant chromosome
vstart=as.numeric(sub('.*:([0-9]+)-.*','\\1',variant)) # variant start position
vend=as.numeric(sub('.*-([0-9]+)','\\1',variant)) # variant end position
############ calculate bin-variant overlap size
normal_profile=read.csv(normal_reference,header=TRUE,stringsAsFactors=FALSE)
names(normal_profile)=gsub('median','normal',names(normal_profile))
overlap_start=sapply(normal_profile$Start,function(x) {if (is.na(vstart)) x else max(vstart,x)})
overlap_end=sapply(normal_profile$Stop,function(x) {if (is.na(vend)) x else min(vend,x)})
normal_profile$Variant_Overlap_Size=sapply(seq(nrow(normal_profile)),
    function(i) if ((normal_profile[i,'Chromosome'] == vchr) &&
(overlap_start[i]<overlap_end[i])) overlap_end[i]-overlap_start[i] else 0)
```

```
############probe median function
get_probe_median <- function(profile,probe) {
    sample_all_calls=read.table(profile,stringsAsFactors=FALSE,header=TRUE)
    sample_base_cov=rowSums(sample_all_calls[,c(grep("AQual0",colnames(sample_all_calls)):gr
ep("AQual7",colnames(sample_all_calls)),grep("CQual0",colnames(sample_all_calls)):grep("C
Qual7",colnames(sample_all_calls)),
grep("GQual0",colnames(sample_all_calls)):grep("GQual7",colnames(sample_all_calls)),grep("
TQual0",colnames(sample_all_calls)):grep("TQual7",colnames(sample_all_calls)))])
    if (median(sample_base_cov>0)){ ########check if half of the positions are non-zero
coverage
        sample_probe_median=c( )
        for (i in 1:nrow(probe)){
            sample_probe_median=c(sample_probe_median,
median(sample_base_cov[which(sample_all_calls$chromosome == probe[i,'Chromosome'] &
sample_all_calls$position>probe[i,'Start'] & sample_all_calls$position<=probe[i,'Stop'])
],na.rm=TRUE))
        }
        probe$median_coverage=sample_probe_median
        return(probe)
    } else {
        stop(paste(profile,'show median coverage = 0'))
    }
}
#### gc correction function
GC_correction=function(profile){
    gc_profile=aggregate(scaled_median_coverage ~ GC.Percent,
                data=profile, function(x) median(x, na.rm=TRUE))
    loess.fitted <- loess(scaled_median_coverage ~ GC.Percent, data=profile) #fit regression on
all chromosome
    median.profile <- median(profile$scaled_median_coverage, na.rm=TRUE)
    profile$gc_corrected_scaled_median_coverage <- profile$scaled_median_coverage + (
median.profile - predict(loess.fitted, profile$GC.Percent))
    return(profile)
}
############probe coverage normalization
T=get_probe_median(sample_profile,normal_profile)
if ( (gender == 'Male') && (chr=='chrX')) {
    T$median_coverage=2*T$median_coverage
}
T$scaled_median_coverage=T$median_coverage/median(T$median_coverage,na.rm=TRUE)
T=GC_correction(T)
if (gender == 'Male') {
    for (i in seq(nrow(T))) {
        if (T[i,'Chromosome'] == 'chrX') {
            T[i,'median_coverage'] = T[i,'median_coverage']/2
            T[i,'scaled_median_coverage'] = T[i,'scaled_median_coverage']/2
            T[i,'gc_corrected_scaled_median_coverage'] =
T[i,'gc_corrected_scaled_median _coverage']/2
        }
    }
}
############Zscore calculation
vcols=c('median_coverage','scaled_median _coverage','gc_corrected_scaled_median_coverage')
for (c in vcols) {
    n_c=sub('median','normal',c)
    T[,paste(c,'zscore',sep='_')]=(T[,c]-T[,n_c])/T[,paste(n_c,'sd',sep='.')]
}
```

Results

The final Z-score cutoff was selected according to a maximum sensitivity*specificity, as shown in Table 1 below.

TABLE 1

| Z_by | Z_cutoff | Sensitivity | Specificity |
|---|---|---|---|
| gc_corrected_scaled_median_coverage | 2.6 | 0.954545 | 0.991667 |

If specificity >0.999 was considered alone, the corresponding best z cutoff is as shown in Table 2 below.

TABLE 2

| Z_by | Z_cutoff | Sensitivity | Specificity |
|---|---|---|---|
| gc_corrected_scaled_median_coverage | 2.9 | 0.941667 | 0.999242 |

GATK and PINDEL

The performance of a Z-score method was compared with other variant callers (CBS, GATK and PINDEL) based on the 12 normal samples and simulations of 110 deletions. Z-score and CBS were performed as described above. GATK (Genome Analysis Toolkit) was performed using GATK HaplotypeCaller version 3.3 employed according to GATK Best Practices workflow (available on the website for Genome Analysis Toolkit) and using all default parameters.

PINDEL was performed using PINDEL version 0.2.4w applied under the default setting (available on the website for PINDEL). The PINDEL software was used with all the default parameters and there were no preprocessing steps prior to running the software. The results are presented in Table 3 below.

TABLE 3

| Caller | Sensitivity (%) | Specificity (%) | Variant Filter |
|---|---|---|---|
| GATK | 13.7 | 100 | RTGTools vcfeval |
| PINDEL | 45.9 | 68.3 | Overlap > 0 bp |
| CBS | 64.5 | 45.2 | Copy number loss/gain < 0 Overlap > 0 bp |
| Z-score | 94.2 | 99.9 | gc_corrected_scaled_median_coverage < −2.9 Overlap > 0 bp |

Figure 19:
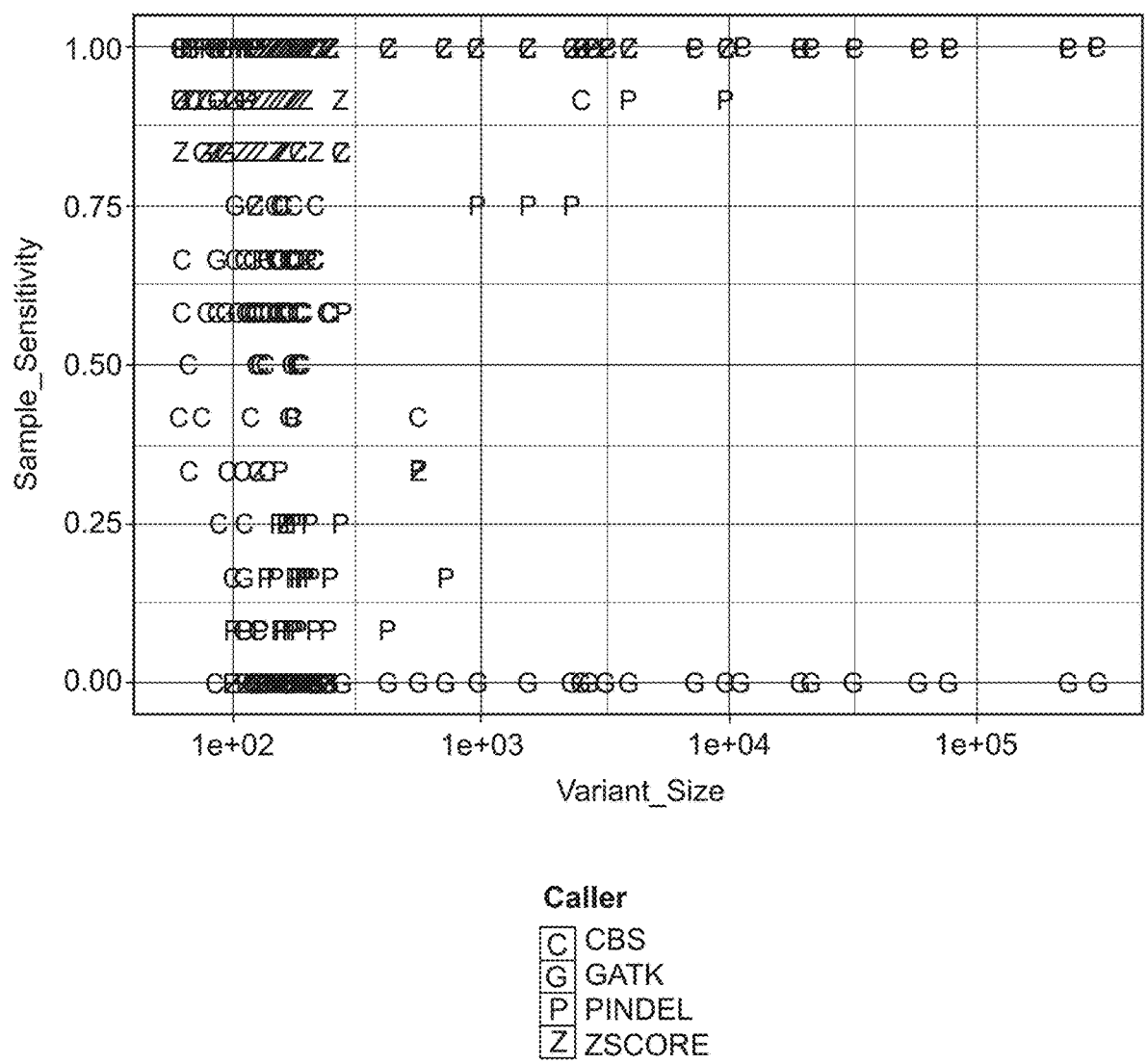
FIG. 19 shows a sensitivity vs. event size comparison for CBS, GATK, PINDEL and z-score variant caller methods.

The performance of a Z-score method was compared with other variant callers based on the 12 normal samples and simulations of 110 deletions, and the results for certain event sizes are presented in Table 4 and Table 5 below and FIG. 19.

TABLE 4

| Caller | Sensitivity (%) | Specificity (%) | Event size (bp) |
|---|---|---|---|
| GATK | 95.8 | 100 | 50≥ and ≤85 |
| PINDEL | 93.9 | 99.32 | 60≥ and ≤100 |
| CBS | 90.8 | 88.6 | >200 |
| Z-score | 94.8 | 100 | >100 |

TABLE 5

| Caller | Sensitivity (%) | Specificity (%) | Event size (bp) |
|---|---|---|---|
| CBS | 100 | 88.9 | >3000 |
| Z-score | 100 | 100 | >3000 |

Example 4: Detection of a Copy Number Alteration in Myeloid Samples Using a CBS and mBPCR Method In this example, a Myeloid test sample was analyzed for the presence or absence of a copy number alteration (CNA) using CBS and mBPCR method. For these methods, sample nucleic acid was modified, captured and sequenced as described in Examples 1 and 2, with the exception that a different probe panel was used for capturing the sample nucleic acid (i.e., a universal carrier screening (UCS) panel).

CDKN2A is a homozygous loss in K562 cell line, copy number=0. Titration levels of K562 into normal samples are denoted in Table 6 by "Conctr" column. Values in "ExpRes", "CBS" and "mBPCR" refer to absolute copy number. Table 7 reports correlation coefficient and root mean squared error of copy number for both methods against expected values. The copy number determined is fairly similar for both algorithms. Correlation of CBS with expected results is slightly larger, but RMSE is slightly worse than for mBPCR. Also, copy number for total loss in K562 sample wasn't reported by CBS.

TABLE 6

| GeneID | FlowcellID | SampleID | Conctr | ExpRes | CBS | mBPCR |
|---|---|---|---|---|---|---|
| CDKN2A | ALP23 | CNVMix1 | 20% K562 | 0.8 | 0.870357 | 0.756250 |
|  |  | CNVMix2 | 30% K562 | 0.7 | 0.831429 | .0.829545 |
|  |  | CNVMix3 | 40% K562 | 0.6 | 0.730357 | 0.730357 |
|  | AVA4A | CNVMix3 | 40% K562 | 0.6 | 0.730357 | 0.730537 |
|  | AYBJL | CNVMix3 | 40% K562 | 0.6 | 0.597143 | 0.587692 |
|  |  | CNVMix3.5 | 50% K562 | 0.5 | 0.533214 | 0.526667 |
|  | AVA4A | CNVMix4 | 60% K562 | 0.4 | 0.412857 | 0.390417 |
|  | AYBHC | CNVMix4 | 60% K562 | 0.4 | 0.362143 | 0.346154 |
|  | AYBJL | CNVMix4 | 60% K562 | 0.4 | 0.441429 | 0.428462 |
|  | AVA4A | CNVMix5 | 80% K562 | 0.2 | 0.220000 | 0.180556 |
|  | AYBHC | CNVMix5 | 80% K562 | 0.2 | 0.226786 | 0.207308 |
|  | AYBJL | CNVMix5 | 80% K562 | 0.2 | 0.204643 | 0.188462 |
|  | ALP23 | K562 |  | 0.0 | NaN | 0.085000 |
|  | AYBHC | MYL56 |  | 0.6 | 0.630714 | 0.601000 |

TABLE 7

|  | #events | Corr | RMSE |
|---|---|---|---|
| CBS | 13 | 0.980922 | .069458 |
| mBPCR | 14 | 0.965501 | 0.068210 |

Example 5: Examples of Embodiments

Provided hereafter are non-limiting examples of embodiments.

A1. A method for determining presence or absence of a copy number alteration for a test subject, comprising:
  (a) providing a set of sequence reads, wherein the sequence reads are obtained from circulating cell free sample nucleic acid from a test subject captured by probe oligonucleotides under hybridization conditions;
  (b) determining a probe coverage quantification of the sequence reads for the probe oligonucleotides; and
  (c) determining the presence or absence of a copy number alteration based on the probe coverage quantification for the probe oligonucleotides for the test sample.

A1.1 The method of embodiment A1, wherein the set of sequence reads in (a) are mapped to genomic portions of a reference genome, and the probe coverage quantification of the sequence reads for the probe oligonucleotides is determined in (b) according to the sequence reads mapped to the genomic portions.

A1.2 The method of embodiment A1 or A1.1, wherein the set of sequence reads in (a) are aligned to probe oligonucleotide sequences, and the probe coverage quantification of the sequence reads for the probe oligonucleotides is determined in (b) according to the sequence reads aligned to the probe oligonucleotide sequences.

A1.3 A method for determining presence or absence of a copy number alteration for a test subject, comprising:
  (a) providing a set of sequence reads, wherein the sequence reads are obtained from circulating cell free sample nucleic acid from a test subject captured by probe oligonucleotides under hybridization conditions;
  (b) determining a probe coverage quantification of consensus sequences generated from the sequence reads for the probe oligonucleotides; and
  (c) determining the presence or absence of a copy number alteration based on the probe coverage quantification for the probe oligonucleotides for the test sample.

B1. A method for determining presence or absence of a copy number alteration for a test subject, comprising:
  (a) providing a set of sequence reads, wherein the sequence reads are obtained from circulating cell free sample nucleic acid from a test subject captured by probe oligonucleotides under hybridization conditions;
  (b) determining a probe coverage quantification of the sequence reads for the probe oligonucleotides;
  (c) normalizing the probe coverage quantification for the probe oligonucleotides, thereby providing a normalized probe coverage quantification for the probe oligonucleotides for the test sample; and
  (d) determining the presence or absence of a copy number alteration based on the normalized probe coverage quantification for the probe oligonucleotides for the test sample.

B1.1 The method of embodiment B1, wherein the set of sequence reads in (a) are mapped to genomic portions of a reference genome, and the probe coverage quantification of the sequence reads for the probe oligonucleotides is determined in (b) according to the sequence reads mapped to the genomic portions.

B1.2 The method of embodiment B1 or B1.1, wherein the set of sequence reads in (a) are aligned to probe oligonucleotide sequences, and the probe coverage quantification of the sequence reads for the probe oligonucleotides is determined in (b) according to the sequence reads aligned to the probe oligonucleotide sequences.

B1.3 A method for determining presence or absence of a copy number alteration for a test subject, comprising:
  (a) providing a set of sequence reads, wherein the sequence reads are obtained from circulating cell free sample nucleic acid from a test subject captured by probe oligonucleotides under hybridization conditions;
  (b) determining a probe coverage quantification of consensus sequences generated from the sequence reads for the probe oligonucleotides;
  (c) normalizing the probe coverage quantification for the probe oligonucleotides, thereby providing a normalized probe coverage quantification for the probe oligonucleotides for the test sample; and
  (d) determining the presence or absence of a copy number alteration based on the normalized probe coverage quantification for the probe oligonucleotides for the test sample.

B2. The method of any one of embodiments B1 to B1.3, wherein the normalizing in (c) comprises scaling the probe coverage quantification for the probe oligonucleotides for the test sample, thereby generating a scaled probe coverage quantification for the probe oligonucleotides.

B3. The method of embodiment B2, wherein the probe coverage quantification for the probe oligonucleotides for the test sample is scaled according to a probe coverage quantification median for all probe oligonucleotides for the test sample.

B4. The method of embodiment B3, wherein the probe coverage quantification for the probe oligonucleotides is divided by the probe coverage median for the probe oligonucleotides in the test sample.

B5. The method of any one of embodiments B1 to B4, wherein the normalizing in (c) comprises normalizing the probe coverage quantification for the probe oligonucleotides, or normalizing the scaled probe coverage quantification for the probe oligonucleotides, according to guanine-cytosine (GC) content, thereby providing a GC normalized probe coverage quantification for the probe oligonucleotides for the test sample.

B6. The method of embodiment B5, wherein the normalizing in (c) comprises normalizing according to GC content for the probe oligonucleotides.

B7. The method of embodiment B5 or B6, wherein the normalizing according to GC content comprises LOESS normalization.

B8. The method of any one of embodiments B1 to B7, wherein the normalizing in (c) comprises normalizing the probe coverage quantification for the probe oligonucleotides, and/or normalizing the scaled probe coverage quantification for the probe oligonucleotides, and/or normalizing the GC normalized probe coverage quantification for the probe oligonucleotides for the test sample, according to a probe coverage median for the probe oligonucleotides obtained from reference samples, thereby generating a reference sample normalized probe coverage quantification for the probe oligonucleotides for the test sample.

B9. The method of embodiment B8, wherein the normalizing according to the probe coverage median comprises dividing each of the probe coverage quantification for the probe oligonucleotides, and/or the scaled probe coverage quantification for the probe oligonucleotides, and/or the GC normalized probe coverage quantification for the probe oligonucleotides for the test sample by the probe coverage median for the probe oligonucleotides obtained from reference samples, thereby providing a ratio for the probe oligonucleotides.

B10. The method of embodiment B9, wherein the normalizing according to the probe coverage median comprises dividing each GC normalized probe coverage quantification for the probe oligonucleotides for the test sample by the probe coverage median for the probe oligonucleotides obtained from reference samples, thereby providing a ratio for the probe oligonucleotides.

B11. The method of any one of embodiments B8 to B10, comprising logarithmically transforming the reference sample normalized probe coverage quantification for the probe oligonucleotides or the ratio for the probe oligonucleotides, thereby generating a logarithmically transformed reference sample normalized probe coverage quantification for the probe oligonucleotides or the ratio for the probe oligonucleotides.

B12. The method of embodiment B11, wherein the logarithmically transformed reference sample normalized probe coverage quantification for the probe oligonucleotides or the ratio for the probe oligonucleotides is a log 2 transformed reference sample normalized probe coverage quantification for the probe oligonucleotides or a log 2 ratio for the probe oligonucleotides.

B13. The method of any one of embodiments B2 to B12, wherein the normalized probe coverage quantification for the probe oligonucleotides for the test sample is the scaled probe coverage quantification for the probe oligonucleotides, the GC normalized probe coverage quantification for the probe oligonucleotides, the reference sample normalized probe coverage quantification for the probe oligonucleotides, the ratio for the probe oligonucleotides, the logarithmically transformed reference sample normalized probe coverage quantification for the probe oligonucleotides or the ratio for the probe oligonucleotides, the log 2 transformed reference sample normalized probe coverage quantification for the probe oligonucleotides and/or the log 2 ratio for the probe oligonucleotides.

B14. The method of any one of embodiments B8 to B13, wherein the reference samples comprise samples classified as not having a copy number alteration.

B15. The method of embodiment B14, wherein the reference samples consist of samples classified as not having a copy number alteration.

B16. The method of embodiment B14 or B15, wherein the reference samples are from human subjects.

B17. The method of embodiment B16, wherein the human subjects are female subjects and/or male subjects.

C1. The method of any one of embodiments A1 to B17, wherein, prior to (a), the sample nucleic acid is contacted with the probe oligonucleotides under hybridization conditions, thereby generating sample nucleic acid hybridized to the probe oligonucleotides.

C1.1 The method of embodiment C1, wherein the probe oligonucleotides comprise probe polynucleotides complementary to sample polynucleotides in the sample nucleic acid.

C1.2. The method of embodiment C1 or C1.1, comprising enriching for fragments in the sample nucleic acid representing one or more selected genes by capturing a subset of the fragments in the sample using probe oligonucleotides complementary to selected genes in the sample nucleic acid.

C2. The method of embodiment C1, C1.1 or C1.2, wherein, prior to (a), the sample nucleic acid is modified, thereby generating modified sample nucleic acid, and the modified sample nucleic acid is contacted with the probe oligonucleotides under hybridization conditions, thereby generating sample nucleic acid hybridized to the probe oligonucleotides.

C3. The method of embodiment C2, wherein the sample nucleic acid is modified by a process comprising ligating one or more adapter oligonucleotides to the sample nucleic acid.

C4. The method of embodiment C3, wherein each of the adapter oligonucleotides includes one or more of a primer annealing polynucleotide, an index polynucleotide and a barcode polynucleotide.

C4.1 The method of any one of embodiments C2 to C4, comprising amplifying the modified sample nucleic acid.

C5. The method of any one of embodiments C1 to C4.1, comprising, prior to (a), dissociating the sample nucleic acid hybridized to the probe oligonucleotides, thereby generating probe oligonucleotide captured sample nucleic acid.

C6. The method of any one of embodiments C1 to C5, comprising, prior to (a), sequencing the sample nucleic acid hybridized to the probe oligonucleotides or sequencing the probe oligonucleotide captured sample nucleic acid, thereby generating the sequence reads.

C7. The method of embodiment C6, wherein the sequencing comprises sequencing by synthesis.

C8. The method of embodiment C6 or C7, wherein the sequencing is at about 1,000-fold to about 100,000-fold coverage.

C9. The method of embodiment C8, wherein the sequencing is at about 10,000-fold to about coverage.

C10. The method of embodiment C9, wherein the sequencing is at about 20,000-fold to about coverage.

C11. The method of embodiment C10, wherein the sequencing is at about 30,000-fold coverage to about 50,000-fold coverage.

C12. The method of any one of embodiments C6 to C11, comprising, prior to (a), mapping the sequence reads to genomic portions of the reference genome.

C13. The method of any one of embodiments A1 to C12, wherein determining the probe coverage quantification comprises determining the number of sequence reads that map at each of the nucleotide positions of the probe oligonucleotides.

C13.1 The method of any one of embodiments A1 to C12, wherein determining the probe coverage quantification comprises determining the number of consensus sequences generated from the sequence reads that map at each of the nucleotide positions of the probe oligonucleotides.

C14. The method of embodiment C13, comprising determining the median number of sequence reads mapped at each of the nucleotide positions for the probe oligonucleotides.

C14.1 The method of embodiment C13.1, comprising determining the median number of consensus sequences mapped at each of the nucleotide positions for the probe oligonucleotides.

C15. The method of embodiment C14, wherein the median number of sequence reads mapped at each of the nucleotide positions for the probe oligonucleotides is the probe coverage quantification for the probe oligonucleotides.

C15.1 The method of embodiment C14.1, wherein the median number of consensus sequences mapped at each of the nucleotide positions for the probe oligonucleotides is the probe coverage quantification for the probe oligonucleotides.

C16. The method of any one of embodiments A1 to C15.1, comprising applying a segmentation process that identifies segments according to the probe coverage quantification and/or the normalized probe coverage quantification for the probe oligonucleotides.

C17. The method of embodiment C16, wherein the segmentation process comprises circular binary segmentation.

C17.1 The method of embodiment C17, wherein a copy number alteration is detected for event sizes of about 200 base pairs or more in length.

C18. The method of embodiment C16, C17 or C17.1, wherein positions for each end of each of the segments, and a probe coverage quantification or the normalized probe coverage quantification, is provided for each of the segments.

C19. The method of any one of embodiments C16 to C18, comprising identifying one or more genes that overlap with each of the segments.

C20. The method of any one of embodiments C16 to C19, comprising determining or estimating the number of copies of each of the segments according to the probe coverage quantification or the normalized probe coverage quantification associated with each of the segments, thereby providing a copy number gain or copy number loss for each of the segments.

C20.1 The method of embodiment C20, wherein the copy number gain or copy number loss for each of the segments is determined or estimated according to a transformation of segment median coverage for each of the segments.

C20.2 The method of embodiment C20 or C20.1, wherein the copy number gain or copy number loss for each of the segments is determined or estimated according to a transformation of segment median coverage log 2 ratio for each of the segments.

C20.3 The method of embodiment C20, C20.1 or C20.2, wherein the copy number gain or copy number loss for each of the segments is determined or estimated according to Equation B:

$$CN = 2*(2^{(segment.median.log\ 2ratio)} - 1) \qquad \text{Equation B}$$

wherein CN is the copy number gain or copy number loss for each of the segments.

C21. The method of any one of embodiments C16 to C20.3, comprising filtering the segments according to the probe coverage quantification, the normalized probe coverage quantification associated with each of the segments, or the copy number gain or copy number loss for each of the segments, thereby providing filtered segments.

C22. The method of embodiment C21, comprising filtering the segments according to the copy number gain or copy number loss for each of the segments, thereby providing filtered segments.

C23. The method of embodiment C22, wherein segments for which there is a 0.9 or greater copy number loss, and segments for which there is a 1 or greater copy number gain, are retained as filtered segments.

C24. The method of any one of embodiments A1 to C23, wherein the test subject is a female.

C25. The method of embodiment C24, wherein the female is a human female.

C26. The method of any one of embodiments A1 to C23, wherein the test subject is a male.

C27. The method of embodiment C26, wherein the test subject is a human male.

C28. The method of any one of embodiments A1 to C27, wherein the genomic portions are of fixed length.

C29. The method of embodiment C28, wherein the genomic portions are of equal length.

C30. The method of embodiment C29, wherein the genomic portions are about 5 to a 150 kilobases in length.

C31. The method of any one of embodiments A1 to C28, wherein at least two of the genomic portions are of unequal length.

C32. The method of any one of embodiments A1 to C31, wherein the genomic portions do not overlap.

C33. The method of embodiment C32, wherein the 3' ends of the genomic portions abut the 5' end of each adjacent and downstream genomic portion.

C34. The method of any one of embodiments A1 to C31, wherein at least two of the genomic portions overlap.

C35. The method of any one of embodiments A1 to C34, wherein (b), (c) and/or (d) are performed by a computer.

C36. The method of embodiment C35, wherein (b), (c) and/or (d) are performed by one or more processors in the computer.

C37. The method of embodiment C35 or C36, wherein (b), (c) and/or (d) are performed according to instructions stored in memory and implemented by the computer.

C38. The method of any one of embodiments A1 to C37, wherein the sample nucleic acid from the test subject is circulating cell free nucleic acid.

C39. The method of embodiment C38, wherein the circulating cell free nucleic acid is from blood plasma or blood serum from the test subject.

C40. The method of any one of embodiments A1 to C39, further comprising enriching for fragments in the sample nucleic acid representing one or more selected genes by amplifying fragments comprising sequences of the one or more selected genes.

D1. The method of any one of A1 to C40, comprising determining a probe coverage quantification for the probe oligonucleotides, and/or a scaled probe coverage quantification for the probe oligonucleotides, and/or a GC normalized probe coverage quantification for the probe oligonucleotides for a plurality of reference samples.

D2. The method of embodiment D1, comprising determining a mean probe coverage quantification for the probe oligonucleotides, and/or a mean scaled probe coverage quantification for the probe oligonucleotides, and/or a mean GC normalized probe coverage quantification for the probe oligonucleotides across the plurality of reference samples, thereby generating a reference mean coverage quantification for the probe oligonucleotides.

D3. The method of embodiment D1 or D2, comprising determining a standard deviation for probe coverage quantification for the probe oligonucleotides, and/or a standard deviation for scaled probe coverage quantification for the probe oligonucleotides, and/or a standard deviation for GC normalized probe coverage quantification for the probe oligonucleotides across the plurality of reference samples, thereby generating a reference standard deviation for the probe oligonucleotides.

D4. The method of embodiment D3, comprising determining a z-score for the probe oligonucleotides according to a test sample coverage quantification, the reference mean coverage quantification, and the reference standard deviation.

D4.1 The method of embodiment D4, wherein a copy number alteration is detected for event sizes of about 100 base pairs or more in length.

D5. The method of embodiment D4 or D4.1, wherein z-score is determined or estimated according to Equation C:

$$z = (v - \text{normal}\_v)/sd\_v \qquad \text{Equation C}$$

wherein z is the z-score for each probe oligonucleotide in a sample; v is the probe coverage quantification for the probe oligonucleotides, or the scaled probe coverage quantification for the probe oligonucleotides, or the GC normalized probe coverage quantification for the probe oligonucleotides for the test sample; normal_v is the mean probe coverage quantification for the probe oligonucleotides, or the mean scaled probe coverage quantification for the probe oligonucleotides, or the mean GC normalized probe coverage quantification for the probe oligonucleotides across the plurality of reference samples; and sd_v is the standard deviation for probe coverage quantification for the probe oligonucleotides, or the standard deviation for scaled probe coverage quantification for the probe oligonucleotides, or the standard deviation for GC normalized probe coverage quantification for the probe oligonucleotides across the plurality of reference samples.

D6. The method of any one of embodiments A1 to D5, wherein the presence or absence of a copy number alteration is determined with a sensitivity of at least about 90% and a specificity of at least about 88%.

D7. The method of any one of embodiments A1 to D5, wherein the presence or absence of a copy number alteration is determined with a sensitivity of at least about 94% and a specificity of at least about 99%.

D8. The method of any one of embodiments A1 to D5, wherein the presence or absence of a copy number alteration is determined with a sensitivity of at least about 94% and a specificity of about 100%.

D9. The method of any one of embodiments A1 to D8, wherein the presence or absence of a copy number alteration is determined using a variant caller method comprising local de-novo assembly.

D10. The method of any one of embodiments A1 to D9, wherein the presence or absence of a copy number alteration is determined using a method comprising a Genome Analysis Toolkit (GATK) variant caller method.

D11. The method of embodiment D9 or D10, wherein a copy number alteration is detected for event sizes between about 50 to about 85 base pairs in length.

D12. The method of embodiment D9, D10 or D11, wherein the presence or absence of a copy number alteration is determined with a sensitivity of at least about 95% and a specificity of about 100%.

D13. The method of any one of embodiments A1 to D8, wherein the presence or absence of a copy number alteration is determined using a variant caller method comprising a pattern growth algorithm.

D14. The method of any one of embodiments A1 to D8 and D13, wherein the presence or absence of a copy number alteration is determined using a method comprising a PINDEL variant caller method.

D15. The method of embodiment D13 or D14, wherein a copy number alteration is detected for event sizes between about 60 to about 100 base pairs in length.

D16. The method of embodiment D13, D14 or D15, wherein the presence or absence of a copy number alteration is determined with a sensitivity of at least about 93% and a specificity of about 99%.

E1. A system, comprising one or more processors and memory, which memory comprises instructions executable by the one or more processors, and which instructions executable by the one or more processors are configured to perform a method of any one of embodiments A1 to D16.

E2. A machine, comprising one or more processors and memory, which memory comprises instructions executable by the one or more processors, and which instructions executable by the one or more processors are configured to perform a method of any one of embodiments A1 to D16.

E3. A computer program product in a computer readable storage medium, the product comprising programed instructions for the computer to perform a method of any one of embodiments A1 to D16.

F1. A method for determining presence or absence of a copy number alteration for a test subject, comprising: providing a set of sequence reads, wherein the sequence reads are obtained from circulating cell free sample nucleic acid from a test sample obtained from the test subject, and the circulating cell free sample nucleic acid is captured by probe oligonucleotides under hybridization conditions; determining, by a computing device, a probe coverage quantification of the sequence reads for the probe oligonucleotides, wherein the determining the probe coverage quantification of the sequence reads comprises determining, by the computing system, a number of the sequence reads that map at each nucleotide position in the probe oligonucleotides; and determining, by the computing device, the presence or absence of a copy number alteration in the circulating cell free sample nucleic acid based on the probe coverage quantification of the sequence reads for the probe oligonucleotides for the test sample.

F2. The method of F1, wherein the set of sequence reads are mapped to genomic portions of a reference genome, and the probe coverage quantification of the sequence reads for the probe oligonucleotides is determined according to the sequence reads mapped to the genomic portions.

F3. The method of F1 to F2, wherein the set of sequence reads are aligned to probe oligonucleotide sequences, and the probe coverage quantification of the sequence reads for the probe oligonucleotides is determined according to the sequence reads aligned to the probe oligonucleotide sequences.

F4. The method of F1 to F3, further comprising generating, by the computing system, consensus sequences from the set of sequence reads, wherein each of the consensus sequences is generated by collapsing sequence reads from the set of sequence reads to generate a single nucleotide sequence that corresponds to at least a portion of the circulating cell free sample nucleic acid, wherein the determining the probe coverage quantification comprises determining the probe coverage quantification of the consensus sequences for the probe oligonucleotides, and wherein the presence or absence of a copy number alteration in the circulating cell free sample nucleic acid is determined based on the probe coverage quantification of the consensus sequence reads for the probe oligonucleotides for the test sample.

F5. The method of F1, F2, or F3, further comprising normalizing, by the computing system, the probe coverage quantification of the sequence reads for the probe oligonucleotides to obtain a normalized probe coverage quantification of the sequence reads for the probe oligonucleotides for the test sample, wherein the presence or absence of the copy number alteration in the circulating cell free sample nucleic acid is determined based on the normalized probe coverage quantification of the sequence reads for the probe oligonucleotides for the test sample.

F6. The method of F5, wherein the normalizing comprises scaling, by the computing system, probe coverage quantification of the sequence reads for the probe oligonucleotides to generate a scaled probe coverage quantification for the probe oligonucleotides.

F7. The method of F6, wherein the probe coverage quantification of the sequence reads for the probe oligonucleotides is scaled according to a probe coverage quantification median for all probe oligonucleotides for the test sample.

F8. The method of F7, wherein the probe coverage quantification of the sequence reads for the probe oligonucleotides is divided by the probe coverage median for the probe oligonucleotides in the test sample.

F9. The method of F5 or F6, wherein the normalizing comprises normalizing, by the computing system, the probe coverage quantification of the sequence reads for the probe oligonucleotides, and/or normalizing, by the computing system, the scaled probe coverage quantification of the sequence reads for the probe oligonucleotides, according to guanine-cytosine (GC) content to provide a GC normalized probe coverage quantification of the sequence reads for the probe oligonucleotides for the test sample.

F10. The method of F9, wherein the normalizing in comprises normalizing according to GC content for the probe oligonucleotides.

F11. The method of F9 or F10, wherein the normalizing according to GC content comprises LOESS normalization.

F12. The method of F5, F6, or F9, wherein the normalizing comprises normalizing, by the computing system, the probe coverage quantification of the sequence reads for the probe oligonucleotides, and/or normalizing, by the computing system, the scaled probe coverage quantification of the sequence reads for the probe oligonucleotides, and/or normalizing, by the computing system, the GC normalized probe coverage quantification of the sequence reads for the probe oligonucleotides, according to a probe coverage median for the probe oligonucleotides obtained from reference samples to generate a reference sample normalized probe coverage quantification of the sequence reads for the probe oligonucleotides for the test sample.

F13. The method of F12, wherein the normalizing according to the probe coverage median comprises dividing each of the probe coverage quantifications of the sequence reads for the probe oligonucleotides, and/or each of the scaled probe coverage quantifications of the sequence reads for the probe oligonucleotides, and/or the GC normalized probe coverage quantifications of the sequence reads for the probe oligonucleotides by the probe coverage median for the probe oligonucleotides obtained from the reference samples to obtain a ratio for the probe oligonucleotides.

F14. The method of F10 or F11, further comprising logarithmically transforming, by the computer system, the reference sample normalized probe coverage quantification of the sequence reads for the probe oligonucleotides or the ratio for the probe oligonucleotides to generate a logarithmically transformed reference sample normalized probe coverage quantification for the probe oligonucleotides or the ratio for the probe oligonucleotides.

F15. The method of F14, wherein the logarithmically transformed reference sample normalized probe coverage quantification for the probe oligonucleotides or the ratio for the probe oligonucleotides is a log 2 transformed reference sample normalized probe coverage quantification for the probe oligonucleotides or a log 2 ratio for the probe oligonucleotides.

F16. The method of F1, F2, F3, or F5, comprising applying, by the computing system, a segmentation process that identifies segments according to the probe coverage quantification of the sequence reads for the probe oligonucleotides and/or the normalized probe coverage quantification of the sequence reads for the probe oligonucleotides.

F17. The method of F16, wherein the segmentation process comprises circular binary segmentation.

F18. The method of F16, the segmentation process comprises a modified bayesian piecewise constant regression.

F19. The method of F17 or F18, wherein positions for each end of each of the segments, and a probe coverage quantification or the normalized probe coverage quantification, is provided for each of the segments.

F20. The method of F19, comprising determining or estimating the number of copies of each of the segments according to the probe coverage quantification or the normalized probe coverage quantification associated with each of the segments to obtain a copy number gain or copy number loss for each of the segments.

F21. The method of F20, wherein the copy number gain or copy number loss for each of the segments is determined or estimated according to a transformation of segment median coverage for each of the segments.

F22. The method of F20, wherein the copy number gain or copy number loss for each of the segments is determined or estimated according to a transformation of segment median coverage log 2 ratio for each of the segments.

F23. The method of F22, wherein the copy number gain or copy number loss for each of the segments is determined or estimated according to Equation B:

$$CN=2*(2^{(segment.median.log\ 2ratio)}-1) \qquad \text{Equation B}$$

wherein the segment.median.log 2ratio=log 2(segment.tumor.median/segment.reference.median) and CN is the copy number gain or copy number loss for each of the segments.

F24. The method of F20, further comprising filtering, by the computing system, the segments according to the probe coverage quantification associated with each of the segments, the normalized probe coverage quantification associated with each of the segments, or the copy number gain or copy number loss for each of the segments in order to obtain filtered segments.

F25. The method of F24, wherein the segments for which the copy number gain is equal to or greater than a first predetermined number and the segments for which the copy number loss is equal to or less than a second predetermined number are retained as filtered segments, and the segments for which the copy number gain or the copy number loss is between the first predetermined number and the second predetermined number are filtered away.

F26. The method of F1, wherein the number of the sequence reads that map at each nucleotide position are determined for each of the probe oligonucleotides to obtain a probe coverage quantification of the sequence reads for each of the probe oligonucleotides.

F27. The of F1, wherein the number of the sequence reads that map at each nucleotide position are determined for groups or regions of probe oligonucleotides to obtain a probe coverage quantification of the sequence reads for the groups or regions of probe oligonucleotides.

F28. A machine, comprising one or more processors and memory, which memory comprises instructions executable by the one or more processors, and which instructions executable by the one or more processors are configured to perform a method of any one of embodiments F1 to F27.

F29. A computer program product in a computer readable storage medium, the product comprising programed instructions for the computer to perform a method of any one of embodiments F1 to F27.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The terms "method" and "process" are used interchangeably herein. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for determining a presence or absence of a copy number alteration for a test subject, comprising:
    obtaining circulating cell free nucleic acid from a test sample from the test subject;
    ligating nucleic acid molecules of the circulating cell free nucleic acid with adapters to generate a plurality of sequence constructs, wherein each sequence construct comprises an adapter ligated to an end of a nucleic acid molecule;
    generating, using a first polymerase chain reaction, library constructs for each sequence construct of the plurality of sequence constructs;
    capturing a subset of the library constructs using probe oligonucleotides under hybridization conditions to enrich for one or more genomic regions of interest, wherein the probe oligonucleotides cover multiple types of genetic alterations;
    generating, using a second polymerase chain reaction, enriched library constructs for each library construct of the subset of the library constructs;
    sequencing the enriched library constructs to obtain sequence reads;
    generating, by a computing system, an alignment computer file comprising on-target sequence reads and associated genomic positioning data, wherein the generating the alignment computer file comprises aligning the sequence reads to a reference genome and matching the aligned sequence reads to genomic sequences in a probe panel to obtain the on-target sequence reads, and wherein the genomic sequences correspond to the probe oligonucleotides;
    generating, by running programming language scripts on the alignment computer file by the computing system, a probe computer file, wherein the generating the probe computer file comprises:
        determining a sample position read coverage for each base in each probe oligonucleotide by quantifying the on-target sequence reads that map to each base in the genomic sequences corresponding to each probe oligonucleotide;
        determining a sample read coverage for each probe oligonucleotide based on the sample position read coverage for each base in the genomic sequences corresponding to the probe oligonucleotide;
        determining a reference read coverage for each probe oligonucleotide based on reference samples; and
        transforming the sample read coverage for each probe oligonucleotide into a probe log 2 ratio by dividing the sample read coverage for each probe oligonucleotide by the reference read coverage for each probe oligonucleotide to obtain a ratio and logarithmically transforming the ratio according to a log 2 transformation; and
    generating, by running variant caller programming language scripts on the probe computer file by the computing system, a variant call file, wherein the generating the variant call file comprises:
        identifying candidate variants based on the probe log 2 ratio for each probe oligonucleotide using a variant caller method; and
        determining the presence or absence of the copy number alteration in the circulating cell free nucleic acid based on the candidate variants.

2. The method of claim 1, wherein the multiple types of genetic alterations that are covered by the probe oligonucleotides comprise at least two genetic alterations selected from a group comprising: single nucleotide variants, insertions, deletions, inserts and deletions (InDels), fusions, translocations, microdeletions, microduplications, aneuploidies, and general copy number alterations.

3. The method of claim 1, further comprising generating, by the computing system, consensus sequences from the on-target sequence reads, wherein each of the consensus sequences is generated by collapsing sequence reads from the on-target sequence reads to generate a single nucleotide sequence that corresponds to at least a portion of the circulating cell free nucleic acid, wherein the determining the sample position read coverage comprises quantifying the consensus sequences that map to each base in the genomic sequences corresponding to the probe oligonucleotides.

4. The method of claim 1, wherein the determining the sample read coverage for each probe oligonucleotide comprises determining a sample position read coverage median for all sample position read coverages in the genomic sequences corresponding to each probe oligonucleotide.

5. The method of claim 4, wherein the sample read coverage for each probe oligonucleotide is scaled by a sample read coverage median for the sample read coverages for all probe oligonucleotides.

6. The method of claim 4, wherein the sample read coverage for each probe oligonucleotide is normalized according to guanine-cytosine (GC) content.

7. The method of claim 6, wherein the sample read coverage for each probe oligonucleotide is normalized according to GC content based on a locally estimated scatterplot smoothing (LOESS) normalization.

8. The method of claim 1, wherein the generating the variant call file further comprises applying, by the computing system, a segmentation process that identifies segments according to the probe log 2 ratio for each probe oligonucleotide.

9. A system for classifying a presence or absence of a copy number alteration for a test sample, comprising:
one or more processors; and
memory coupled to the one or more processors, the memory encoded with a set of instructions configured to perform a process comprising:
obtaining sequence reads by instructing to perform:
obtaining circulating cell free nucleic acid from a test sample from the test subject;
ligating nucleic acid molecules of the circulating cell free nucleic acid with adapters to generate a plurality of sequence constructs, wherein each sequence construct comprises an adapter ligated to an end of a nucleic acid molecule;
generating, using a first polymerase chain reaction, library constructs for each sequence construct of the plurality of sequence constructs;
capturing a subset of the library constructs using probe oligonucleotides under hybridization conditions to enrich for one or more genomic regions of interest, wherein the probe oligonucleotides cover multiple types of genetic alterations;
generating, using a second polymerase chain reaction, enriched library constructs for each library construct of the subset of the library constructs; and
sequencing the enriched library constructs to obtain the sequence reads;
generating an alignment computer file comprising on-target sequence reads and associated genomic positioning data, wherein the generating the alignment computer file comprises aligning the sequence reads to a reference genome and matching the aligned sequence reads to genomic sequences in a probe panel to obtain the on-target sequence reads, and wherein the genomic sequences correspond to the probe oligonucleotides;
generating, by running programming language scripts on the alignment computer file, a probe computer file, wherein the generating the probe computer file comprises:
determining a sample position read coverage for each base in each probe oligonucleotide by quantifying the on-target sequence reads that map to each base in the genomic sequences corresponding to each probe oligonucleotide;
determining a sample read coverage for each probe oligonucleotide based on the sample position read coverage for each base in the genomic sequences corresponding to the probe oligonucleotide;
determining a reference read coverage for each probe oligonucleotide based on reference samples; and
transforming the sample read coverage for each probe oligonucleotide into a probe log 2 ratio by dividing the sample read coverage for each probe oligonucleotide by the reference read coverage for each probe oligonucleotide to obtain a ratio and logarithmically transforming the ratio according to a log 2 transformation; and
generating, by running variant caller programming language scripts on the probe computer file, a variant call file, wherein the generating the variant call file comprises:
identifying candidate variants based on the probe log 2 ratio for each probe oligonucleotide using a variant caller method; and
determining the presence or absence of the copy number alteration in the circulating cell free nucleic acid based on the candidate variants.

10. The system of claim 9, wherein the multiple types of genetic alterations that are covered by the probe oligonucleotides comprise at least two genetic alterations selected from a group comprising: single nucleotide variants, insertions, deletions, inserts and deletions (InDels), fusions, translocations, microdeletions, microduplications, aneuploidies, and general copy number alterations.

11. The system of claim 9, wherein the memory is further configured to perform the process comprising generating consensus sequences from the on-target sequence reads, wherein each of the consensus sequences is generated by collapsing sequence reads from the on-target sequence reads to generate a single nucleotide sequence that corresponds to at least a portion of the circulating cell free nucleic acid, wherein the determining the sample position read coverage comprises quantifying the consensus sequences that map to each base in the genomic sequences corresponding to the probe oligonucleotides.

12. The system of claim 9, wherein the determining the sample read coverage for each probe oligonucleotide comprises determining a sample position read coverage median for all sample position read coverages in the genomic sequences corresponding to each probe oligonucleotide.

13. The system of claim 12, wherein the sample read coverage for each probe oligonucleotide is scaled by a sample read coverage median for the sample read coverages for all probe oligonucleotides.

14. The system of claim 12, wherein the sample read coverage for each probe oligonucleotide is normalized according to guanine-cytosine (GC) content.

15. A non-transitory computer readable storage medium storing instructions that, when executed by one or more processors of a computing system, cause the computing system to perform operations comprising:
obtaining sequence reads by instructing to perform:
obtaining circulating cell free nucleic acid from a test sample from the test subject;
ligating nucleic acid molecules of the circulating cell free nucleic acid with adapters to generate a plurality of sequence constructs, wherein each sequence construct comprises an adapter ligated to an end of a nucleic acid molecule;
generating, using a first polymerase chain reaction, library constructs for each sequence construct of the plurality of sequence constructs;
capturing a subset of the library constructs using probe oligonucleotides under hybridization conditions to enrich for one or more genomic regions of interest, wherein the probe oligonucleotides cover multiple types of genetic alterations;

generating, using a second polymerase chain reaction, enriched library constructs for each library construct of the subset of the library constructs; and sequencing the enriched library constructs to obtain the sequence reads;

generating an alignment computer file comprising on-target sequence reads and associated genomic positioning data, wherein the generating the alignment computer file comprises aligning the sequence reads to a reference genome and matching the aligned sequence reads to genomic sequences in a probe panel to obtain the on-target sequence reads, and wherein the genomic sequences correspond to the probe oligonucleotides;

generating, by running programming language scripts on the alignment computer file, a probe computer file, wherein the generating the probe computer file comprises:

determining a sample position read coverage for each base in each probe oligonucleotide by quantifying the on-target sequence reads that map to each base in the genomic sequences corresponding to each probe oligonucleotide;

determining a sample read coverage for each probe oligonucleotide based on the sample position read coverage for each base in the genomic sequences corresponding to the probe oligonucleotide;

determining a reference read coverage for each probe oligonucleotide based on reference samples; and transforming the sample read coverage for each probe oligonucleotide into a probe log 2 ratio by dividing the sample read coverage for each probe oligonucleotide by the reference read coverage for each probe oligonucleotide to obtain a ratio and logarithmically transforming the ratio according to a log 2 transformation; and generating, by running variant caller programming language scripts on the probe computer file, a variant call file, wherein the generating the variant call file comprises:

identifying candidate variants based on the probe log 2 ratio for each probe oligonucleotide using a variant caller method; and determining a presence or absence of a copy number alteration in the circulating cell free nucleic acid based on the candidate variants.

16. The non-transitory computer readable storage medium of claim 15, wherein the operations further comprising generating consensus sequences from the on-target sequence reads, wherein each of the consensus sequences is generated by collapsing sequence reads from the on-target sequence reads to generate a single nucleotide sequence that corresponds to at least a portion of the circulating cell free nucleic acid, wherein the determining the sample position read coverage comprises quantifying the consensus sequences that map to each base in the genomic sequences corresponding to the probe oligonucleotides.

17. The non-transitory computer readable storage medium of claim 15, wherein the generating the variant call file further comprises applying a segmentation process that identifies segments according to the probe log 2 ratio for each probe oligonucleotide.

* * * * *